United States Patent
Pinsonneault

(10) Patent No.: US 11,587,179 B2
(45) Date of Patent: Feb. 21, 2023

(54) SYSTEMS AND METHODS FOR DETERMINING AND COMMUNICATING PATIENT INCENTIVE INFORMATION TO A PRESCRIBER

(71) Applicant: McKesson Corporation, Irving, TX (US)

(72) Inventor: Roger G. Pinsonneault, Alpharetta, GA (US)

(73) Assignee: MCKESSON CORPORATION, Irving, TX (US)

(*) Notice: Subject to any disclaimer, the term of this patent is extended or adjusted under 35 U.S.C. 154(b) by 586 days.

(21) Appl. No.: 16/552,021

(22) Filed: Aug. 27, 2019

(65) Prior Publication Data
US 2019/0385734 A1    Dec. 19, 2019

Related U.S. Application Data

(63) Continuation of application No. 14/181,011, filed on Feb. 14, 2014, now Pat. No. 10,489,552.

(51) Int. Cl.
*G16H 40/20* (2018.01)
*G16H 10/60* (2018.01)
(Continued)

(52) U.S. Cl.
CPC ............ *G06Q 40/08* (2013.01); *G06Q 10/10* (2013.01); *G16H 20/10* (2018.01); *G16H 40/20* (2018.01); *G16H 10/60* (2018.01)

(58) Field of Classification Search
CPC .............................. G16H 10/60; G16H 40/20
See application file for complete search history.

(56) References Cited

U.S. PATENT DOCUMENTS 5,012,035 A    4/1991  Sartori et al.
5,173,851 A   12/1992  Off et al.
(Continued)

FOREIGN PATENT DOCUMENTS

AU    2003243327 A   12/2003
CA    2 482 370 A    3/2006
(Continued)

OTHER PUBLICATIONS

Wisconsin Physicians Service Health Insurance, "How to Read Your Explanation of Benefits Chart," Jun. 16, 2012 (Year: 2012).*
(Continued)

*Primary Examiner* — John P Go
(74) *Attorney, Agent, or Firm* — Alston & Bird LLP

(57) ABSTRACT

Systems and methods are provided for determining and communicating patient incentive information to a prescriber. The patient incentive information may adjust the patient copay amount for a prescribed medication. The patient incentive information may be determined by evaluating pharmacy identification information and medication identifiers in a received prescription benefit check transaction and/or adjudicated response to a healthcare transaction to determine if an incentive is available to be applied to the current transaction. The incentive amount may be retrieved and the patient copay amount in the adjudicated response may be amended prior to transmitting the adjudicated response to the prescriber of the medication.

18 Claims, 14 Drawing Sheets

(51) Int. Cl.
*G06Q 40/08* (2012.01)
*G16H 20/10* (2018.01)
*G06Q 10/10* (2023.01)

(56) References Cited

U.S. PATENT DOCUMENTS

| | | | |
|---|---|---|---|
| 5,595,342 | A | 1/1997 | McNair et al. |
| 5,628,530 | A | 5/1997 | Thornton |
| 5,726,092 | A | 3/1998 | Mathews et al. |
| 5,757,898 | A | 5/1998 | Nishikawa |
| 5,769,228 | A | 6/1998 | Wroblewski |
| 6,012,035 | A | 1/2000 | Freeman et al. |
| 6,111,218 | A | 8/2000 | Akers et al. |
| 6,463,462 | B1 | 10/2002 | Smith et al. |
| 6,595,342 | B1 | 7/2003 | Maritzen et al. |
| 6,726,092 | B2 | 4/2004 | Goldberg et al. |
| 6,757,898 | B1 | 6/2004 | Ilsen et al. |
| 6,769,228 | B1 | 8/2004 | Mahar |
| 7,155,397 | B2 | 12/2006 | Alexander et al. |
| 7,192,741 | B2 | 3/2007 | Otte et al. |
| 7,337,129 | B1 | 2/2008 | Lowry et al. |
| 7,346,768 | B2 | 3/2008 | DiRienzo |
| 7,409,632 | B1 | 8/2008 | DiRienzo |
| 7,734,483 | B1 | 6/2010 | Smith et al. |
| 7,783,383 | B2 | 8/2010 | Eliuk et al. |
| 7,840,424 | B2 | 11/2010 | Wiley et al. |
| 7,856,364 | B1 | 12/2010 | Wiley et al. |
| 7,912,741 | B1 | 3/2011 | Pinsonneault |
| 7,921,021 | B1 | 4/2011 | Newman |
| 8,036,913 | B1* | 10/2011 | Pinsonneault .......... G06Q 10/10 705/2 |
| 8,036,914 | B1 | 10/2011 | Pinsonneault |
| 8,036,918 | B1 | 10/2011 | Pinsonneault |
| 8,050,943 | B1 | 11/2011 | Wiley et al. |
| 8,060,379 | B1 | 11/2011 | Pinsonneault et al. |
| 8,326,773 | B1 | 12/2012 | Bellamy |
| 8,412,537 | B1 | 4/2013 | Fenton et al. |
| 8,489,415 | B1 | 7/2013 | Ringold |
| 8,521,557 | B1 | 8/2013 | Ringold et al. |
| 8,560,340 | B1 | 10/2013 | Ringold |
| 8,645,162 | B2 | 2/2014 | Boerger et al. |
| 8,671,018 | B2 | 3/2014 | Thomas et al. |
| 8,738,399 | B1 | 5/2014 | Abou Nader et al. |
| 8,786,650 | B1 | 7/2014 | Eller et al. |
| 8,984,059 | B2 | 3/2015 | Johnson |
| 9,026,507 | B2 | 5/2015 | Shraim et al. |
| 9,100,793 | B2 | 8/2015 | Johnson |
| 9,171,322 | B2 | 10/2015 | Spievak et al. |
| 9,356,947 | B2 | 5/2016 | Shraim et al. |
| 9,760,871 | B1 | 9/2017 | Pourfallah et al. |
| 10,157,262 | B1 | 12/2018 | Pinsonneault |
| 10,417,380 | B1 | 9/2019 | Kaye et al. |
| 10,489,552 | B2 | 11/2019 | Pinsonneault |
| 10,496,793 | B1 | 12/2019 | Lawrence et al. |
| 10,565,656 | B1 | 2/2020 | Pinsonneault et al. |
| 10,606,984 | B1 | 3/2020 | Kaye et al. |
| 10,616,146 | B1 | 4/2020 | Hopkins et al. |
| 10,628,797 | B2 | 4/2020 | Shraim et al. |
| 10,642,812 | B1 | 5/2020 | Hopkins et al. |
| 10,713,694 | B1 | 7/2020 | Harris et al. |
| 10,747,848 | B2 | 8/2020 | Guinan |
| 10,778,618 | B2 | 9/2020 | Karnin et al. |
| 10,862,832 | B1 | 12/2020 | Harris |
| 10,924,545 | B2 | 2/2021 | Momchilov et al. |
| 10,924,585 | B1 | 2/2021 | Harris et al. |
| 10,929,932 | B1 | 2/2021 | Golden et al. |
| 10,978,198 | B1 | 4/2021 | Pinsonneault |
| 10,999,224 | B1 | 5/2021 | Frechen et al. |
| 2001/0029483 | A1 | 10/2001 | Schultz et al. |
| 2001/0037216 | A1 | 11/2001 | Oscar et al. |
| 2001/0039589 | A1 | 11/2001 | Aho et al. |
| 2001/0056359 | A1 | 12/2001 | Abreu |
| 2002/0002495 | A1 | 1/2002 | Ullman |
| 2002/0004812 | A1 | 1/2002 | Motoyama |
| 2002/0032582 | A1 | 3/2002 | Feeney et al. |
| 2002/0032583 | A1 | 3/2002 | Joao |
| 2002/0035484 | A1 | 3/2002 | McCormick |
| 2002/0087583 | A1 | 7/2002 | Morgan et al. |
| 2002/0111832 | A1 | 8/2002 | Judge |
| 2002/0147614 | A1 | 10/2002 | Doerr et al. |
| 2002/0188552 | A1 | 12/2002 | Kavounas et al. |
| 2002/0198831 | A1 | 12/2002 | Patricelli et al. |
| 2003/0009367 | A1 | 1/2003 | Morrison |
| 2003/0050796 | A1 | 3/2003 | Baldwin |
| 2003/0050799 | A1 | 3/2003 | Jay et al. |
| 2003/0069760 | A1* | 4/2003 | Gelber .................. G06Q 10/10 705/2 |
| 2003/0074234 | A1 | 4/2003 | Stasny |
| 2003/0097310 | A1 | 5/2003 | Ono et al. |
| 2003/0149625 | A1 | 8/2003 | Leonardi et al. |
| 2003/0154163 | A1 | 8/2003 | Phillips et al. |
| 2003/0172008 | A1 | 9/2003 | Hage et al. |
| 2003/0187690 | A1 | 10/2003 | Miller |
| 2003/0229540 | A1 | 12/2003 | Algiene |
| 2003/0236747 | A1 | 12/2003 | Sager |
| 2004/0039599 | A1 | 2/2004 | Fralic |
| 2004/0054685 | A1 | 3/2004 | Rahn et al. |
| 2004/0059607 | A1 | 3/2004 | Ball et al. |
| 2004/0073456 | A1 | 4/2004 | Gottlieb et al. |
| 2004/0073457 | A1 | 4/2004 | Kalies |
| 2004/0078222 | A1 | 4/2004 | Khan et al. |
| 2004/0078234 | A1 | 4/2004 | Tallal, Jr. |
| 2004/0088187 | A1 | 5/2004 | Chudy et al. |
| 2004/0103062 | A1 | 5/2004 | Wood et al. |
| 2004/0117323 | A1 | 6/2004 | Mindala |
| 2004/0148198 | A1 | 7/2004 | Kalies |
| 2004/0153336 | A1 | 8/2004 | Virdee et al. |
| 2004/0199545 | A1 | 10/2004 | Wagner et al. |
| 2004/0236630 | A1 | 11/2004 | Kost et al. |
| 2004/0249745 | A1 | 12/2004 | Baaren |
| 2005/0015280 | A1 | 1/2005 | Gabel et al. |
| 2005/0060201 | A1 | 3/2005 | Connely, III et al. |
| 2005/0075932 | A1* | 4/2005 | Mankoff ............ G06Q 30/0258 705/14.57 |
| 2005/0080692 | A1 | 4/2005 | Padam et al. |
| 2005/0102169 | A1 | 5/2005 | Wilson |
| 2005/0154627 | A1 | 7/2005 | Zuzek et al. |
| 2005/0187793 | A1 | 8/2005 | Myles |
| 2005/0197862 | A1 | 9/2005 | Paterson et al. |
| 2005/0240442 | A1 | 10/2005 | Lapsker et al. |
| 2005/0240473 | A1 | 10/2005 | Ayers, Jr. et al. |
| 2005/0261939 | A1 | 11/2005 | Augspurger et al. |
| 2005/0288972 | A1 | 12/2005 | Marvin et al. |
| 2006/0020514 | A1 | 1/2006 | Yered |
| 2006/0026041 | A1 | 2/2006 | Ullman |
| 2006/0036470 | A1 | 2/2006 | Oaks |
| 2006/0085231 | A1 | 4/2006 | Brofman |
| 2006/0085385 | A1 | 4/2006 | Foster et al. |
| 2006/0113376 | A1 | 6/2006 | Reed et al. |
| 2006/0149595 | A1 | 7/2006 | Williams et al. |
| 2006/0149784 | A1 | 7/2006 | Tholl et al. |
| 2006/0184391 | A1 | 8/2006 | Barre et al. |
| 2006/0212318 | A1 | 9/2006 | Dooley et al. |
| 2006/0212345 | A1 | 9/2006 | Soza et al. |
| 2006/0224414 | A1* | 10/2006 | Astrup .................. G16H 10/60 705/2 |
| 2006/0224417 | A1 | 10/2006 | Werner |
| 2006/0224443 | A1 | 10/2006 | Soza et al. |
| 2006/0235747 | A1 | 10/2006 | Hammond et al. |
| 2006/0259363 | A1 | 11/2006 | Jhetam et al. |
| 2007/0005402 | A1 | 1/2007 | Kennedy et al. |
| 2007/0033137 | A1 | 2/2007 | Provost et al. |
| 2007/0043589 | A1 | 2/2007 | Warren et al. |
| 2007/0043595 | A1 | 2/2007 | Pederson |
| 2007/0050209 | A1 | 3/2007 | Yered |
| 2007/0050210 | A1 | 3/2007 | Wiley, II |
| 2007/0067186 | A1 | 3/2007 | Brenner et al. |
| 2007/0094133 | A1 | 4/2007 | Anandarao et al. |
| 2007/0108053 | A1 | 5/2007 | Cramer et al. |
| 2007/0136100 | A1 | 6/2007 | Daugherty et al. |
| 2007/0162303 | A1 | 7/2007 | Wiley et al. |
| 2007/0185799 | A1 | 8/2007 | Harrison et al. |
| 2007/0191985 | A1 | 8/2007 | Bain |
| 2007/0194352 | A1 | 8/2007 | Han |

(56) References Cited

U.S. PATENT DOCUMENTS

| | | |
|---|---|---|
| 2007/0202886 A1 | 8/2007 | Dhebri et al. |
| 2007/0204043 A1 | 8/2007 | Espinosa et al. |
| 2007/0219813 A1 | 9/2007 | Moore |
| 2007/0233525 A1 | 10/2007 | Boyle |
| 2007/0233526 A1 | 10/2007 | Hoffman et al. |
| 2007/0239493 A1 | 10/2007 | Sweetland et al. |
| 2007/0250341 A1 | 10/2007 | Howe et al. |
| 2007/0260750 A1 | 11/2007 | Feied et al. |
| 2007/0276697 A1* | 11/2007 | Wiley, II ............ G06Q 30/0207 705/2 |
| 2007/0294765 A1 | 12/2007 | Rihn et al. |
| 2007/0299915 A1 | 12/2007 | Shraim et al. |
| 2008/0033750 A1 | 2/2008 | Burriss et al. |
| 2008/0103836 A1 | 5/2008 | Park et al. |
| 2008/0112411 A1 | 5/2008 | Stafford et al. |
| 2008/0152107 A1 | 6/2008 | Mendiola |
| 2008/0215361 A1 | 9/2008 | Nunnari et al. |
| 2008/0262948 A1 | 10/2008 | Grady et al. |
| 2009/0030719 A1 | 1/2009 | Nadas et al. |
| 2009/0064330 A1 | 3/2009 | Shraim et al. |
| 2009/0094051 A1 | 4/2009 | Ard et al. |
| 2009/0100099 A1 | 4/2009 | Buckwalter |
| 2009/0112707 A1 | 4/2009 | Weiss et al. |
| 2009/0204477 A1 | 8/2009 | Urso |
| 2009/0287558 A1 | 11/2009 | Seth et al. |
| 2009/0313112 A1 | 12/2009 | Champ et al. |
| 2009/0327363 A1 | 12/2009 | Cullen et al. |
| 2010/0030667 A1 | 2/2010 | Chudy et al. |
| 2010/0070298 A1 | 3/2010 | Kalies |
| 2010/0144259 A1 | 6/2010 | Allexon et al. |
| 2010/0145730 A1 | 6/2010 | Abreu |
| 2010/0161353 A1 | 6/2010 | Mayaud |
| 2010/0217622 A1 | 8/2010 | Brown et al. |
| 2010/0285821 A1 | 11/2010 | Smeeding et al. |
| 2010/0293236 A1 | 11/2010 | Wisner et al. |
| 2011/0112871 A1 | 5/2011 | Simonowski et al. |
| 2011/0161109 A1 | 6/2011 | Pinsonneault et al. |
| 2011/0196697 A1 | 8/2011 | Akers |
| 2011/0288925 A1 | 11/2011 | Thomas et al. |
| 2012/0053958 A1 | 3/2012 | Marshall et al. |
| 2012/0136809 A1 | 5/2012 | Cannata et al. |
| 2012/0143627 A1 | 6/2012 | Ruben et al. |
| 2012/0166268 A1* | 6/2012 | Griffiths ............ G06Q 30/0222 705/14.23 |
| 2012/0179481 A1 | 7/2012 | Patel et al. |
| 2012/0185263 A1 | 7/2012 | Emert |
| 2012/0185264 A1 | 7/2012 | Demogenes et al. |
| 2012/0253829 A1 | 10/2012 | John et al. |
| 2012/0253830 A1 | 10/2012 | John et al. |
| 2012/0253831 A1 | 10/2012 | John et al. |
| 2012/0253832 A1 | 10/2012 | John et al. |
| 2012/0253833 A1 | 10/2012 | John et al. |
| 2012/0253846 A1 | 10/2012 | John et al. |
| 2012/0265591 A1 | 10/2012 | Hwang |
| 2013/0041968 A1 | 2/2013 | Cohen et al. |
| 2013/0103602 A1 | 4/2013 | Melnick et al. |
| 2013/0144715 A1 | 6/2013 | Kranzley et al. |
| 2013/0197980 A1 | 8/2013 | Lerner et al. |
| 2013/0246082 A1 | 9/2013 | Brylawski et al. |
| 2013/0311389 A1 | 11/2013 | Kaehler et al. |
| 2014/0039911 A1 | 2/2014 | Iyer |
| 2014/0088985 A1 | 3/2014 | Grant et al. |
| 2014/0214435 A1 | 7/2014 | Previdi |
| 2014/0249861 A1 | 9/2014 | Gamble et al. |
| 2014/0249864 A1 | 9/2014 | Sultan et al. |
| 2014/0278456 A1 | 9/2014 | Milosevich et al. |
| 2015/0088557 A1 | 3/2015 | Huynh et al. |
| 2015/0142479 A1 | 5/2015 | Porter et al. |
| 2015/0149197 A1 | 5/2015 | Guinan |
| 2015/0154565 A1 | 6/2015 | Kaehler et al. |
| 2015/0154588 A1 | 6/2015 | Purves et al. |
| 2015/0195224 A1 | 7/2015 | Karnin et al. |
| 2015/0213195 A1 | 7/2015 | Blechman |
| 2015/0234991 A1 | 8/2015 | Pinsonneault |
| 2015/0235177 A1 | 8/2015 | Shraim et al. |
| 2015/0269695 A1 | 9/2015 | Pinsonneault et al. |
| 2015/0332422 A1 | 11/2015 | Gilmartin |
| 2015/0371000 A1 | 12/2015 | Pinsonneault |
| 2016/0012465 A1 | 1/2016 | Sharp |
| 2016/0140593 A1 | 5/2016 | Smeeding et al. |
| 2016/0213512 A1 | 7/2016 | Palanker et al. |
| 2016/0267544 A1 | 9/2016 | Flood et al. |
| 2016/0267545 A1 | 9/2016 | Glass et al. |
| 2016/0307195 A1 | 10/2016 | Cantwell et al. |
| 2016/0358142 A1 | 12/2016 | Hillen |
| 2016/0359795 A1 | 12/2016 | Fehling |
| 2017/0034087 A1 | 2/2017 | Borenstein et al. |
| 2017/0220768 A1 | 8/2017 | Tanner, Jr. et al. |
| 2017/0323295 A1 | 11/2017 | Kranzley et al. |
| 2017/0324695 A1 | 11/2017 | Fischer et al. |
| 2018/0012244 A1 | 1/2018 | Leonardi |
| 2018/0366810 A1 | 12/2018 | Nero et al. |
| 2019/0213212 A1 | 7/2019 | Adato et al. |
| 2019/0385733 A1 | 12/2019 | Kaye et al. |
| 2021/0319887 A1 | 10/2021 | Derrick, Jr. et al. |

FOREIGN PATENT DOCUMENTS

| | | |
|---|---|---|
| CA | 2792252 A1 | 4/2013 |
| CA | 2810686 A1 | 10/2013 |
| CN | 102362778 | 2/2012 |
| KR | 100755440 | 9/2007 |
| KR | 100793852 | 1/2008 |
| KR | 101038074 | 6/2011 |
| KR | 101101692 | 12/2011 |
| KR | 20110138108 | 12/2011 |
| KR | 20110138572 | 12/2011 |
| KR | 101154858 | 6/2012 |
| WO | WO 1991/006917 | 5/1991 |
| WO | WO 1995 003569 A2 | 2/1995 |
| WO | WO 1997/025682 | 7/1997 |
| WO | WO 1998/050871 | 11/1998 |
| WO | WO 2000/039737 A1 | 7/2000 |
| WO | WO 3098401 | 11/2003 |
| WO | WO 2007/025295 A2 | 3/2007 |
| WO | WO 2007/094772 A1 | 8/2007 |
| WO | WO 2008/092109 | 7/2008 |
| WO | WO-2008092109 A2 * | 7/2008 ............ G06F 19/328 |

OTHER PUBLICATIONS

ASHP, "Is Prescribing the Next Step in the Evolution of Pharmacy?" ASHP Intersections, May 15, 2012 (Year: 2012).*

United States Patent and Trademark Office, Advisory Action received for U.S. Appl. No. 16/832,318, dated Jan. 28, 2022, 4 pages, U.S.

United States Patent and Trademark Office, Non-Final Office Action received for U.S. Appl. No. 16/867,286, dated Feb. 22, 2022, 38 pages, U.S.

United States Patent and Trademark Office, Notice of Allowance received for U.S. Appl. No. 17/219,526, dated Feb. 3, 2022, 48 pages, U.S.

Zhu, V. et al., "Data for drugs available through low-cost prescription drug programs are available through pharmacy benefit manager and claims data," BMC Clinical Pharmacology, Jun. 22, 2012, vol. 12, No. 12., BioMed Central Ltd., UK.

Office Action for U.S. Appl. No. 14/229,043 dated Sep. 5, 2019.

Advisory Action received for U.S. Appl. No. 15/085,166, dated Jan. 29, 2021, 5 pages, US.

Google NPL (non-patent literature) Search on "pharmacy payment benefit copay NDC database", retrieved from the Internet at <https//scholar.google.com/scholar?hl=en&as_sdt-3,47&g-pharmacy+payment+benefit+copay+NDC+database> on Feb. 20, 2022 at 3:02 pm, 1 page.

Google NPL (non-patent literature) Search on "pharmacy payment benefit copay NDC database", retrieved from the Internet at <https://www.google.com/search?g=pharmacy+payment+benefit+copay+ndc+database&source=int&tbs=cdr%3A1%2Ccd_min%3A1%2F1%2F2010%2 . . . > on Feb. 20, 2022 at 3:00 pm, 2 pages.

United States Patent and Trademark Office, Advisory Action received for U.S. Appl. No. 16/792,413, dated Mar. 10, 2022, 4 pages, US.

(56) References Cited

OTHER PUBLICATIONS

United States Patent and Trademark Office, Notice of Allowance and Fee(s) Due received for U.S. Appl. No. 17/219,526, dated Mar. 22, 2022, 11 pages, US.
United States Patent and Trademark Office, Notice of Allowance and Fee(s) Due received for U.S. Appl. No. 16/551,962, dated Mar. 16, 2022, 10 pages, US.
United States Patent and Trademark Office, Notice of Allowance and Fee(s) Due received for U.S. Appl. No. 17/092,705, dated Mar. 24, 2022, 9 pages, US.
United States Patent and Trademark Office, Notice of Allowance and Fee(s) Due received for U.S. Appl. No. 16/551,962, dated Mar. 1, 2022, 14 pages, US.
Non-Final Office Action received for U.S. Appl. No. 16/551,962, dated Mar. 2, 2021, 38 pages.
Supplemental Notice of Allowability received for U.S. Appl. No. 16/180,915, dated Mar. 12, 2021, 11 pages.
Non-Final Office Action received for U.S. Appl. No. 15/085,166, dated Mar. 17, 2021, 12 pages.
Non-Final Office Action for U.S. Appl. No. 15/085,166 dated Jun. 12, 2020, 40 pages.
Non-Final Office Action for U.S. Appl. No. 16/180,915 dated Jun. 1, 2020, 40 pages.
Advisory Action for U.S. Appl. No. 14/193,294 dated Nov. 9, 2017, 3 pages.
Advisory Action for U.S. Appl. No. 15/085,166 dated Apr. 11, 2019, 4 pages.
Advisory Action for U.S. Appl. No. 15/085,166 dated Apr. 29, 2020, 3 pages.
Decision to Grant European Patent Application No. 13809457.8 dated May 18, 2017.
Extended European Search Report for European Application No. 13809457.8 dated Apr. 15, 2016, 6 pages.
Notice of Allowance and Fees(s) Due for U.S. Appl. No. 15/925,011 dated Jan. 22, 2021, 15 pages.
Office Action for U.S. Appl. No. 14/193,294 dated Sep. 19, 2018, 27 pages.
Office Action for U.S. Appl. No. 15/085,166 dated Jun. 29, 2018, 19 pages.
Office Action for U.S. Appl. No. 15/422,184 dated Aug. 27, 2019, 16 pages.
Office Action for U.S. Appl. No. 15/422,184 dated Feb. 15, 2019, 15 pages.
Office Action for U.S. Appl. No. 15/422,184 dated Jan. 14, 2020, 19 pages.
Office Action for U.S. Appl. No. 15/422,184 dated Sep. 10, 2018, 13 pages.
Office Action for U.S. Appl. No. 15/925,011 dated Jun. 27, 2019, 15 pages.
Office Action for U.S. Appl. No. 15/925,011 dated Oct. 24, 2019, 19 pages.
Office Action for U.S. Appl. No. 15/925,948 dated Jun. 25, 2019, 13 pages.
Office Action for U.S. Appl. No. 15/925,948 dated Oct. 23, 2019, 18 pages.
U.S. Appl. No. 16/832,318, "Method, Apparatus, and Computer Program Product for Estimated Prescription Costs", Unpublished (filed Mar. 27, 2020), (Stacy Hopkins, Inventor), (McKesson Corporation, Assignee), pending.
U.S. Appl. No. 17/012,565, "Method, Apparatus, and Computer Program Product for Performing an Alternative Evaluation Procedure in Response to an Electronic Message," Unpublished (filing date Sep. 4, 2020), (Stacy Hopkins, et al., Inventors) (McKesson Corporation, Assignee), pending.
U.S. Appl. No. 17/092,705, "Computing System and Method for Automatically Reversing an Action Indicated by an Electronic Message," Unpublished (filing date Nov. 9, 2020), (Patrick Harris, Inventor) (McKesson Corporation, Assignee), pending.
U.S. Appl. No. 16/792,413, "Method, Apparatus and Computer Program Product for Partitioning Prescription Transaction Costs in an Electronic Prescription Transaction," Unpublished (filed Feb. 17, 2020), (Jared Burdine, Inventor) (McKesson Corporation, Assignee), pending.
U.S. Appl. No. 16/867,286, "Method, Apparatus, and Computer Program Product for Constructing Electronic Message Responses Dependent Upon Historical Information," Unpublished (filed May 5, 2020), (Jared Burdine, et al., Inventor) (McKesson Corporation, Assignee), pending.
United States Patent and Trademark Office, Advisory Action for U.S. Appl. No. 15/422,184, dated Jun. 25, 2019, 4 pages, U.S.A.
United States Patent and Trademark Office, Advisory Action for U.S. Appl. No. 15/422,184, dated Mar. 26, 2020, 5 pages, U.S.A.
United States Patent and Trademark Office, Advisory Action for U.S. Appl. No. 15/925,011, dated Jan. 31, 2020, 3 pages, U.S.A.
United States Patent and Trademark Office, Advisory Action for U.S. Appl. No. 15/925,948, dated Jan. 31, 2020, 4 pages, U.S.A.
United States Patent and Trademark Office, Notice of Allowability received for U.S. Appl. No. 15/422,184, dated Nov. 16, 2020, 2 pages, U.S.A.
United States Patent and Trademark Office, Notice of Allowance received for U.S. Appl. No. 15/422,184, dated Oct. 13, 2020, 12 pages, U.S.A.
United States Patent and Trademark Office, Notice of Allowance received for U.S. Appl. No. 15/925,948, dated Nov. 5, 2020, 22 pages, U.S.A.
United States Patent and Trademark Office, Notice of Allowance received for U.S. Appl. No. 16/043,401, dated Aug. 10, 2020, 8 pages, U.S.A.
United States Patent and Trademark Office, Office Action for U.S. Appl. No. 15/925,011, dated Apr. 8, 2020, 17 pages, U.S.A.
United States Patent and Trademark Office, Office Action for U.S. Appl. No. 15/925,948, dated Mar. 23, 2020, 29 pages, U.S.A.
United States Patent and Trademark Office, Office Action received for U.S. Appl. No. 15/422,184, dated May 18, 2020, 31 pages, U.S.A.
United States Patent and Trademark Office, Office Action received for U.S. Appl. No. 15/925,011, dated Oct. 8, 2020, 8 pages, U.S.A.
United States Patent and Trademark Office, Notice of Allowance received for U.S. Appl. No. 17/092,705, dated Dec. 23, 2021, 42 pages, U.S.
United States Patent and Trademark Office, Non-Final Office Action received for U.S. Appl. No. 15/085,166, dated Jan. 10, 2022, 12 pages, U.S.
United States Patent and Trademark Office, Final Office Action received for U.S. Appl. No. 16/792,413, dated Jan. 10, 2022, 80 pages, U.S.
United States Patent and Trademark Office, Notice of Allowance for U.S. Appl. No. 14/181,011, dated Feb. 13, 2019, 10 pages.
United States Patent and Trademark Office, Notice of Allowance for U.S. Appl. No. 14/643,468, dated Oct. 24, 2018, 22 pages.
Almaro, Moshe; "Recovery and Reuse of Unused Prescription Drugs" MIT What Matters: Aug. 2005.
American Society of Health-System Pharmacists (ASHP), "Is Prescribing the Next Step in the Evolution of Pharmacy?" May 15, 2012.
Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.
Anonymous, Medic; On-line Goes In-House, Chain Store Age Executive, Jan. 1987, vol. 63, Issue 1, USA; Abstract only.
Anonymous, Pharmacy Industry Leaders Launch Firm to Supply Real-Time Data, PR Newswire, Jul. 30, 2001, p. 1, New York, NY, USA.
Anonymous, TechRx Announces Successful Beta Deployment of T-Rex. PR Newswire. May 13, 2002.
Consalvo, Bob; "City of Bosont in the City Council" heating notice, Dec. 6, 2006.
Coping with Information Overload. The News Source for Healthcare Information Technology {Online} Nov. 2004. URL: http://www.awarix.com.

(56) References Cited

OTHER PUBLICATIONS

Final Office Action for U.S. Appl. No. 12/140,015 dated Jan. 31, 2011.
Final Office Action for U.S. Appl. No. 12/415,062 dated Oct. 6, 2011.
Final Office Action for U.S. Appl. No. 12/555,589 dated Apr. 11, 2012.
Final Office Action for U.S. Appl. No. 12/560,071 dated Aug. 28, 2015.
FinalOffice Action for U.S. Appl. No. 12/560,071 dated Nov. 8, 2012.
Final Office Action for U.S. Appl. No. 12/570,982 dated Apr. 11, 2014.
Final Office Action for U.S. Appl. No. 12/570,982 dated Aug. 28, 2015.
Final Office Action for U.S. Appl. No. 12/570,982 dated Jan. 17, 2013.
FinalOffice Action for U.S. Appl. No. 12/730,015 dated Aug. 14, 2012.
Final Office Action for U.S. Appl. No. 12/978,898 dated May 16, 2013.
Final Office Action for U.S. Appl. No. 13/721,890 dated Jun. 24, 2015.
Final Office Action for U.S. Appl. No. 13/721,890 dated Nov. 25, 2016.
Final Office Action for U.S. Appl. No. 13/782,909 dated May 31, 2016.
Final Office Action for U.S. Appl. No. 13/782,909 dated Oct. 6, 2015.
Final Office Action for U.S. Appl. No. 13/804,175 dated Oct. 6, 2015.
Final Office Action for U.S. Appl. No. 14/090,113 dated Jan. 6, 2016.
Final Office Action for U.S. Appl. No. 14/090,122 dated Apr. 22, 2016.
Final Office Action for U.S. Appl. No. 14/193,294 dated May 2, 2016.
Final Office Action for U.S. Appl. No. 14/218,326 dated Jun. 30, 2016.
Kaplan et al., "Let the Needles Do the Talking! Evaluating the New Haven Needle Exchange." Interfaces 23:1, Jan.-Feb. 1993 (pp. 7-26).
Lamb, J., New Era of Electronic Medicine Management; E-PRESCRIPTIONS, Britain's Traditionally Cautious National Health Service is Starting Trials for Online Prescription, will the Aim of Cutting Costs, Finance Times, London, Feb. 21, 2001, p. 6, London, United Kingdom.
Letter Restarting Period for Response for U.S. Appl. No. 13/721,890 dated Jan. 14, 2015.
Marie Chisholm et al. "Pharmaceutical Manufacturer Assistance Program." Arch Intern Med. vol. 162, Apr. 8, 2002.
Non-Anal Office Action for U.S. Appl. No. 13/721,890 dated Jun. 14, 2016.
Non-Final Office Action for U.S. Appl. No. 12/560,071 daed Jun. 21, 2012.
Non-Final Office Action for U.S. Appl. No. 12/570,982 dated Jun. 20, 2012.
Non-Final Office Action for U.S. Appl. No. 14/193,294 dated Feb. 21, 2017.
Non-final Office Action for U.S. Appl. No. 12/140,015 dated Oct. 8, 2010.
Non-final Office Action for U.S. Appl. No. 12/189,650 dated Jan. 22, 2010.
Non-final Office Action for U.S. Appl. No. 12/189,654 dated Jan. 22, 2010.
Non-Final Office Action for U.S. Appl. No. 12/415,062 dated Mar. 30, 2011.
Non-Final Office Action for U.S. Appl. No. 12/555,589 dated Dec. 9, 2011.
Non-Final Office Action for U.S. Appl. No. 12/560,071 dated Sep. 23, 2014.
Non-Final Office Action for U.S. Appl. No. 12/570,982 dated Sep. 12, 2013.
Non-Final Office Action for U.S. Appl. No. 12/730,015 dated Mar. 6, 2012.
Non-Final Office Action for U.S. Appl. No. 12/956,411 dated Jan. 24, 2011.
Non-Final Office Action for U.S. Appl. No. 12/978,898 dated Feb. 6, 2013.
Non-Final Office Action for U.S. Appl. No. 12/982,395 dated Dec. 11, 2012.
Non-Final Office Action for U.S. Appl. No. 13/721,890 dated Jan. 9, 2015.
Non-final Office Action for U.S. Appl. No. 13/782,909 dated Feb. 11, 2016.
Notice of Allowance for U.S. Appl. No. 11/674,069 dated Jul. 19, 2010.
Notice of Allowance for U.S. Appl. No. 12/140,015 dated Jun. 10, 2011.
Notice of Allowance for U.S. Appl. No. 12/165,221 dated Nov. 16, 2010.
Notice of Allowance for U.S. Appl. No. 12/189,650 dated Aug. 13, 2010.
Notice of Allowance for U.S. Appl. No. 12/956,411 dated Aug. 5, 2011.
Notice of Allowance for U.S. Appl. No. 12/982,395 dated Apr. 24, 2013.
Notice of Allowance for U.S. Appl. No. 14/181,011 dated May 15, 2019.
Office Action for U.S. Appl. No. 12/570,982 dated Apr. 8, 2015.
Office Action for U.S. Appl. No. 14/181,011 dated Feb. 29, 2016.
Office Action for U.S. Appl. No. 14/181,011 dated Mar. 20, 2017.
Office Action for U.S. Appl. No. 14/181,011 dated Oct. 20, 2016.
Office Action for U.S. Appl. No. 14/181,011 dated Sep. 12, 2017.
Office Action for U.S. Appl. No. 14/193,294 dated Aug. 4, 2017, 31 pages.
Office Action for U.S. Appl. No. 14/193,294 dated Mar. 22, 2018, 28 pages.
Office Action for U.S. Appl. No. 14/229,043 dated Feb. 27, 2019.
Office Action for U.S. Appl. No. 14/229,043 dated Jul. 24, 2017.
Office Action for U.S. Appl. No. 14/229,043 dated Sep. 14, 2018.
Ollice Action for U.S. Appl. No. 14/643,468 dated Mar. 8, 2018.
Office Action for U.S. Appl. No. 15/085,166 dated Dec. 27, 2018.
Ollice Action for U.S. Appl. No. 13/782,909 dated Jun. 25, 2015.
Office Action for U.S. Appl. No. 13/804,175 dated Mar. 13, 2015.
Office Action for U.S. Appl. No. 14/090,122 dated Oct. 21, 2016.
Office Action for U.S. Appl. No. 14/090,122 dated Sep. 11, 2015.
Office Action for U.S. Appl. No. 14/090,113 dated Jun. 18, 2015.
Office Action for U.S. Appl. No. 14/1218,326 dated Dec. 1, 2015.
Office Action for U.S. Appl. No. 14/193,294 dated Dec. 17, 2015.
Opar, Alisa; "Rising drug costs prompt new uses for old pills." Nature Medicine, 1211333 (2006).
"Pharmacy Reject Cedes" NCPDP.
Sampson, R.J., Taking Control of Health Care Costs, Best's Review—Life Health Insurance Edition, Nov. 1983, vol. 84, Issue 7, USA; Abstract only.
Siller et al., "Safe Disposal of Unused Controlled Substances" Avalere Health 2008.
"St. Vincent's first to use Birmingham startup's information system." The Birmingham News [Online] Apr. 11, 2005. URL: http://www.awarix.com.
"St. Vincent's is Digital Flagship" D. Lockridge; Birmingham Medical News [Online] Sep. 2005.
Strom, Stephanie; "Old Pills Finding New Medicine Cabinets" NY Times, May 18, 2005.
Subnotebooks,Phones, and More. St. Vincent's Gets on Track. Mobile Health Data [Online], Nov. 19, 2004. URL:http://www.awarix.com.
"Two automatic identification technology, neither new in the sense if being recent developments . . . " Patient Safety & Quality Healthcare [Online] Aug. 2005 URL: http://www_awarix.com.

(56) References Cited

OTHER PUBLICATIONS

Wisconsin Physicians Service (WPS) Insurance Corporation, "How to Read Your Explanation of Benefit s Chart," Jun. 16, 2012.
www.ncoil.org/news/DragCards2.doc dated Apr. 2002.
U.S. Appl. No. 14/229,043, filed Mar. 28, 2014, Pinsonneault.
U.S. Appl. No. 15/084,034, filed Mar. 29, 2016, Geone et al.
U.S. Appl. No. 15/085,166, filed Mar. 30, 2016, Kaye et al.
U.S. Appl. No. 16/180,915, filed Nov. 5, 2018, Pinsonneault.
Advisory Action for U.S. Appl. No. 15/137,371 dated Feb. 25, 2019, 5 pages.
Advisory Action for U.S. Appl. No. 15/427,746 dated Jul. 2, 2019, 4 pages.
Examiner's Answer for U.S. Appl. No. 14/145,027 dated Sep. 7, 2016, 28 pages.
Final Office Action for U.S. Appl. No. 13/827,676 dated Jul. 13, 2015.
Final Office Action for U.S. Appl. No. 14/145,027 dated Nov. 19, 2015.
Final Office Action for U.S. Appl. No. 15/137,371 dated Nov. 28, 2018, 24 pages.
Final Office Action for U.S. Appl. No. 15/427,746 dated Apr. 15, 2019, 10 pages.
Lamb, J., New Era of Electronic Medicine Management: E-PRESCRIPTIONS, Britain's Traditionally Cautious National Health Service is Starting Trials for Online Prescription, with the Aim of Cutting Costs. Financial Times, London, Feb. 21, 2001, p. 6, London, United Kingdom.
Non-Final Office Action for U.S. Appl. No. 12/388,956 dated Feb. 3, 2011.
Non-Final Office Action for U.S. Appl. No. 13/827,676 dated Dec. 26, 2014.
Non-final Office Action for U.S. Appl. No. 13/827,676 dated Dec. 30, 2015.
Non-Final Office Action for U.S. Appl. No. 14/145,027 dated Mar. 23, 2015.
Non-Final Office Action for U.S. Appl. No. 15/137,371 dated May 29, 2018, 33 pages.
Non-Final Office Action for U.S. Appl. No. 15/427,746 dated Oct. 18, 2018, 9 pages.
Non-Final Office Action for U.S. Appl. No. 16/819,258 dated Sep. 4, 2020, 13 pages.
Notice of Allowance for U.S. Appl. No. 12/388,956 dated Jun. 14, 2011.
Notice of Allowance for U.S. Appl. No. 15/137,371 dated May 2, 2019, 30 pages.
Notice of Allowance for U.S. Appl. No. 15/427,746 dated Dec. 4, 2019, 15 pages.
Notice of Allowance for U.S. Appl. No. 15/427,746 dated Jul. 31, 2019, 13 pages.
PTAB Decision on Appeal for U.S. Appl. No. 14/145,027 dated May 31, 2018, 12 pages.
PTAB Decision on Request for Rehearing for U.S. Appl. No. 14/145,027 dated Aug. 30, 2018, 10 pages.
U.S. Notice of Allowance received for U.S. Appl. No. 16/819,258, dated Nov. 16, 2020, 8 pages, U.S.
Scientific and Technical Information Center, Report of Information from Dialog (NPL (non-patent literature) Search Results, Abstracts only), dated Nov. 1, 2021, (Year: 2021), 9 pages.
United States Patent and Trademark Office, Advisory Action received for U.S. Appl. No. 16/453,509, dated Oct. 12, 2021, 5 pages, U.S.
United States Patent and Trademark Office, Final Office Action received for U.S. Appl. No. 16/551,962, dated Nov. 4, 2021, 32 pages, U.S.
United States Patent and Trademark Office, Final Office Action received for U.S. Appl. No. 16/832,318, dated Nov. 3, 2021, 22 pages, U.S.
Office Action for U.S. Appl. No. 15/085,166 dated Mar. 3, 2020.
CMS Updates Drug Dashboards with Prescription Drug Pricing and Spending Data, Data, Medicare Part D, Prescription drugs (Mar. 14, 2019).
How to Estimate the Cost of a Prescription. Pam Olson, Sr. Client Services Executive, Navitus Health Solutions (Year: 2015).
United States Patent and Trademark Office, Final Office Action received for U.S. Appl. No. 16/453,509, dated Aug. 18, 2021, 16 pages, U.S.
United States Patent and Trademark Office, Non-Final Office Action received for U.S. Appl. No. 16/792,413, dated Aug. 5, 2021, 32 pages, U.S.
Final Office Action for U.S. Appl. No. 15/085,166, dated Dec. 4, 2020, 12 pages.
Notice of Allowance for U.S. Appl. No. 16/180,915 dated Dec. 11, 2020, 23 pages.
Non-Final Office Action received for U.S. Appl. No. 16/453,509 dated Mar. 26, 2021, 45 pages.
Non-Final Office Action received for U.S. Appl. No. 16/832,318 dated Apr. 23, 2021, 52 pages.
U.S. Appl. No. 14/181,011, filed Feb. 14, 2014, U.S. Pat. No. 2015/0234991.
Office Action for U.S. Appl. No. 15/085,166 dated Sep. 4, 2019 23 pages.
United States Patent and Trademark Office, Notice of Allowance received for U.S. Appl. No. 15/085,166, dated Sep. 10, 2021, 21 pages, U.S.
United States Patent and Trademark Office, Corrected Notice of Allowability received for U.S. Appl. No. 15/085,166, dated Sep. 20, 2021, 6 pages, U.S.
Chu, Kuan-Yu, et al., "Incremental analysis of the reengineering of an outpatient billing process: an empirical study in a public hospital", BMC Health Services Research, Jun. 13, 2013, vol. 13, No. 215, 8 pages, BioMed Central LTD, UK.
Google Patents Search (including Web Search History, Prior Art Search Printable History Generator) on "pharmacy payment benefit copay NDC database) (prescription) (code) (refills) (error code) country:US before filing: Dec. 31, 2013", retrieved from the Internet at <https://patents.google.com/?q=pharmacy+payment+benefit+copay+NDC+database&q=prescription&q=code&q=refills&q=error+code&country=US&before=filing:20131231> retrieved on Jun. 1, 2022, 4 pages.
Google Scholar Search (including Web Search History, Prior Art Search Printable History Generator) on "pharmacy payment benefit copay NDC database prescription . . . ", retrieved from the Internet at <https://scholar.google.com/scholar?hl=en&as_sdt=0%2C47&as_ylo=2010&as_yhi=2013&q—pharmacy+payment+benefit+copay+NDC+database+pres . . . > retrieved on Jun. 1, 2022, 3 pages.
United States Patent and Trademark Office, Non-Final Office Action received for U.S. Appl. No. 16/792,413, dated May 24, 2022, 48 pages, US.
United States Patent and Trademark Office, Non-Final Office Action received for U.S. Appl. No. 17/144,426, dated May 31, 2022, 42 pages, US.
United States Patent and Trademark Office, Non-Final Office Action received for U.S. Appl. No. 16/832,318, dated Jun. 8, 2022, 17 pages, US.
United States Patent and Trademark Office, Notice of Allowance received for U.S. Appl. No. 17/092,705, dated May 31, 2022, 9 pages, US.
United States Patent and Trademark Office, Notice of Allowance received for U.S. Appl. No. 17/219,526, dated Jun. 2, 2022, 8 pages, US.
United States Patent and Trademark Office, Notice of Allowance received for U.S. Appl. No. 16/551,962, dated Jun. 8, 2022, 11 pages, US.
United States Patent and Trademark Office, Notice of Allowance received for U.S. Appl. No. 15/085,166, dated Jun. 15, 2022, 18 pages, U.S.
United States Patent and Trademark Office, Final Office Action received for U.S. Appl. No. 17/012,565, dated Jul. 25, 2022, 43 pages, U.S.
United States Patent and Trademark Office, Non-Final Office Action received for U.S. Appl. No. 17,012,565, dated Apr. 12, 2022, 19 pages, U.S.A.

(56) References Cited

OTHER PUBLICATIONS

United States Patent and Trademark Office, Non-Final Office Action received for U.S. Appl. No. 16/453,509, dated Apr. 28, 2022, 16 pages, U.S.A.
United States Patent and Trademark Office, Non-Final Office Action received for U.S. Appl. No. 17/175,939, dated May 12, 2022, 48 pages, U.S.A.
Dubois, Robert W., "Rx Drug Costs: List Prices Versus Net Prices and The Importance Of Staying Within The Data", Health Affairs Blog, Mar. 2019, 7 pages.
Kamal, Rabah, et al., "What are the recent and forecasted trends in prescription drug spending?" Peterson-KFF Health System Tracker, Feb. 20, 2019, 19 pages, Peterson Center on Healthcare.
Cepeda, Maria Soledad, et al., "Quantification of missing prescriptions in commercial claims databases : results of a cohort study.", Pharmacoepidemiology and Drug Safety, Apr. 2017, pp. 386-392, vol. 26, Epub Jan. 25, 2017 on Wiley Online Library.
United States Patent and Trademark Office, Final Office Action received for U.S. Appl. No. 16/867,286, dated Sep. 8, 2022, 19 pages, U.S.
United States Patent and Trademark Office, Notice of Allowance received for U.S. Appl. No. 16/792,413, dated Sep. 8, 2022, 18 pages, U.S.
United States Patent and Trademark Office, Notice of Allowance received for U.S. Appl. No. 17/012,565, dated Sep. 21, 2022, 11 pages, U.S.
United States Patent and Trademark Office, Notice of Allowance received for U.S. Appl. No. 16/453,509, dated Oct. 3, 2022, 23 pages, U.S.
United States Patent and Trademark Office, Final Office Action received for U.S. Appl. No. 17/175,939, dated Oct. 5, 2022, 30 pages, U.S.
United States Patent and Trademark Office, Nonfinal Office Action received for U.S. Appl. No. 17/162,461, dated Oct. 5, 2022, 47 pages, U.S.
United States Patent and Trademark Office, Nonfinal Office Action received for U.S. Appl. No. 17/158,118, dated Oct. 7, 2022, 46 pages, U.S.
American Hospital Association, "Drug Price Proposals", dated Apr. 2019, retrieved from the Internet at <URL: https://www.aha.org/system/files/media/file/2019/04/aha-drug-policy-recommendations_2.pdf>, 8 pages.
California Health Care Foundation, "When the Price Is Not Right: State Options on Prescription Drug Pricing", dated Jun. 2016, retrieved from the Internet at: <URL: https://www.chcf.org/wp-content/uploads/2017/12/PDF-WhenStateRxPricing.pdf>, 16 pages.
Hsee, Christopher K., et al., "General Evaluability Theory", Perspectives on Psychological Science, Jul. 2010, pp. 343-355, vol. 5, No. 4, Sage Publications, Inc. on behalf of the Association for Psychological Science retrieved from the Internet at <URL: https://www.jstor.org/stable/41613442>.
United States Patent and Trademark Office, Advisory Action received for U.S. Appl. No. 16/867,286, dated Dec. 6, 2022, 8 pages, US.
United States Patent and Trademark Office, Advisory Action received for U.S. Appl. No. 17/175,939, dated Dec. 22, 2022, 5 pages, US.
United States Patent and Trademark Office, Final Office Action received for U.S. Appl. No. 17/144,426, dated Dec. 8, 2022, 21 pages, US.
United States Patent and Trademark Office, Notice of Allowance received for U.S. Appl. No. 16/832,318, dated Dec. 8, 2022, 26 pages, US.
Van Nuys, Ph.D., Karen, et al., "Prescription Drug Copayment Coupon Landscape", Drug Pricing White Paper, USC Leonard D. Schaeffer Center for Health Policy and Economics, Feb. 7, 2018, retrieved from the Internet at <URL: https://healthpolicy.usc.edu/research/prescription-drug-copayment-coupon-landscape/>, 21 pages.

\* cited by examiner

SYSTEMS AND METHODS FOR DETERMINING AND COMMUNICATING PATIENT INCENTIVE INFORMATION TO A PRESCRIBER

CROSS-REFERENCE TO RELATED APPLICATIONS

This application is a continuation of U.S. application Ser. No. 14/181,011, filed Feb. 14, 2014, the entire contents of which are incorporated herein by reference.

TECHNICAL FIELD

Aspects of the disclosure relate generally to healthcare transactions, and more specifically to systems and methods for determining and communicating patient incentive information to a prescriber as part of a prescription benefit check for a patient.

BACKGROUND

Providing prescribers at the point of prescribing accurate copay information can be a challenge with today's healthcare provider systems as healthcare claims continue to evolve. Initially, a patient could expect to pay a single copay amount for all medications. Over time, the financial structures have grown increasingly more sophisticated (i.e. formulary tiers, deductibles, maximum benefits, etc.). Further, for some pharmacy benefit plans a patient has the ability to challenge a formulary status decision. Today, prescribers attempt to determine an accurate patient copay amount by establishing patient eligibility, including association to a specific formulary, downloading formulary information to the healthcare provider device, comparing a proposed medication to the formulary to determine alignment, or writing the prescription and waiting to see if the pharmacy calls with a request for an alternative medication. However, these solutions may be inadequate because they may not reflect the patient's actual out of pocket cost.

This problem may be further exacerbated in situations where an incentive program to reduce patient costs (i.e. patient copay amounts) exists for the medication being prescribed to the patient. An incentive program may include, but is not limited to, a coupon, voucher, rebate, discount, loyalty award, or other equivalent non-insurance benefit or the like that is provided to the patient when the medication is dispensed to the patient. Failure of a prescriber to know about or have access to benefit information for these incentive programs could result in the prescriber not being able to provide accurate copay information to the patient at the time the medication is being prescribed. This may result in the patient having their treatment adversely affected by either requesting a different medication being prescribed (because the patient believes the copay will be higher than it actually is once the incentive program is applied) or the patient choosing not to fill the prescription at all. Providing the prescriber with accurate copay information, including any incentive program information that reduces or otherwise modifies the patient copay amount will allow the prescriber to give the patient copay information that will be the same as that which the patient receives when they fill that prescription at pharmacy.

BRIEF DESCRIPTION OF THE DRAWINGS

Reference will now be made to the accompanying drawings, which are not necessarily drawn to scale, and wherein.

DETAILED DESCRIPTION OF EXEMPLARY EMBODIMENTS

Figure 1A:
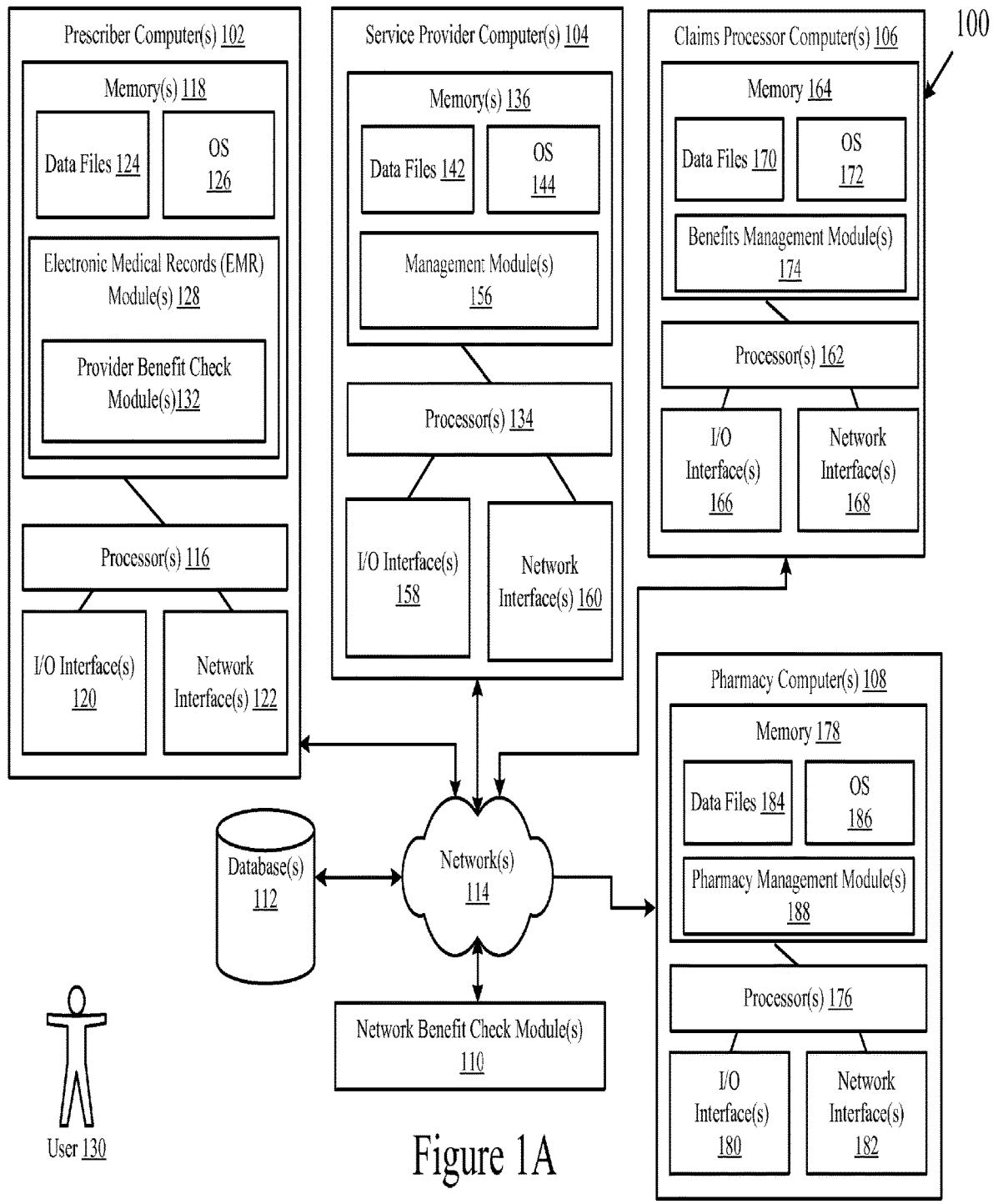
FIGS. 1A and 1B illustrate an example system for, among other things, determining and communicating accurate patient copay information to the prescriber during a prescription process, according to one exemplary embodiment.

Exemplary embodiments will now be described more fully hereinafter with reference to the accompanying drawings, in which exemplary embodiments are shown. The concepts disclosed herein may, however, be embodied in many different forms and should not be construed as limited to the exemplary embodiments set forth herein; rather, these embodiments are provided so that this disclosure will be thorough and complete, and will fully convey the scope of the concepts to those skilled in the art. Like numbers refer to like, but not necessarily the same or identical, elements throughout.

Exemplary embodiments described herein include systems and methods for determining and communicating patient copay and incentive program information to the prescriber at the point of selecting a patient medication treatment. The determination and communication of patient copay and incentive program information may be based at least in part on pharmacy information received in a previously submitted transaction. In certain example implementations, a prescription benefit check transaction may be communicated from a healthcare provider, such as a doctor, hospital employee, physician's assistant, nurse, or other prescriber of medication. In one example, the prescription benefit check transaction may include pharmacy benefit information captured by a healthcare provider (e.g., a doctor, hospital employee, physician's assistant, or other prescriber of medication) during a patient visit. For example, the healthcare provider may receive, request, or otherwise obtain the patient's name, date of birth, gender, identification of a preferred pharmacy of the patient or benefits provider (e.g., insurance company, pharmacy benefits manager (PBM), government-funded healthcare insurance program, such as Medicare, Medicaid or other government healthcare insurance program) to use for filling the prescription, and benefits provider identification (e.g., insurance company, PBM, government-funded healthcare insurance program, such as Medicare, Medicaid or other government healthcare insurance program).

Additionally, the prescription benefit check transaction may include a medication identifier. For example, the prescription benefit check transaction may be communicated in real time or near real time to a service provider computer associated with a service provider, such as a switch. The service provider computer may determine a transaction type identified in the prescription benefit check transaction. In certain example embodiments, the billing request transaction type may include, without limitation, a pharmacy billing request (i.e., the billing designation "R"), a prescriber billing request (i.e., a billing designation "P"), a predetermination of benefits request (i.e., a billing designation "D"), or an X12 270 eligibility inquiry transaction. Additionally, the service provider computer may determine the prescription benefit check transaction destination. For example, the processing of the prescription benefit check transaction may include, without limitation, a determination of (i) whether the included pharmacy identification associated with the patient's preferred pharmacy is a contracted pharmacy (e.g., a pharmacy or pharmacy chain for which additional services such as determining and providing patient copay information and determining and providing incentive program information or modifying the patient copay information based on the incentive(s) received by the patient for the medication prescribed based on the determined incentive program information); (ii) whether all of the required patient and/or prescriber information is included in the prescription benefit check transaction; and/or (iii) whether the benefits provider identification included in the prescription benefit check transaction is a benefits provider identification identifier of a supported benefits provider. The service provider computer may also access stored pharmacy information captured in a previously submitted healthcare claim or billing transaction received by the service provider computer from the pharmacy and determined to meet one or more predetermined pharmacy and medication qualifiers.

The service provider computer may communicate the prescription benefit check transaction to a claims processor computer for the determined benefits provider as a billing request transaction. The claims processor computer for the benefits provider may adjudicate the billing request transaction and communicate an adjudicated billing response to the service provider computer. The adjudicated billing response may include a status indicator to indicate whether the billing request transaction is paid or rejected as well as a field indicating the patient copay amount. The adjudicated billing response may also include a text field or coded field for providing a rejection reason. In addition, the adjudicated billing response may use the text field or another text field for providing information identifying the source and amount of any incentive (e.g., coupon, voucher, discount, rebate, loyalty award or the like) that the patient will receive for filling the prescription at the pharmacy/pharmacy chain identified in the billing request transaction. Upon receipt of the adjudicated billing response, the service provider computer may capture predetermined portions of the adjudicated billing response and deliver it to the healthcare provider computer/device (healthcare provider computer). Following, or prior to delivery of the adjudicated billing response to the healthcare provider computer/device, the service provider computer may generate a reversal of the billing request transaction (reversal transaction) of corresponding transaction type and communicate it to the claims processor computer for the benefits provider. In examples where the reversal transaction is transmitted after delivery of the adjudicated billing response to the healthcare provider computer, the transmittal of the reversal transaction may occur after a suitable predetermined waiting period. For example, the suitable time interval may include, but is not limited to, any amount between 1-3600 seconds, such as 30 seconds, 2 minutes, 5 minutes, or the like. The claims processor computer for the benefits provider may adjudicate the reversal transaction and communicate an adjudicated reversal transaction response to the service provider computer. The service provider computer may employ various methods and multiple attempts to ensure the reversal transaction request is processed by the claims processor computer for the benefits provider. Additionally, the service provider computer may capture pharmacy specific information from the adjudicated reversal transaction response.

System Overview

FIG. 1A illustrates an example system 100 for, among other things, determining and communicating accurate patient copay information to the prescriber during a prescription process according to one exemplary embodiment. As shown in FIG. 1A, the system 100 may include one or more prescriber computers 102, service provider computers 104, claims processor computers 106, and/or pharmacy computers 108. As desired, each of the prescriber computers 102, service provider computer 104, claims processor computers 106, and/or pharmacy computers 108 may include one or more processing devices that may be configured for accessing and reading associated computer-readable media having stored data thereon and/or computer-executable instructions for implementing various embodiments, including, but not limited to, those example embodiments of the disclosure herein.

The exemplary prescriber computer 102 is not intended to be limited to a desktop or laptop computer and can include a server computer, a mainframe computer, one or more networked computers, a desktop computer, a laptop computer, a personal computer, a digital assistant, a personal digital assistant, a smart phone, a digital tablet, an Internet appliance, an application-specific circuit, microcontroller, minicomputer, or any other processor-based device. Further, the prescriber computer 102 is not intended to be limited to physician offices alone and may otherwise be associated with any healthcare provider capable of prescribing medication, such as, for example, a prescriber (such as a doctor, hospital, urgent care center, clinic, dentist, physician's assistant, nurse, clinical pharmacist, or any other person or entity permitted to prescribe medication, etc.). While the exemplary prescriber computer 102 references a physician's office, this is for example only and is not intended to be limiting in any manner.

Additionally, in one or more example embodiments of the disclosure, the service provider computer 104 may include or otherwise be communicably coupled with a network benefit check module 110 or benefit check application. The network benefit check module 110 may include computer-executable instructions operable for facilitating the determination of accurate patient copay information, including any available incentive programs (e.g., coupon, voucher, discount, rebate, loyalty award or the like) during a prescription writing process. For example, the network benefit check module 110 may receive or facilitate receipt of a prescription benefit check request transaction (i.e., a predetermination of benefits transaction, healthcare claim transaction, prescription claim or billing request, healthcare order transaction, X12 270 eligibility inquiry transaction, or e-prescription transaction (i.e., electronic prescription order transaction, e-script, or e-prescription)). The network benefit check module 110 may store or facilitate storage of information included in the prescription benefit check request transaction in one or more suitable databases and/or data storage devices 112. For example, the network benefit check module 110 may store or facilitate the storage of information including, but not limited to, patient information (i.e., a unique patient identifier (e.g., patient social security number, a subset of the patient social security number, health insurance claim number (HICN), cardholder ID, etc.), patient name, patient gender, patient date of birth), a claims processor identifier (e.g., Banking Identification Number (BIN Number), BIN Number and Processor Control Number (PCN), or BIN Number and Group ID), a benefits provider name associated with the claims processor computer 106, date of service, software and/or vendor certification identification, pharmacy identification qualifier, pharmacy identifier (e.g., store and/or chain name, national provider identifier (NPI) number, NCPDP Provider ID, ePrescribing identifier and/or a provider identification issued by the Drug Enforcement Agency (DEA), prescriber name, and prescriber ZIP code or other postal zone identifier for a prescription or the like), and medication information (i.e., medication name(s), National Drug Code (NDC) numbers, RxNorm medication identifiers, and the like). Further, the network benefit check module 110 may store or facilitate storage of additional medication information including, but not limited to, total number of medications, and quantity of each medication to be dispensed.

In addition to receiving and storing information, the network benefit check module 110 may be further operable to access and/or be in communication with one or more suitable databases and/or data storage devices 112. In one non-limiting example, the benefit check module 110 may also access, such as via the database 112, usual and customary pricing information for a particular pharmacy and captured from transactions previously submitted from pharmacy computers 108 associated with and/or located at that particular pharmacy and received in the form of healthcare claim transactions or pharmacy billing transactions. The network benefit check module 110 may concatenate the obtained usual and customary pricing information for the particular pharmacy identified in the prescription benefit check transaction with the received and stored data from the one or more healthcare claim transactions or prescription billing transactions previously received from that pharmacy for use in determining accurate patient copay information to the prescriber during a prescription process. In addition, the benefit check module 110 or another portion of the service provider computer 104 may also access, such as via the database 112 or one or more other local or remote databases (such as an incentive database or medication manufacturer database) incentive program information (e.g., coupon, voucher, discount, rebate, loyalty award or the like) for the medication identified in the prescription benefit check transaction and may modify the patient copay amount based on the received or identified incentive program information for the identified medication prior to sending the patient copay information to the prescriber computer 102 via an adjudicated billing response.

Generally, network devices and systems, including one or more prescriber computers 102, service provider computers 104, claims processor computers 106, and/or pharmacy computers 108, may include or otherwise be associated with suitable hardware and/or software for transmitting and receiving data and/or computer-executable instructions over one or more communication links or networks. These network devices and systems may also include any number of processors for processing data and executing computer-executable instructions, as well as other internal and peripheral components currently known in the art or which may be developed in the future. Further, these network devices and systems may include or be in communication with any number of suitable memory devices operable to store data and/or computer-executable instructions. By executing computer-executable instructions, each of the network devices may form a special-purpose computer or particular machine. As used herein, the term "computer-readable medium" describes any medium for storing computer-executable instructions.

As shown in FIG. 1A, the one or more prescriber computers 102, service provider computers 104, claims processor computers 106, and/or pharmacy computers 108 may be in communication with each other via one or more networks, such as network 114, which may include one or more independent and/or shared private and/or public networks including the Internet or a publicly switched telephone network. In other example embodiments, one or more components of the system 100 may communicate via direct connections and/or communication links. Each of these components—the prescriber computer 102, service provider computer 104, claims processor computer 106, pharmacy computer 108, and the network 114—will now be discussed in further detail. Although the components are generally discussed as singular components, as may be implemented in various example embodiments, in alternative exemplary embodiments each component may include any number of suitable computers and/or other components.

With continued reference to FIG. 1A, one or more prescriber computers 102 may be associated with any healthcare provider capable of prescribing medication, such as, for example, a prescriber (such as a doctor, hospital, urgent care center, clinic, dentist, physician's assistant, nurse, clinical pharmacist, etc.) A prescriber computer 102 may be any suitable processor-driven device that facilitates the processing of healthcare transactions (i.e., a predetermination of benefits transaction, healthcare claim transaction, prescription claim or billing request, healthcare order transaction, X12 270 eligibility inquiry transaction, or e-prescription transaction (i.e., electronic prescription order transaction, e-script, or e-prescription)) made by or on behalf of any healthcare provider capable of prescribing medication, such as, for example, a prescriber (such as a doctor, hospital, urgent care center, clinic, dentist, physician's assistant, nurse, clinical pharmacist, etc.) for a patient prescription, the communication of healthcare transactions to the service provider computer 104, and/or the receipt, processing, and display of responses received from the service provider computer 104. For example, the prescriber device 102 may be a computing device that includes any number of server computers, mainframe computers, networked computers, desktop computers, personal computers, mobile devices, smartphones, digital assistants, personal digital assistants, smart phone devices, tablet devices, Internet appliances, application-specific integrated circuits, microcontrollers, minicomputers, and/or any other processor-based devices. The prescriber computer 102 having computer-executable instructions stored thereon may form a special-purpose computer or other particular machine that is operable to facilitate the processing of transactions/requests for healthcare information made by or on behalf of a healthcare provider and the communication of requested healthcare information and other healthcare transactions to the service provider computer 104. Additionally, in certain example embodiments, the operations and/or control of the prescriber computer 102 may be distributed among several processing components. In addition to including one or more processors 116, the prescriber computer 102 may further include one or more memory devices (or memory) 118, one or more input/output ("I/O") interfaces 120, and one or more network interfaces 122. The memory devices 116 may be any suitable memory devices, for example, caches, read-only memory devices, random access memory devices, magnetic storage devices, removable storage devices, etc. The memory devices 118 may store data, executable instructions, and/or various program modules utilized by the prescriber computer 102, for example, data files 124, an operating system ("OS") 126, and/or an electronic medical records (EMR) module 128.

The OS 126 may be a suitable software module that controls the general operation of the prescriber computer 102. The OS 126 may also facilitate the execution of other software modules by the one or more processors 116, for example, the EMR module 128. The OS 126 may be any operating system known in the art or which may be developed in the future including, but not limited to, Microsoft Windows®, Apple OSX™, Apple iOS™, Google Android™, Linux, Unix, or a mainframe operating system.

The EMR module 128 may be a software application(s), including, but not limited to, a dedicated program: for making diagnoses; for determining prescriptions, over-the-counter medications, products or other healthcare services associated with one or more diagnoses; for creating healthcare transactions (i.e., a predetermination of benefits transaction, healthcare claim transaction, prescription claim or billing request, healthcare order transaction, X12 270 eligibility inquiry transaction, or e-prescription transaction (i.e., electronic prescription order transaction, e-script, or e-prescription)) or for reading and/or updating medical records, as well as interacting with the service provider computer 104. For example, a user 130, such as a healthcare system employee, may utilize the EMR module 128 during a patient visit, for capturing the patient's personal information, preferred pharmacy information, and/or pharmacy benefit information. Furthermore, the prescriber device 102 may utilize the EMR module 128 to retrieve or otherwise receive data, messages, or responses from the service provider computer 104 and/or other components of the system 100.

During the prescription process, the EMR module 128 may engage the provider benefit check module 132 to communicate prescription information to the service provider computer 104 for use in determining accurate patient copay information, incentive program information, and displaying the retrieved copay information (or adjusted copay information based on received incentive program information) at a display communicably coupled to the prescriber computer 102. The provider benefit check module 132 may gather all the required and available optional data including, but not limited to, the medication information (e.g., total number of medications, medication name(s), medication identifiers (e.g., NDC number(s), RxNorm medication identifiers), etc.), patient information (i.e., patient name, gender, and date of birth), and prescriber identification number (i.e., prescriber ID (e.g., NPI number and/or a prescriber identification issued by the DEA), prescriber name, and prescriber ZIP code or other postal zone identifier, pharmacy identifier (e.g., pharmacy name, NPI number, an NCPDP Provider ID, an ePrescribing identifier, etc.) and pharmacy zip code or other postal code identifier. Following the information collection, the provider benefit check module 132 or another portion of the prescriber computer 102 formats one or more prescription transactions (i.e., a predetermination of benefits transaction, healthcare claim transaction, prescription claim or billing request, healthcare order transaction, or X12 270 eligibility inquiry transaction, or e-prescription transaction (i.e., electronic prescription order transaction, e-script, or e-prescription)) for a patient prescription according to NCPDP standards in the agreed upon format. The one or more prescription transactions may be sent to the service provider computer 104.

The one or more I/O interfaces 120 may facilitate communication between the prescriber computer 102 and one or more input/output devices, for example, one or more user interface devices, such as a display, keypad, control panel, touch screen display, remote control, microphone, etc., that facilitate user interaction with the prescriber computer 102. For example, the one or more I/O interfaces 120 may facilitate entry of information associated with a healthcare transaction by a prescriber or a person assisting a prescriber, such as a physician, nurse practitioner, nurse, etc. The one or more network interfaces 122 may facilitate connection of the prescriber computer 102 to one or more suitable networks, for example, the network 114 illustrated in FIG. 1A. In this regard, the prescriber computer 102 may receive and/or communicate information to other network components of the system 100, such as the service provider computer 104.

With continued reference to FIG. 1A, one or more service provider computers 104 may be associated with and or located at a service provider, such as a switch. A service provider computer 104 may include, but is not limited to, any suitable processor-driven device that is configured for receiving, processing, and fulfilling healthcare transactions from the prescriber computer 102 relating to patient prescription information including, but not limited to, medications, medication name(s), NDC number(s), RxNorm medication identifiers, quantity of medication to be dispensed), patient information (i.e., name, gender, date of birth), pharmacy identification information (i.e., pharmacy name, NPI number, an NCPDP Provider ID, an ePrescribing identifier, store number, pharmacy address and/or zip code or other postal zone identifier, etc.), and prescriber identification number (i.e., prescriber ID ((e.g., NPI number and/or a prescriber identification issued by the DEA), prescriber name, and prescriber ZIP code or other postal zone identifier for a prescription. Any number of prescriber computers 102, claims processor computers 106, and/or pharmacy computers 108 may be in communication with the service provider computer 104 as desired in various example embodiments.

The service provider computer 104 may include any number of special-purpose computers or other particular machines, application-specific integrated circuits, microcontrollers, personal computers, minicomputers, mainframe computers, servers, networked computers, tablets devices, smart phone devices, and/or other processor-driven devices. In certain embodiments, the operations of the service provider computer 104 may be controlled by computer-executed or computer-implemented instructions that are executed by one or more processors associated with the service provider computer 104 to form a special-purpose computer or other particular machine that is operable to facilitate the receipt, routing, and/or processing of healthcare requests or healthcare transactions. The one or more processors that control the operations of the service provider computer 104 may be incorporated into the service provider computer 104 and/or may be in communication with the service provider computer 104 via one or more suitable networks. In certain example embodiments, the operations and/or control of the service provider computer 104 may be distributed among several processing components.

Similar to the prescriber computer 102, the service provider computer 104 may include one or more processors 134, one or more memory devices 136, one or more input/output ("I/O") interfaces 138, and one or more network interfaces 140. The one or more memory devices 136 may be any suitable memory device, for example, caches, read-only memory devices, etc. The one or more memory devices 136 may store data, executable instructions, and/or various program modules utilized by the service provider computer 104, for example, data files 140 and an operating system ("OS") 144. The OS 144 may be any operating system known in the art or which may be developed in the future including, but not limited to, Microsoft Windows®, Apple OSX™, Linux, Unix, Apple iOS™, Google Android™, or a mainframe operating system. The OS 144 may be a suitable software module that controls the general operation of the service provider computer 104 and/or that facilitates the execution of other software modules.

Figure 1B:
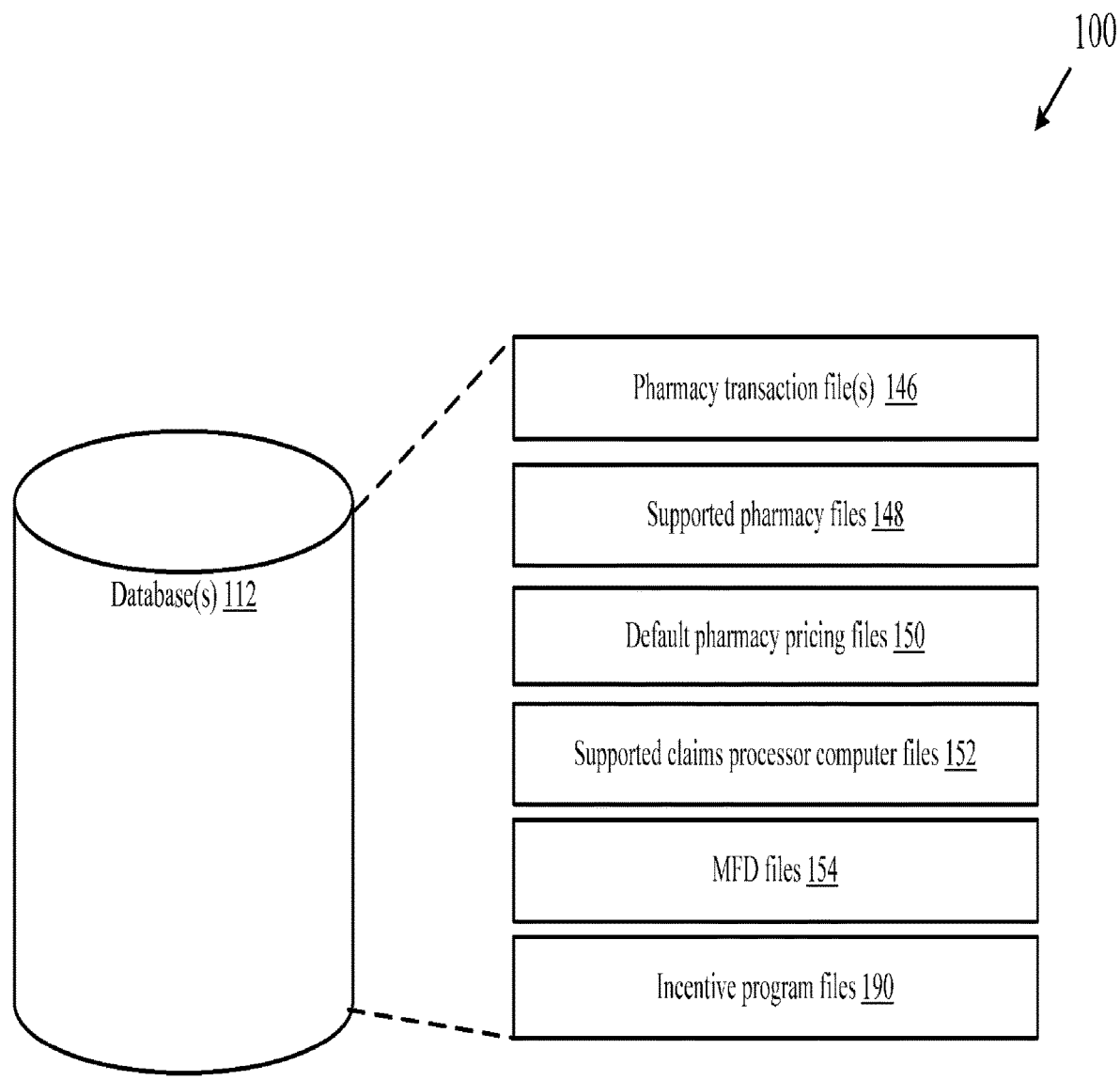

According to an example embodiment, the data files 142 may store healthcare transaction records associated with communications received from various prescriber computers 102, various claims processor computers 106, and/or various pharmacy computers 108. The data files 142 may also store any number of suitable routing tables that facilitate determining the destination of communications received from a prescriber computer 102, a claims processor computer 106, and/or a pharmacy computer 108. In certain example embodiments, the service provider computer 104 may include or otherwise communicably coupled with one or more suitable databases and/or data storage devices 112 including, but not limited to, one or more databases 112 including one or more incentive program files 190 and one or more pharmacy transaction files 146 including, one or more default supported pharmacy files 148, one or more default pharmacy pricing files 150, and one or more most frequently (MFD) dispensed files 152, as shown in FIG. 1B.

The one or more pharmacy transaction files 146 may contain, without limitation, prescription information captured from previously submitted healthcare transactions (i.e., a predetermination of benefits transaction, healthcare claim transaction, prescription claim or billing request, healthcare order transaction, X12 270 eligibility inquiry transaction, or e-prescription transaction (i.e., electronic prescription order transaction, e-script, or e-prescription)). For example, the one or more pharmacy transaction files 146 may include medication identifiers (medications, medication name(s), NDC number(s), RX Norm medication identifiers, etc.), a quantity of medication to be dispensed, and/or a cost associated with the medication.

The one or more pharmacy transaction files 146 may include one or more supported pharmacy files 148, which may contain, without limitation, one or more pharmacies supported within the healthcare system 100. The one or more supported pharmacy files 148 may include at least a pharmacy identifier (i.e., a pharmacy name, NPI number, an NCPDP Provider ID, an ePrescribing identifier, etc.), a pharmacy postal code, a pharmacy name or store number, and/or a pharmacy address. The one or more supported pharmacy files 148 may be utilized by the service provider computer 104, as described herein, during the processing of a billing transaction. The supported pharmacy files 148 may also include a designation of a default pharmacy within a specific zip/postal code. For example, the one or more supported pharmacy files 148 may include a status indicator "DF", or any other desired indicator or indication, for those pharmacies designated as default pharmacies within the associated zip/postal code.

The one or more pharmacy transaction files 146 may also include one or more default pharmacy pricing files 150, which may contain, without limitation, default price information for specific medications with a specific quantity to be dispensed. The one or more default pharmacy pricing files 150 may be organized by medication identifier (medication name(s), NDC number(s), RxNorm medication identifiers, etc.) and may include a table correlating a medication identifier with a price and a quantity to be dispensed.

Additionally, the one or more pharmacy transaction files 146 may include one or more MFD files 152, which may contain information supplied by one or more contracted pharmacies, for example, those contracted pharmacies associated with the one or more supported pharmacy files 148. The one or more MFD files 152 may include, without limitation, a table containing most frequently dispensed medications (by e.g., NDC numbers or RxNorm medication identifiers), most frequently dispensed quantities associated with the most frequently dispensed medications, and/or a most frequently dispensed days' supply associated with a most frequently dispensed medications.

The database 112 or a portion of the service provider computer 104 may also include one or more supported claims processor computer files 154. The one or more supported claims processor computer files 154 may contain, without limitation, information identifying one or more claims processor computers 106 supported within the healthcare system 100. The one or more supported claims processor computer files 154 may include at least a BIN Number or a BIN Number and Processor Control Number or a BIN Number and Group ID identifying those supported claims processor computers 106 for the supported healthcare benefits providers (e.g., insurance company, PBM, government-funded healthcare insurance program, such as Medicare, Medicaid or other government healthcare insurance program). The one or more supported claims processor computer files 154 may also include a list of one or more excluded claims processor computers 106. The list of excluded claims processor computers 106 may, for example, be organized by BIN Number or BIN Number and Processor Control Number or BIN Number and Group ID.

The database 112 or a portion of the service provider computer 104 may also include one or more incentive program information files 190. The one or more incentive program information files 190 may include information associated with one or more incentive programs covering one or more types of incentives (e.g., coupon, voucher, discount, rebate, loyalty award or the like). The information in the incentive program files 190 may include, but is not limited to, the amount or varying amounts of the incentive to be provided to, for example, reduce the copay amount for the patient, pharmaceutical marketers or manufacturers enrolled in or providing incentives, such as the name of the pharmaceutical marketer or manufacturer, the drugs or services (typically by way of an NDC number or RxNorm medication identifier) for which incentives are being provided by or for the pharmaceutical marketer or manufacturer, an identifier for the pharmaceutical marketer or manufacturer (e.g., a National Provider Identifier ("NPI")), and the methodology and/or parameters (e.g., patient age, patient sex, patient zip code, prior purchase history or lack of prior purchase history for the patient, etc.) for the incentive being provided by or for the pharmaceutical marketer or manufacturer.

The service provider computer 104 may include additional program modules for performing other processing methods described herein. Those of ordinary skill in the art will appreciate that the service provider computer 104 may include alternate and/or additional components, hardware, or software without departing from the scope of the disclosure. The management module 156 may be an Internet browser or other software, such as a dedicated program, for interacting with the prescriber computer 102, and/or the claims processor computers 106, and/or the pharmacy computer 108. Alternatively, the management module 156 may also be implemented as computer-implemented instructions of a memory of a separate computing entity or processor-based system, according to another example embodiment of the disclosure.

With continued reference to the service provider computer 104, the one or more I/O interfaces 158 may facilitate communication between the service provider computer 104 and one or more input/output devices, for example, one or more user interface devices, such as a display, keypad, control panel, touch screen display, remote control, microphone, etc., that facilitate user interaction with the service provider computer 104. The one or more network interfaces 160 may facilitate connection of the service provider computer 104 to one or more suitable networks, such as, the network 114. In this regard, the service provider computer 104 may communicate with other components of the system 100.

With continued reference to FIG. 1A, any number of claims processor computers 106 may be associated with any number of healthcare benefits providers (e.g., health insurance company, PBM, government-funded healthcare insurance program, such as Medicare, Medicaid or other government healthcare insurance program) and/or processors. Each claims processor computer 106 may be any suitable processor-driven devices, such as, but not limited to, a server computer, a personal computer, a laptop computer, a handheld computer, a smart phone, a table device, and the like. In addition to having one or more processors 162, the claims processor computer 106 may further include one or more memories 164, one or more input/output (I/O) interfaces 166, and one or more network interfaces 168. The memory 164 may store data files 170 and various program modules, such as an operating system (OS) 172 and a benefits management module 174. The I/O interface(s) 166 may facilitate communication between the processors 162 and various I/O devices, such as a keyboard, mouse, printer, microphone, speaker, monitor, bar code reader/scanner, RFID reader, and the like. The network interface(s) 170 each may take any of a number of forms, such as a network interface card, a modem, a wireless network card, and the like.

Generally, the claims processor computer 106 may facilitate the determination of benefits, coverage, and/or extent of coverage for one or more healthcare transactions (i.e., a predetermination of benefits transaction, healthcare claim transaction, prescription claim or billing request, healthcare order transaction, X12 270 eligibility inquiry transaction, or e-prescription transaction (i.e., electronic prescription order transaction, e-script, or e-prescription)). In certain example embodiments, the claims processor computer 106 may be associated with, without limitation, healthcare benefits providers (e.g., health insurance company, PBM, government-funded healthcare insurance program, such as Medicare, Medicaid or other government healthcare insurance program), another third-party payor, or a claims processor processing healthcare transactions and performing adjudication on behalf of one or more third-party payors and/or healthcare benefits providers. In one example embodiment, the claims processor computer 106 may be operated by, or otherwise included with and its operations completed by, the service provider computer 104, such as if the service provider operates the benefits computer and provides adjudication services.

The claims processor computer 106 may include the benefits management module 174. The benefits management module 174 may be an Internet browser or other software, such as a dedicated program, for interacting with the service provider computer 104 and/or the pharmacy computer 108. The benefits management module 174 may be operable to access one or more databases, including the database 112. In one example, the claims processor computer 106 may have a dedicated connection to the database 112. However, the claims processor computer 106 may also communicate with the database 112 via the network 114, or via another network.

With continued reference to FIG. 1A, any number of pharmacy computers 108 may be associated with any number of pharmacies and/or pharmacists. Each pharmacy computer 108 may be any suitable processor-driven device that facilitates receiving, processing, and/or fulfilling healthcare transactions and/or prescription transactions received from and/or transmitted to the service provider computer 104. For example, a pharmacy computer 108 may be a processor-driven device associated with (i.e., located within) a pharmacy. As desired, the pharmacy computer 108 may include any number of special-purpose computers or other particular machines, application-specific integrated circuits, microcontrollers, personal computers, minicomputers, mainframe computers, servers, and the like.

In certain example embodiments, the operations of the pharmacy computer 108 may be controlled by computer-executed or computer-implemented instructions that are executed by one or more processors associated with the pharmacy computer 108 to form a special-purpose computer or other particular machine that is operable to facilitate the receipt, processing, transmission and/or otherwise fulfillment of healthcare transactions (i.e., a predetermination of benefits transaction, healthcare claim transaction, prescription claim or billing request, healthcare order transaction, X12 270 eligibility inquiry transaction, or e-prescription transaction (i.e., electronic prescription order transaction, e-script, or e-prescription)) received from the service provider computer 104 and/or generated by and transmitted from the pharmacy computer 108 to the service provider computer 104. The one or more processors that control the operations of a pharmacy computer 108 may be incorporated into the pharmacy computer 108 and/or may be in communication with the pharmacy computer 108 via one or more suitable networks. In certain example embodiments, the operations and/or control of the pharmacy computer 108 may be distributed among several processing components.

Similar to other components of the system 100, each pharmacy computer 108 may include one or more processors 176, one or more memory devices 178, one or more I/O interfaces 180, and one or more network interfaces 182. The one or more memory devices 178 may be any suitable memory devices, for example, caches, read-only memory device, random access memory devices, magnetic storage devices, removable memory devices, etc. The one or more memory devices 178 may store data, executable instructions, and/or various program modules utilized by the pharmacy computer 108 including, but not limited to, data files 184, an OS 186, and a pharmacy management module 188. The data files 184 may include any suitable information that is utilized by the pharmacy computer 108. The OS 186 may be a suitable software module that controls the general operation of the pharmacy computer 108. The OS 186 may also facilitate the execution of other software modules by the one or more processors 176. The OS 186 may be any currently existing or future-developed operating system including, but not limited to, Microsoft Windows®, Apple OSX™, Linux, Unix, Apple iOS™, Google Android™, or a mainframe operating system.

The one or more I/O interfaces 180 may facilitate communication between the pharmacy computer 108 and one or more input/output devices, for example, one or more user interface devices, such as a display, keypad, control panel, touch screen display, remote control, microphone, etc., that facilitate user interaction with the pharmacy computer 108. The one or more network interfaces 182 may facilitate connection of the pharmacy computer 108 to one or more suitable networks, for example, the network 114. In this regard, the pharmacy 108 may receive information and generate healthcare transactions for transmission to the service provider computer 104 and/or receive healthcare transactions and/or other communications from the service provider computer 104. The pharmacy computer 108 may also communicate information associated with processing healthcare transactions to the service provider computer 104.

The pharmacy management module 188 may be a software application, including a dedicated program, for fulfilling healthcare transaction orders, reading and/or updating medical records (e.g., prescription records), facilitating patient billing, etc., as well as interacting with the service provider computer 104. For example, a pharmacist or other pharmacy employee, may utilize the pharmacy management module 188 in generating a healthcare transaction and transmitting it to the service provider computer 104 for adjudication of a prescription claim, filling a prescription, recording and/or updating a patient's medical prescription history, billing a patient, and preparing and providing a healthcare transaction request for information to the service provider computer 104. Furthermore, the pharmacy computer 108 may utilize the pharmacy management module 188 to retrieve or otherwise receive data, messages, or responses from the prescriber computer 102, the service provider computer 104 and/or other components of the system 100.

The network 114 may include any telecommunications and/or data network, whether public, private, or a combination thereof, including a local area network, a wide area network, an intranet, the Internet, intermediate handheld data transfer devices, and/or any combination thereof and may be wired and/or wireless, or any combination thereof. The network 114 may also allow for real time, offline, and/or batch transactions to be transmitted between or among the healthcare system provider 102, the service provider computer 104, the claims processor computer 106, and the pharmacy computer 108. Various methodologies as described herein, may be practiced in the context of distributed computing environments. Although the service provider computer 104 is shown for simplicity as being in communication with the prescriber computer 102, the claims processor computer 106, or the pharmacy computer 108 via one intervening network 114, it is to be understood that any other network configurations are possible. For example, intervening network 114 may include a plurality of networks, each with devices such as gateways and routers for providing connectivity between or among the components of the system 100. Instead of or in addition to the network 114, dedicated communication links may be used to connect various devices in accordance with an example embodiment. For example, the service provider computer 104 may form the basis of a network 114 that interconnects the prescriber computer 102, the service provider computer 104, the claims processor computer 106, and/or the pharmacy computer 108.

Those of ordinary skill in the art will appreciate that the system 100 shown in and described with respect to FIGS. 1A and 1B is provided by way of example only. Numerous other operating environments, system architectures, and device and network configurations are possible. Other system embodiments can include fewer or greater numbers of components and may incorporate some or all of the functionality described with respect to the system components shown in FIGS. 1A and 1B. For example, in an exemplary embodiment, the service provider computer 104 (or other computer) may be implemented as a specialized processing machine that includes hardware and/or software for performing the methods described herein. Accordingly, embodiments of the disclosure should not be construed as being limited to any particular operating environment, system architecture, or device or network configuration.

Operational Overview

Certain portions of the exemplary methods below will be described with reference to determining and communicating a benefits response message generated during an adjudication or pre-adjudication process of a healthcare transaction (i.e., a predetermination of benefits transaction, healthcare claim transaction, prescription claim or billing request, healthcare order transaction, X12 270 eligibility inquiry transaction, or e-prescription transaction (i.e., electronic prescription order transaction, e-script, or e-prescription)). While the methods described below are in reference to a healthcare transaction, each form of healthcare transaction (i.e., a predetermination of benefits transaction, healthcare claim transaction, prescription claim or billing request, healthcare order transaction, X12 270 eligibility inquiry transaction, or e-prescription transaction (i.e., electronic prescription order transaction, e-script, or e-prescription)) should be individually read as being used in the methods described below.

In addition, the exemplary methods below will be described with reference to a prescriber (such as a doctor, hospital, urgent care center, clinic, dentist, physician's assistant, nurse, clinical pharmacist, or any other person or entity permitted to prescribe medication, etc.) associated with/ using or having another use, under instruction of or in assistance for the prescriber, the prescriber computer. This reference to prescriber generally is solely for purposes of example, as any of the prescribers, such as a doctor, hospital, urgent care center, clinic, dentist, physician's assistant, nurse, clinical pharmacist, or any other person or entity permitted to prescribe medication, could be substituted for, and should each be individually read as being a part of each of these methods.

Figure 2:
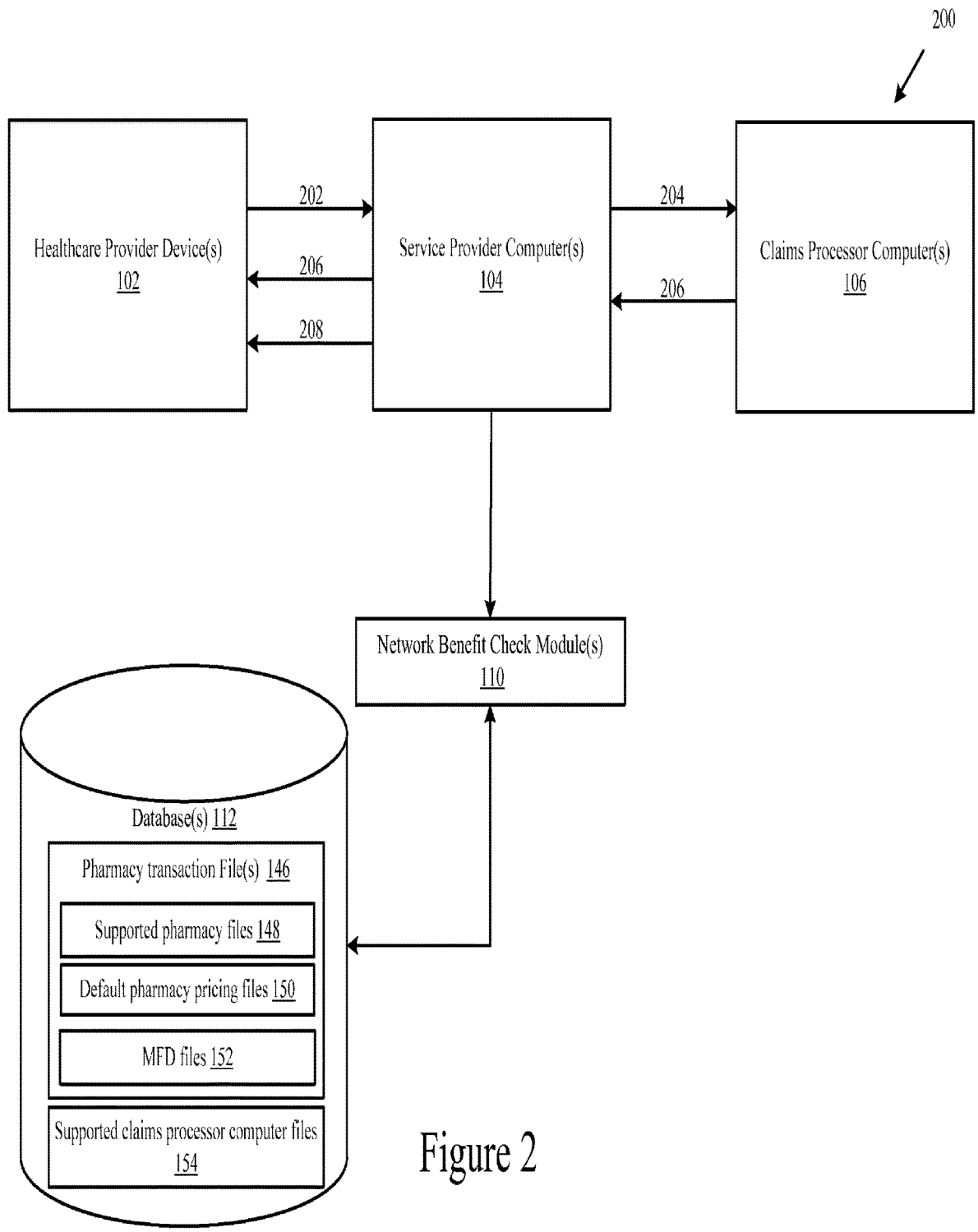
FIG. 2 is a diagram of an example data flow for facilitating receiving and communicating a prescription benefit check transaction and determining any incentive programs associated with the prescription benefit check transaction, according to one exemplary embodiment.
Figure 3A:
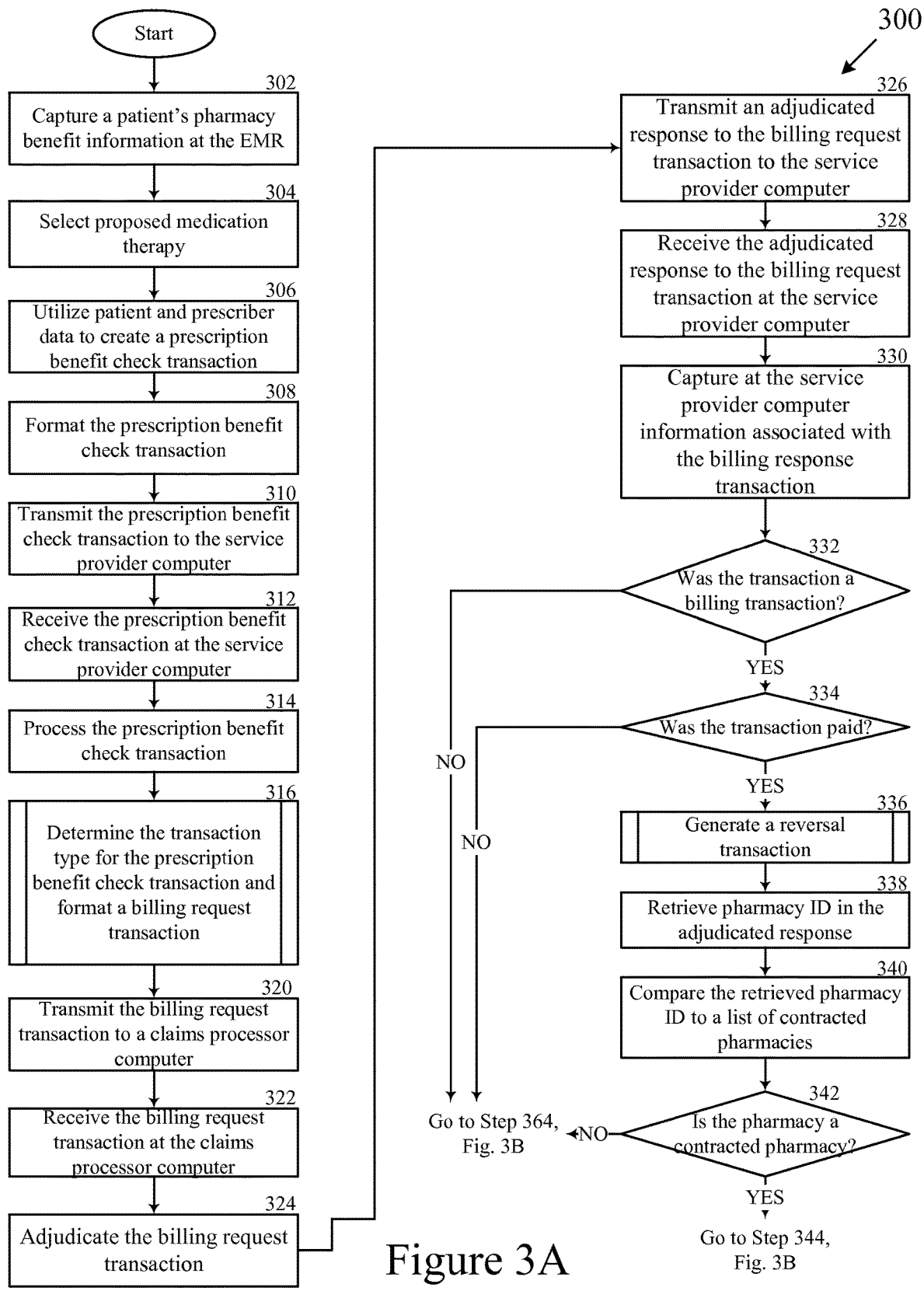
FIGS. 3A and 3B are a flow chart of an example method for receiving and communicating a prescription benefit check transaction and determining any incentive programs associated with the prescription benefit check transaction, according to one exemplary embodiment.
Figure 3B:
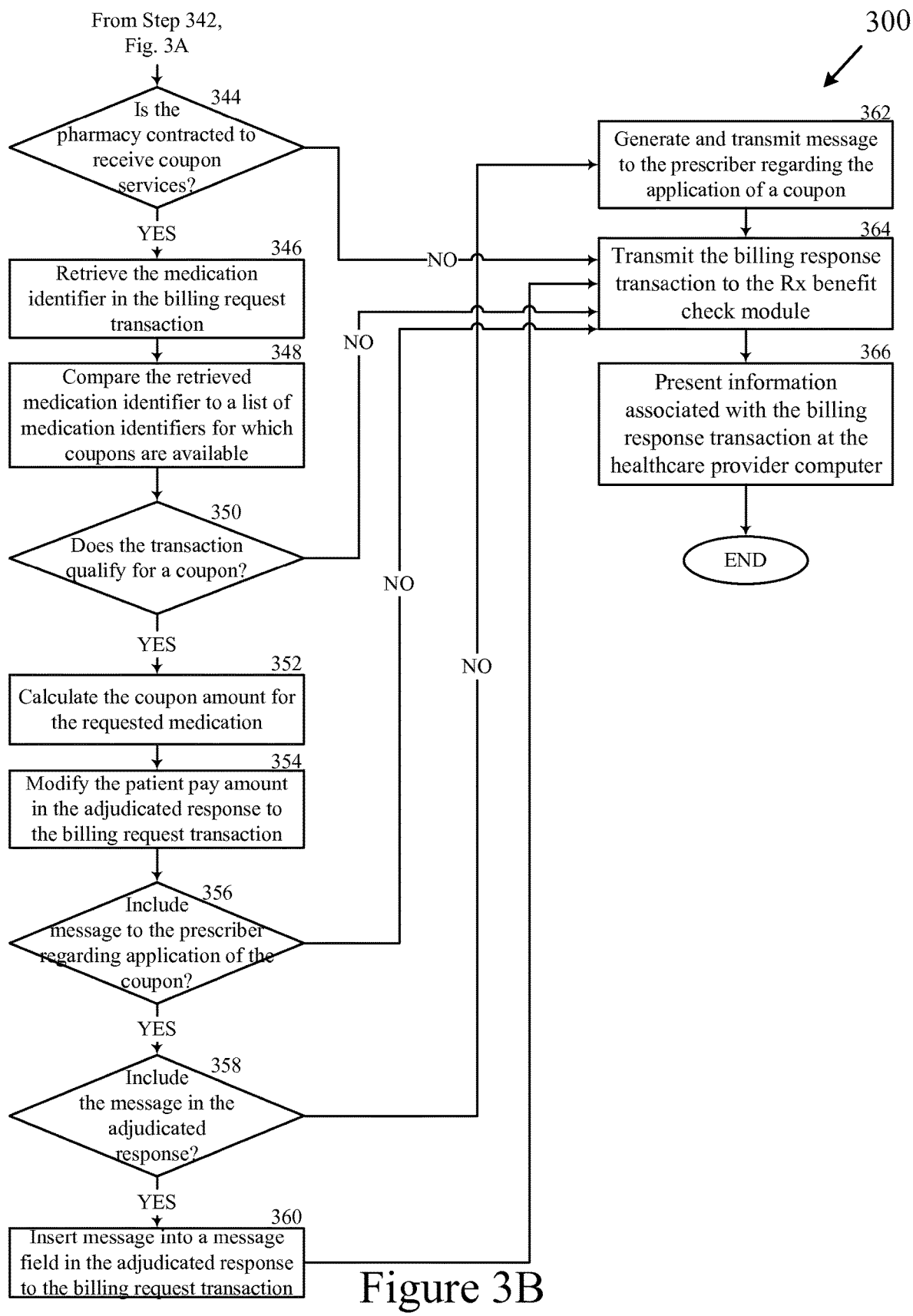

FIG. 2 is a diagram 200 of an example data flow for facilitating the receipt and communication of a prescription benefit check transaction and determining any incentive programs associated with the prescription benefit check transaction according to an example embodiment of the disclosure. FIGS. 3A and 3B illustrate an example method 300 for receiving and communicating a prescription benefit check transaction and determining any incentive programs associated with the prescription benefit check transaction according to an example embodiment of the disclosure. The block diagram 200 of FIG. 2 will be discussed in conjunction with the method of 300 of FIGS. 3A and 3B.

Referring now to FIGS. 1A-B, 2, and 3A-B the exemplary method 300 begins at the START step and continues to step 302, where a healthcare provider device, such as the prescriber computer 102, may be utilized to capture or otherwise receive or retrieve a patient's pharmacy benefit information. In one example embodiment, the prescriber computer 102 may employ an electronic medical records (EMR) module 128 to capture or otherwise receive or retrieve the patient's pharmacy benefit information. The patient's pharmacy benefit information may be captured or otherwise received or retrieved as a part of a patient visit at a doctor's office or other healthcare facility. For example, the patient's pharmacy benefit information may be captured or otherwise received or retrieved as a part of an administrative function at the point of a patient admission (i.e., a patient registration or check-in). Alternatively, the patient's pharmacy benefit information may be captured or otherwise received or retrieved at a time other than the patient visit. For example, the patient may communicate pharmacy benefit information utilizing a web-based portal from any patient desired location at a time prior to or after a patient visit. In one example, the patient's pharmacy benefit information may be found on the patient's pharmacy benefit card (i.e., insurance card or pharmacy benefits card). For example, information from the patient's pharmacy benefits card may be input into the EMR module 128 via one or more I/O interfaces 120. This information may include, without limitation, the patient's name, a unique identifier for the patient other than the patient name (e.g., social security number, partial social security number, or HICN), a BIN Number, a Processor Control Number (PCN), a Cardholder ID, a person code, a relationship code, and/or a Group ID. Additional patient information not generally included on the patient's pharmacy benefit card that may be input via the EMR module 128 and I/O interface 120 includes, without limitation, the patient's date of birth and/or a patient gender code.

In step 304, a prescriber may select a proposed medication therapy (i.e. a drug or product for the patient to receive). In one exemplary embodiment, identification for the proposed medication therapy may include a medication identifier (e.g., a National Drug Code (NDC code), RxNorm medication identifiers, and the like), a medication name, etc.). In step 306, prescription benefit check transaction 202 is generated at the prescriber computer 102. In one example embodiment, the prescription benefit check transaction 202 may be a proprietary transaction and the prescriber computer 102 may employ a provider benefit check module 132 to create the prescription benefit check transaction 202 based on information input into the prescriber computer 102 via the I/O interface 120 and/or information retrieved from one or more data storage devices, such as database 112. The prescription benefit check transaction 202 may include, without limitation, the patient pharmacy benefit information as well as prescriber information. For example, the provider benefit check module 132 may automatically gather the patient pharmacy benefit information and the prescriber information from a data storage device, such as database 112. The patient pharmacy benefit information and the prescriber information gathered by the provider benefit check module 132 may include, without limitation, the medication identifier, a total number of medications selected by the prescriber, the BIN Number, the PCN, a pharmacy ID (i.e., pharmacy name, NPI number, an NCPDP Provider ID, an ePrescribing identifier, identifying a patient's pharmacy of choice), the Cardholder ID, the Group ID, the person code, the patient's date of birth, the patient's gender code, the patient's first name, the patient's last name, a product service ID, a prescriber ID (i.e., NPI code or DEA number), a prescriber last name, and/or a prescriber postal code.

In step 308, the prescriber computer 102 may format the prescription benefit check transaction 202. In one example embodiment, the prescriber computer 102 may employ the provider benefit check module 132 to format the prescription benefit check transaction 202. For example, the provider benefit check module 132 may format the field and source of data included in the prescription benefit check transaction 202. For example:

Field: Source
Medication #: EMR module 126
Total Medications: EMR module 126
BIN Number: EMR module 126/patient pharmacy benefit card/patient profile
Processor Control Number (PCN): EMR module 126/patient pharmacy benefit card/patient profile
Pharmacy ID: EMR module 126/patient profile
Cardholder ID: EMR module 126/Patient pharmacy benefit card/patient profile
Group ID: EMR module 126/Patient pharmacy benefit card/patient profile
Person Code: EMR module 126/Patient pharmacy benefit card/patient profile
Date of Birth: EMR module 126/patient profile
Patient Gender Code: EMR module 126/patient profile
Patient First Name: EMR module 126/Patient pharmacy benefit card/patient profile
Patient Last Name: EMR module 126/Patient pharmacy benefit card/patient profile
Product Service ID EMR module 126/patient profile
Prescriber ID: EMR module 126/prescriber profile
Prescriber Last Name: EMR module 126/prescriber profile
Prescriber Postal Code: EMR module 126/prescriber profile In step 310, the prescriber computer 102 may transmit the prescription benefit check transaction 202 to the service provider computer 104. In one example, the prescriber computer 102 may employ the provider benefit check module 132 to transmit the prescription benefit check transaction 202 to the service provider computer 104 via the network 114. In step 312, the service provider computer 104 receives the prescription benefit check transaction. The service provider computer may process the prescription benefit check transaction 202 in step 314. In certain example embodiments, the service provider computer 104 may employ a network benefit check module 110 to process the prescription benefit check transaction 202. Such processing of the prescription benefit check transaction 202 may include, without limitation, a determination of (i) whether the included pharmacy ID associated with the patient's preferred pharmacy is a contracted pharmacy; (ii) whether all of the required patient and/or prescriber information is included in the prescription benefit check transaction 202; and/or (iii) whether the BIN Number or BIN Number and PCN or BIN Number and Group ID included in the prescription benefit check transaction 202 is a supported BIN Number or BIN Number and PCN or BIN Number and Group ID (i.e., is it one identifying a claims processor computer that the service provider computer 104 is contracted with to send healthcare transactions to for processing).

Processing of the prescription benefit check transaction 202 may further include a determination of a corresponding claims processor computer 106 and whether the determined claims processor computer 106 is supported by the system described in FIG. 1. Processing of the prescription benefit check transaction 202 may further include accessing one or more pharmacy transaction files 146. The one or more pharmacy transaction files 146 may include, without limitation, prescription information captured from previously submitted pharmacy billing transactions. For example, the one or more pharmacy transaction files 146 may include a medication identifier (medications, medication name(s), NDC number(s), RxNorm medication identifiers, or the like), and/or a quantity of medication to be dispensed, a cost associated with the medication (either in total or on a per unit or per dosage basis) and/or the quantity of medication to be dispensed.

In step 316, the network benefit check module 110 or another portion of the service provider computer 104 may evaluate the prescription benefit check transaction 202 to determine the transaction type of the prescription benefit check transaction 202 and format the prescription benefit check transaction 202 to a corresponding billing request transaction type 204. For example, based upon the identification of the destination claims processor computer 106, the prescription benefit check transaction 202 may be determined to be (i) a pharmacy billing request (i.e., a billing designation "R"); (ii) a prescriber billing request (i.e., a billing designation "P"); (iii) a predetermination of benefits request; (iv) an X12 270 eligibility inquiry transaction; (v) another transaction type supported by the system 100; and/or (vi) a transaction type not supported by the system 100 of FIG. 1A. Determination of certain transaction types will be discussed in greater detail with reference to FIGS. 4-6 hereinbelow. In formatting the prescription benefit check transaction 202 to a corresponding billing request transaction type 204, the service provider computer 104 may employ a network benefit check module 110 or another portion of the service provider computer 104 to format the prescription benefit check transaction 202 to a corresponding billing request transaction type 204. In certain example embodiments, the billing request transaction type may include, without limitation, a pharmacy billing request (i.e., the billing designation "R"), a prescriber billing request (i.e., a billing designation "P"), an X12 270 eligibility inquiry transaction, or a predetermination of benefits request (i.e., a billing designation "D").

In step 320, the service provider computer 104 may transmit the billing request transaction 204 to the identified claims processor computer 106 via, for example, the network 114. In step 322, the claims processor computer receives the billing request transaction from the service provider computer 104. In step 324, the claims processor computer 106 may adjudicate the billing request transaction. In one example embodiment, the adjudication may include a determination by the claims processor computer 106 of whether the billing request transaction 204 was paid or rejected. The claims processor computer 106 may transmit an adjudicated response to the billing transaction 206 to the service provider computer 104 via, for example, the network 114 in step 326. The adjudicated response to the billing transaction 206 may also include, without limitation, a transaction response type (i.e., a pharmacy billing request, a prescriber billing request, a predetermination of benefits request, an X12 271 eligibility response, etc.) and/or a transaction status indicator signifying whether the billing request transaction 204 was paid or rejected. In one example embodiment, when the billing request transaction 204 is paid, the adjudicated response to the billing transaction 206 may include a response field with a transaction status indicator of "P". If, however, the billing request transaction 204 is rejected, the response field for the adjudicated response to the billing transaction 206 may have a transaction indicator of "R".

In one example embodiment, when the response field of the adjudicated response to the billing transaction 206 includes a transaction status indicator "P", the adjudicated response to the billing transaction 206 may also include, without limitation, one or more fields comprising a patient pay amount field populated with a value returned by the claims processor computer 106, an associated dispense quantity field populated with a submitted quantity dispensed based on information from the billing request transaction 204, a usual and customary charge field populated with the submitted usual and customary charge on the billing request transaction 204, a pharmacy name field populated with a short pharmacy name corresponding to the submitted pharmacy ID included on the billing request transaction 204, and/or a pharmacy street address populated with a pharmacy street address corresponding to the submitted pharmacy ID included on the billing request transaction 204.

If, on the other hand, the response field in the adjudicated response to the billing transaction 206 includes the transaction status indicator "R", the adjudicated response to the billing transaction 206 may also include, without limitation, one or more fields comprising the patient pay amount field left blank, the associated dispense quantity field left blank, a reject reason field populated with a rejection reason or code identifying the rejection reason for the rejected billing request transaction 204 (e.g., pricing not available for an identified scenario, reject description, non-formulary medication, prior authorization required, or the like), the usual and customary charge field left blank, the pharmacy name field left blank, a reason for service code field populated with a reject error code, and/or a reason for service description field populated with an abbreviated description of the corresponding reason for service code.

In step 328, the service provider computer 108 receives the adjudicated response to the billing transaction 206. In step 330, the service provider computer 104 may capture information associated with the one or more fields included in the adjudicated response to the billing transaction 206. In one example embodiment, the service provider computer 104 may employ a network benefit check module 110 or another portion of the service provider computer 104 to capture information associated with the one or more fields included in the adjudicated response to the billing transaction 206. For example, for a paid response (i.e., the transaction indicator status is identified as "P"), the service provider computer 104 may (i) identify the transaction response type (i.e., a pharmacy billing or a prescriber billing); (ii) determine the status of the billing response transaction (iii) determine if there is a pharmaceutical manufacturer message to deliver; (iv) capture the transaction response for the corresponding billing request transaction 204 to submit a subsequent reversal request; and/or (v) format a paid prescription benefit check response transaction. For example, the adjudicated response to the billing transaction 206 may include:

Transaction Type "R" (i.e., a pharmacy billing transaction type) or "P" (i.e., a prescriber billing transaction type)
Transaction status indicator "P" (i.e., paid)
Patient pay amount—the patient copay amount
Associated dispense quantity
Associated dosage form
Claims processor computer message
Pharmaceutical manufacturer message
Pharmacy name In one example embodiment, the claims processor computer message and/or the pharmaceutical manufacturer message may be limited to a predetermined field length (i.e., 40 characters). If the claims processor computer message and/or the pharmaceutical manufacture message exceed the predetermined field length, a "more information" indicator may be displayed indicating that there is an additional portion to the claims processor computer message and/or the pharmaceutical manufacturer message. The claims processor message and/or the pharmaceutical manufacturer message may have a predetermined maximum field length (i.e., 200 characters).

In step 332, an inquiry is conducted to determine if the billing request transaction is a billing transaction. In certain example embodiments, the determination can be made by the network benefit check module 110 or another portion of the service provider computer 104. For example, the network benefit check module 110 or another portion of the service provider computer 104 may parse the correct field (e.g., the transaction type field) of the adjudicated response to the billing request transaction 206 or the associated billing request transaction 204 to determine the transaction type code included in that field and may compare that transaction type code to a table, list, or schedule of known billing transaction codes to determine if the transaction type code in the adjudicated response 206 matches a billing transaction code and accordingly the transaction type is a billing transaction. If the billing request transaction is a billing transaction, the YES branch is followed to step 334. Otherwise, the NO branch is followed to step 364 of FIG. 3B.

In step 334, an inquiry is conducted to determine if the billing request transaction was paid. In certain example embodiments, the determination can be made by the network benefit check module 110 or another portion of the service provider computer 104. For example, the network benefit check module 110 or another portion of the service provider computer 104 may parse the correct field (e.g., the transaction status indicator field) of the adjudicated response to the billing request transaction 206 to determine the status indicator code included in that field and may compare that status indicator code to a table, list, or schedule of known status indicator codes to determine if the status indicator code in the adjudicated response 206 signifies that the transaction was paid or not. If the billing request transaction was paid, the YES branch is followed to step 336. Otherwise, the NO branch is followed to step 364 of FIG. 3B.

In step 336, the network benefits check module 110 or another portion of the service provider computer 104 generates a reversal transaction based on information included in the billing request transaction and/or the adjudicated response to the billing request transaction. An example embodiment of generating the reversal transaction is discussed in greater detail with reference to FIG. 9 hereinbelow. The network benefit check module 110 or another portion of the service provider computer 104 may retrieve or otherwise identify the pharmacy ID included in the adjudicated response to the billing request transaction 206 in step 338. In step 340, the network benefit check module 110 or another portion of the service provider computer 104 may compare the retrieved pharmacy ID to a table, list, or schedule of pharmacies that have contracted with the service provider to receive certain services. Alternatively, this determination could have been made as part of the initial processing of the prescription benefit check request as described in step 314 above.

In step 342, an inquiry is conducted to determine if the pharmacy represented by the retrieved pharmacy ID is a contracted pharmacy. For example, the network benefit check module 110 or another portion of the service provider computer 104 can compare the retrieved pharmacy ID to the list of contracted pharmacies to see if a match exists, thereby signifying that the pharmacy identified by the pharmacy ID is a contracted pharmacy. If the pharmacy is not a contracted pharmacy, then the NO branch is followed to step 364 of FIG. 3B. On the other hand, if a match exists and the pharmacy identified by the retrieved pharmacy ID is a contracted pharmacy, the YES branch is followed to step 344 of FIG. 3B.

In step 344, an inquiry is conducted to determine if the contracted pharmacy represented by the retrieved pharmacy ID is contracted to receive incentive program services, such as coupon and other incentive identification services provided under an eVoucheRx™ program. In one example embodiment, the inquiry can be conducted by the network benefit check module 110 or another portion of the service provider computer 104. For example, the network benefit check module 110 can query a table, list, or schedule of contracted pharmacies that may also include the services provided for each of those pharmacies to determine if the pharmacy identified by the pharmacy ID receives incentive program services. If the pharmacy does not receive incentive program services, the NO branch is followed to step 364. If the pharmacy does receive incentive program services, the YES branch is followed to step 346, where the network benefit check module 110 or another portion of the service provider computer 104 retrieves the medication identifier from the billing request transaction 206.

In step 348, the network benefit check module 110 or another portion of the service provider computer 104 compares the retrieved mediation identifier to a schedule, list, or table of medication identifiers for which coupons, discounts, rebates, or other incentives in an incentive program are available. In step 350, an inquiry is conducted to determine if the prescription benefit check transaction 202 qualifies for a coupon, discount, rebate or other similar incentive for an incentive program based on the medication identifier in the adjudicated response 206. For example, the network benefit check module 110 or another portion of the service provider computer 104 can compare the medication identifier to the list of medication identifiers for which coupons, discounts, rebates or other incentives in an incentive program are available to see if a match exists, thereby signifying that the medication identified by the medication identifier qualifies for an incentive and therefore the transaction qualifies for an incentive. In addition to determining if the medication qualifies for an incentive program, other factors may be evaluated before determining if an incentive will be received including but not limited to patient gender, patient zip/postal code, dispensed quantity of medication, historical use of the medication by the patient, including whether the patient has previously or not previously used the medication and whether the patient is adhering to a proper regimen of use of the medication based on the timing of refills. If the transaction 202 qualifies for a coupon or other incentive, the YES branch is followed to step 352. Otherwise, the NO branch is followed to step 364.

In step 352, the network benefit check module 110 or another portion of the service provider computer 104 calculates the incentive amount to be received by the patient. In certain example embodiments, the incentive amount may be included in a record of the database 112 and may be queried based on the medication identifier. For example, a pharmaceutical manufacturer or other sponsor of the incentive can specify how much of an incentive they want to provide based on one or more factors. In another example, pharmaceutical manufacturers or other sponsor of the incentive can specify how much they want the patient co-pay to ultimately be, thereby making the exact amount of the incentive variable based on each patient's original co-pay amount identified in an adjudicated response. In step 354, the network benefit check module 110 or another portion of the service provider computer 104 modifies the patient copay amount in the patient pay amount field of the adjudicated response to the billing request transaction 206 based on the incentive amount calculated to be received by the patient. For example, if the patient copay in the adjudicated response 206 was $75 and the calculated incentive amount is $50, then the patient copay amount in the patient pay amount field would be adjusted to read $25.

In step 356, an inquiry is conducted to determine whether to include a message to the prescriber regarding application of the incentive amount to the patient copay. In certain example embodiments, the medication manufacturer, a marketer of the medication, or the service provider may choose whether to include this message and the determination can be made by the network benefit check module 110 or another portion of the service provider computer 104. If a message will not be included, the NO branch is followed to step 364. If a message will be included, the YES branch is followed to step 358.

In step 358, an inquiry is conducted to determine if the message to the prescriber regarding application of the incentive amount to the patient copay will be included in the adjudicated response to the billing request transaction. In certain example embodiments, the medication manufacturer, a marketer of the medication, or the service provider may choose whether to include this message in the adjudicated response or to send the response to the prescriber separate, such as in an appended message, via email, via facsimile, via text message or some other form of communication. The determination can be made by the network benefit check module 110 or another portion of the service provider computer 104. If the message will be included in the adjudicated response 206, the YES branch is followed to step 360, where the network benefit check module 110 or another portion of the service provider computer 104 can generate a message informing the prescriber that an incentive amount was applied to the patient copay to reduce the patient copay and can insert that message into a text field of the adjudicated response 206. In certain example embodiments, the message can include the amount of the incentive amount and who was providing the incentive amount. The process then continues to step 364.

Returning to step 358, if the message will not be included in the adjudicated response 206, the NO branch is followed to step 362, where the network benefit check module 110 or another portion of the service provider computer 104 generates and transmits a message to the prescriber regarding application of the incentive amount. In certain example embodiments, the message may be communicated to the prescriber at the prescriber computer 102 or alternatively the message may be communicated to another device or faxed to the prescriber at a number associated with the prescriber.

In step 364, the service provider computer 104 may transmit the adjudicated response to the billing transaction 206 to the prescriber computer 102 via, for example, the network 114. For example, the adjudicated response to the billing transaction 206 may be transmitted to the provider benefit check module 132 of the prescriber computer 102. In step 366, the prescriber computer 102 may receive the adjudicated response to the billing transaction 206 and may display the adjudicated response to the billing transaction 206 on a display of the prescriber computer 102.

If the adjudicated response to the billing transaction 206 is a paid ("P") adjudicated response to the billing transaction 206 corresponding to a pharmacy billing transaction type (i.e., "R"), the adjudicated response to the billing transaction 206 may include the following fields and information on the display at the prescriber computer 102:
Transaction response type—R
Transaction status indicator—P
Patient Pay Amount—Yes (showing patient copay amount)
Associated dispense quantity—Yes (showing dispense quantity of the medication)
Associated dosage form—Yes (showing dosage amount)
Service provider computer message—No
Claims processor computer message—No
Pharmaceutical manufacturer message—Optional (may include information about application of an incentive amount against the patient copay amount to reduce the patient copay amount)
Reject Reason—No
Pharmacy Name—Yes
Reason for service message—No
If the adjudicated response to the billing transaction 206 is a paid ("P") adjudicated response to the billing transaction 206 corresponding to a prescriber billing transaction type (i.e., "P"), the adjudicated response to the billing transaction 206 may be displayed as:
Transaction response type—P
Transaction status indicator—P
Patient pay amount—Yes (showing patient copay amount)
Associated dispense quantity—Yes (showing dispense quantity of the medication)
Associated dosage form—Yes (showing dosage amount)
Service provider computer message—No
Claims processor computer message—Optional
Pharmaceutical manufacturer message—Optional (may include information about application of an incentive amount against the patient copay amount to reduce the patient copay amount)
Reject reason—No
Pharmacy Name—Yes
Reason for service—No
If the adjudicated response to the billing transaction 206 is a paid ("P") adjudicated response to the billing transaction 206 corresponding to a predetermination of benefits billing transaction type (i.e., "D"), the adjudicated response to the billing transaction 206 may be displayed as:
  Transaction response type—D
  Transaction status indicator—A
  Patient pay amount—TBD
  Associated dispense quantity—TBD
  Associated dosage form—TBD
  Service provider computer message—No
  Claims processor computer message—TBD
  Pharmaceutical manufacturer message—TBD
  Reject reason—TBD
  Pharmacy Name—TBD
  Reason for service—TBD If the adjudicated response to the billing transaction 206 is a rejected ("R") adjudicated response to the billing transaction 206 corresponding to a pharmacy billing transaction type (i.e., "R"), the adjudicated response to the billing transaction 206 may be displayed as:
  Transaction response type—R
  Transaction status indicator—R
  Patient Pay Amount—No
  Associated dispense quantity—No
  Associated dosage form—No
  Service provider computer message—Optional
  Claims processor computer message—No
  Pharmaceutical manufacturer message—Optional
  Reject Reason—Yes
  Pharmacy Name—No
  Reason for service message—Optional If the adjudicated response to the billing transaction 206 is a rejected ("R") adjudicated response to the billing transaction 206 corresponding to a prescriber billing transaction type (i.e., "P"), the adjudicated response to the billing transaction 206 may be displayed as:
  Transaction response type—P
  Transaction status indicator—R
  Patient pay amount—No
  Associated dispense quantity—No
  Associated dosage form—No
  Service provider computer message—Optional
  Claims processor computer message—Optional
  Pharmaceutical manufacturer message—Optional
  Reject reason—Yes
  Pharmacy Name—No
  Reason for service—Optional If the adjudicated response to the billing transaction 206 is a rejected ("R") adjudicated response to the billing transaction 206 corresponding to a predetermination of benefits billing transaction type (i.e., "D"), the adjudicated response to the billing transaction 206 may be displayed as:
  Transaction response type—D
  Transaction status indicator—R
  Patient pay amount—No
  Associated dispense quantity—No
  Associated dosage form—No
  Service provider computer message—No
  Claims processor computer message—Optional
  Pharmaceutical manufacturer message—Optional
  Reject reason—Yes
  Pharmacy Name—No
  Reason for service—Optional The process continues from step 366 to the END step.

Figure 4:
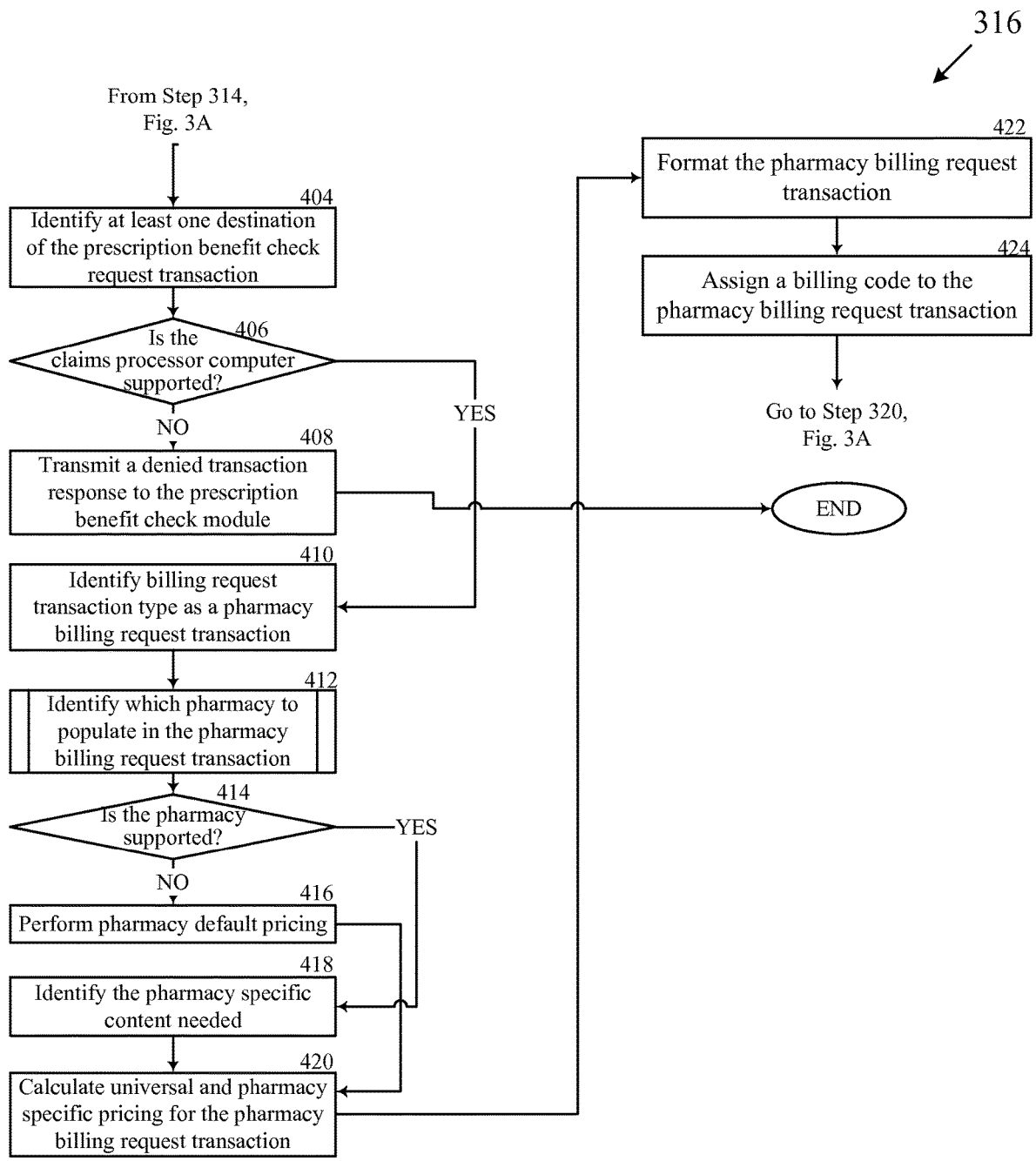
FIG. 4 is a flow chart of an example method for determining the transaction type of the prescription benefit check transaction as a pharmacy billing transaction and processing the determined pharmacy billing transaction, according to one exemplary embodiment.

FIG. 4 is a flow chart of an example method 316 for determining the transaction type of the prescription benefit check transaction 202 as a pharmacy billing transaction and processing the determined pharmacy billing transaction. Referring now to FIGS. 1A-B, 2, 3A and 4, the exemplary method 316 begins at step 404, where the service provider computer 104 may identify at least one destination of the prescription benefit check transaction 202. In one example embodiment, the destination of the prescription benefit check transaction 202 may be the claims processor computer 106. The claims processor computer 106 may be identified using the BIN Number or the BIN Number and PCN or the BIN Number and Group ID included in the prescription benefit check transaction 202.

In step 406, an inquiry is conducted to determine if the claims processor computer identified in the prescription benefit check transaction is one that is supported by the service provider computer 104. For example, the service provider computer 104 may determine whether the identified claims processor computer 106 is a supported claims processor computer 106 by accessing one or more supported claims processor computer files 154 to determine whether the identified claims processor computer 106 is a supported destination. In one example embodiment, the service provider computer 104 may employ the network benefit check module 110 to access one or more supported claims processor computer files 154. The network benefit check module 110 may compare the submitted BIN Number or the BIN Number and PCN or the BIN Number and Group ID on one or more tables within one or more supported claims processor computer files 154. The one or more tables may include, without limitation, a BIN Number field, a PCN field, a Group ID field and/or a support designation field including a support indicator (i.e., a "Y" for supported or a "N" for not supported). The network benefit check module 110 may parse the one or more supported claims processor computer files 154 to identify whether the BIN Number or BIN Number and PCN or BIN Number and Group ID exists in the one or more tables. If the BIN Number or the BIN Number and PCN or the BIN Number and Group ID exists in the one or more supported claims processor computer files 154, and, for example, a "Y" support indicator accompanies the existing file, then the YES branch is followed to step 410. If the BIN Number or the BIN Number and PCN or the BIN Number and Group ID does not exist in the one or more supported claims processor computer files 154, and/or a "N" support indicator accompanies the existing file, then the NO branch is followed to step 408. In step 408, the service provider computer 104 generates and transmits a denied transaction response 208 to the prescriber computer 102 via, for example, the network 114. The process then continues to the END step.

In step 410, the service provider computer 104 may identify the prescription benefit check transaction 202 as a pharmacy billing transaction. For example, during the processing of the prescription benefit check transaction 202, the network benefit check module 110 or another portion of the service provider computer 104 may parse the transaction type code in the prescription benefit check transaction 202 and identify the transaction type as a pharmacy billing transaction. This identification may be based on the transaction 202 having a Transaction Type designation of "R".

In step 412, the service provider computer 104 may identify which pharmacy to populate in the pharmacy billing request transaction 204. In one example embodiment, the pharmacy information utilized to populate the pharmacy billing request transaction 204 may be the pharmacy benefit information identified by the patient. For example, the patient may provide the prescriber or another person working in conjunction with the prescriber (i.e. receptionist, administrative assistant, nurse or other assistant) with the patient's preferred pharmacy information. The patient's preferred pharmacy information may be input into the prescription benefit check transaction 202 at the prescriber computer 102 via the I/O interface 120. During the processing of the prescription benefit check transaction 202, the service provider computer 104 may identify the preferred pharmacy information in the prescription benefit check transaction 202. Alternatively, if no preferred pharmacy information is identified/provided in the prescription benefit check transaction 202, a default pharmacy information may be populated in the pharmacy billing request transaction 204 by the network benefit check module 110 or another portion of the service provider computer 104. A more detailed description of an example embodiment for determining a default pharmacy is provided in FIG. 7 hereinbelow.

In step 414, an inquiry is conducted to determine if the pharmacy is supported (i.e., a contracted pharmacy) by the service provider computer 104. The service provider computer 104 may determine whether the identified pharmacy is a supported pharmacy by employing the network benefit check module 110 or another portion of the service provider computer to access one or more supported pharmacy files 148 in the database 112. The network benefit check module 110 may compare a pharmacy identifier (i.e., pharmacy name, NPI number, a National Council for Prescription Drug Programs (NCPDP) Provider ID, an ePrescribing identifier, and/or a pharmacy identification number, etc.) to one or more tables within one or more supported pharmacy files 148. The one or more tables may include fields including, without limitation, a pharmacy name, a pharmacy identification number, an NPI number, an NCPDP Provider ID, an ePrescribing identifier, a pharmacy location (i.e., a postal code, an address including street address, city, state/province, and zip/postal code), etc.), and/or a support designation field including a support indicator (e.g., a "Y" for supported or a "N" for not supported). The service provider computer 104 may parse the one or more tables within the supported pharmacy files 148 to identify whether the pharmacy identifier exists in the one or more supported pharmacy files. If the pharmacy identifier does not exist in the one or more supported pharmacy files 148, and/or, for example, a "N" support indicator accompanies the existing file, then the NO branch is followed to step 416.

In step 416, the service provider computer 104 may access one or more default pharmacy pricing files 150. The service provider computer 104 may employ a network benefit check module 110 to identify a medication identifier (i.e., a NDC code, an RxNorm medication identifiers, medication name, or the like) submitted in the prescription benefit check transaction 202. The network benefit check module 110 may also access a prescribed quantity included in the prescription benefit check transaction 202. In one example, utilizing the NDC code and the prescribed quantity, the service provider computer 104 may parse the one or more default pharmacy pricing files 150 to determine a universal pharmacy price corresponding to the medication identified by the medication identifier and the prescribed quantity identified in the prescription benefit check transaction 202. The process then continues to step 420.

Returning to the inquiry of step 414, if the pharmacy identifier exists in the one or more supported pharmacy files 148, and, for example, a "Y" support indicator accompanies the existing file, then the YES branch is followed to step 418. In step 418, the service provider computer 104 may access one or more pharmacy transaction files 146. In one example embodiment, the service provider computer 104 may employ the network benefit check module 110 or another portion of the service provider computer 104 to access the one or more pharmacy transaction files 146. The one or more pharmacy transaction files 146 may be organized by a pharmacy identifier (i.e., pharmacy name, NPI number, an NCPDP Provider ID, an ePrescribing identifier, a pharmacy identification number, etc.). Each of the pharmacy transaction files 146 may include a medication identifier, a quantity dispensed, and a specific price associated with the medication identifier and the quantity dispensed. The network benefit check module 110 may identify the medication identifier (i.e., a NDC code, an RxNorm medication identifier, or the like) submitted in a particular field of the prescription benefit check transaction 202. The service provider computer 104 may also access a prescribed quantity included in a particular field of the prescription benefit check transaction 202. In one example, utilizing the NDC code and the prescribed quantity, the service provider computer 104 may parse the one or more pharmacy transaction files 146 to determine a specific pharmacy price for the pharmacy identified in the transaction 202 and corresponding to the medication and prescribed quantity identified in the prescription benefit check transaction 202 based on historical transactions received for that particular pharmacy.

In step 420, the service provider computer 104 may calculate the universal pharmacy pricing identified in step 416 or the specific pharmacy pricing identified in step 418. In step 422, the service provider computer 104 may format the pharmacy billing request transaction 204. In one example embodiment, the pharmacy billing request transaction 204 may include, without limitation, a transaction header, an insurance segment, a patient segment, a claim segment, a prescriber segment, and/or a pricing segment. For example, without limitation, the pharmacy billing request transaction 204 may include:

Transaction header
  BIN Number
  Version release number
  Transaction code
  PCN
  Transaction count
  Pharmacy ID qualifier
  Pharmacy ID (e.g., pharmacy name, NPI number, an NCPDP Provider
    ID, an ePrescribing identifier, etc.)
  Date of Service
Insurance segment
  Segment identification
  Cardholder ID
  Group ID
  Person code
  Patient relationship code
Patient Segment
  Segment identification
  Patient first name
  Patient last name
  Date of birth
  Patient zip code
  Patient gender code
Claim segment
  Segment identification
  Prescription/Service reference number qualifier
  Prescription/Service reference number
  Product/Service ID qualifier
  Product/Service ID (e.g. NDC code or RxNorm medication identifier)
  Quantity dispensed
  Fill number
  Days' supply Compound code
Product selection code
Date prescription written
Quantity prescribed
Prescriber segment
  Segment identification
  Prescriber ID qualifier
  Prescriber ID (e.g., NPI number or DEA number)
  Prescriber last name
Pricing segment
  Segment identification
  Ingredient cost submitted
  Dispensing fee submitted
  Flat sales tax amount submitted
  Percent sales tax amount submitted
  Usual and customary charge
  Gross amount due At step 424, the service provider computer 104 may assign a billing code to the pharmacy billing request transaction 204. The process continues to step 320 of FIG. 3A.

Figure 5:
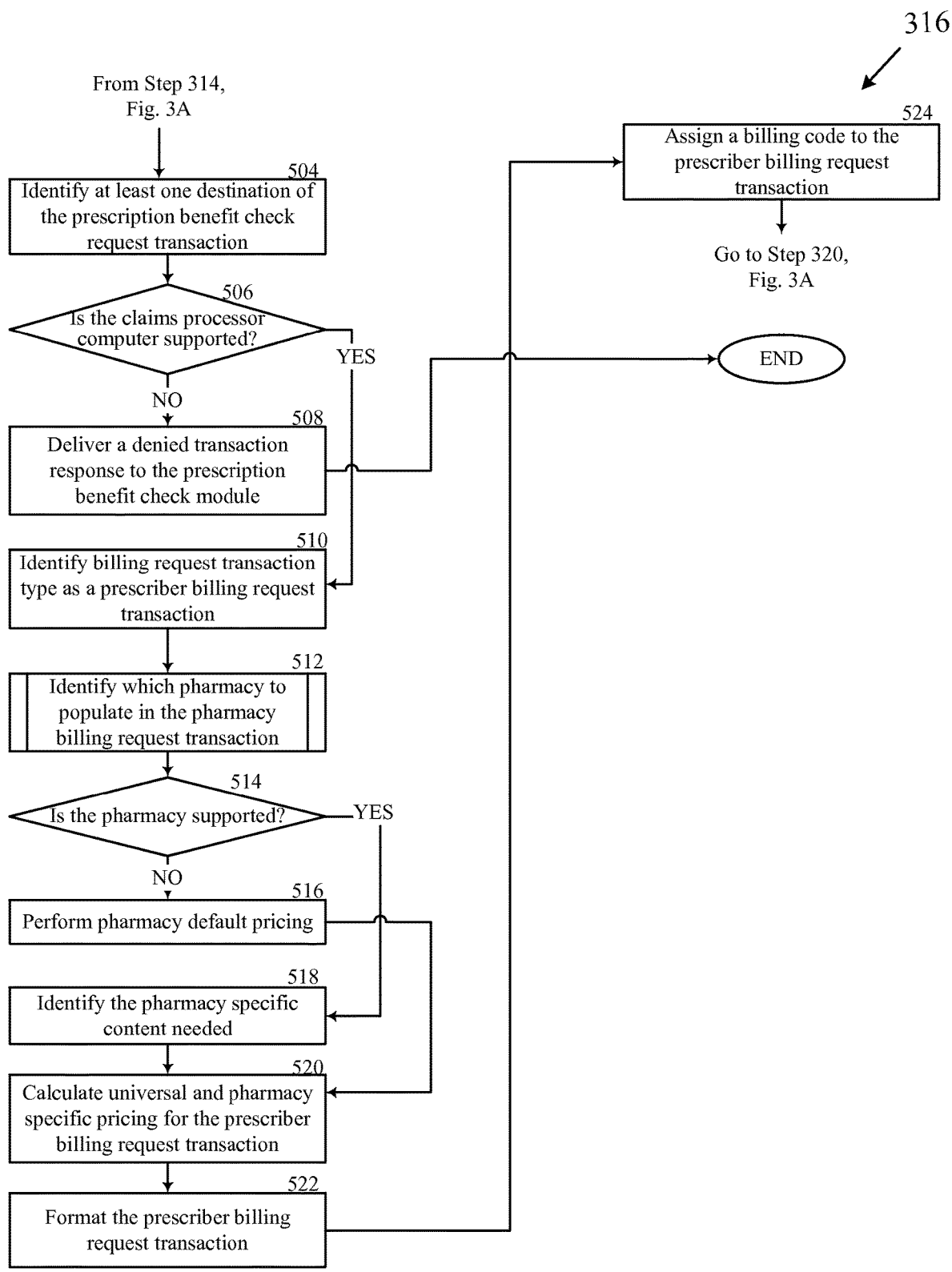
FIG. 5 is a flow chart of an example method for determining the transaction type of the prescription benefit check transaction as a prescriber billing transaction and processing the determined prescriber billing transaction, according to one exemplary embodiment.

FIG. 5 is a flow chart of an example method 316 of FIG. 3A for determining the transaction type of the prescription benefit check transaction 202 as a prescriber billing transaction and processing the determined prescriber billing transaction according to one example embodiment. Referring now to FIGS. 1A-B, 2, 3A, and 5, the exemplary method 316 begins at step 504, where the service provider computer 104 may identify at least one destination of the prescription benefit check transaction 202. In one example embodiment, the destination of the prescription benefit check transaction 202 may be the claims processor computer 106. The claims processor computer 106 may be identified using the BIN Number or the BIN Number and PCN or the BIN Number and Group ID included in one or more fields of the prescription benefit check transaction 202.

In step 506, an inquiry is conducted to determine if the claims processor computer identified in the prescription benefit check transaction is one that is supported by the service provider computer 104. For example, the service provider computer 104 may determine whether the identified claims processor computer 106 is a supported claims processor computer 106 by accessing one or more supported claims processor computer files 154 to determine whether the identified claims processor computer 106 is a supported destination. In one example embodiment, the service provider computer 104 may employ the network benefit check module 110 to access one or more supported claims processor computer files 154. The network benefit check module 110 may compare the submitted BIN Number or the BIN Number and PCN or the BIN Number and Group ID on one or more tables within one or more supported claims processor computer files 154. The one or more tables may include, without limitation, a BIN Number field, a PCN field, a Group ID field and/or a support designation field including a support indicator (i.e., a "Y" for supported or a "N" for not supported). The network benefit check module 110 may parse the one or more supported claims processor computer files 154 to identify whether the BIN Number or BIN Number and PCN or BIN Number and Group ID exists in the one or more tables. If the BIN Number or the BIN Number and PCN or the BIN Number and Group ID exists in the one or more supported claims processor computer files 154, and, for example, a "Y" support indicator accompanies the existing file, then the YES branch is followed to step 510. If the BIN Number or the BIN Number and PCN or the BIN Number and Group ID does not exist in the one or more supported claims processor computer files 154, and/or a "N" support indicator accompanies the existing file, then the NO branch is followed to step 508. In step 508, the service provider computer 104 generates and transmits a denied transaction response 208 to the prescriber computer 102 via, for example, the network 114. The process then continues to the END step.

In step 510, the service provider computer 104 may identify the prescription benefit check transaction 202 as a prescriber billing transaction. For example, during the processing of the prescription benefit check transaction 202, the network benefit check module 110 or another portion of the service provider computer 104 may parse the transaction type code in the prescription benefit check transaction 202 and identify the transaction type as a prescription billing transaction. This identification may be based on the transaction 202 having a Transaction Type designation "P".

In step 512, the service provider computer 104 may identify which pharmacy to populate in the pharmacy billing request transaction 204. In one example embodiment, the pharmacy information utilized to populate the pharmacy billing request transaction 204 may be the pharmacy benefit information identified by the patient. For example, the patient may provide the prescriber or another person working in conjunction with the prescriber (i.e. receptionist, administrative assistant, nurse or other assistant) with the patient's preferred pharmacy information. The patient's preferred pharmacy information may be input into the prescription benefit check transaction 202 at the prescriber computer 102 via the I/O interface 120. During the processing of the prescription benefit check transaction 202, the service provider computer 104 may identify the preferred pharmacy information in the prescription benefit check transaction 202. Alternatively, if no preferred pharmacy information is identified/provided in the prescription benefit check transaction 202, a default pharmacy information may be populated in the pharmacy billing request transaction 204 by the network benefit check module 110 or another portion of the service provider computer 104. A more detailed description of an example embodiment for determining a default pharmacy is provided in FIG. 7 hereinbelow.

In step 514, an inquiry is conducted to determine if the pharmacy is supported (i.e., a contracted pharmacy) by the service provider computer 104. The service provider computer 104 may determine whether the identified pharmacy is a supported pharmacy by employing the network benefit check module 110 or another portion of the service provider computer to access one or more supported pharmacy files 148 in the database 112. The network benefit check module 110 may compare a pharmacy identifier (i.e., a pharmacy name, NPI number, an NCPDP Provider ID, an ePrescribing identifier, and/or a pharmacy identification number, etc.) to one or more tables within one or more supported pharmacy files 148. The one or more tables may include fields including, without limitation, a pharmacy name, a pharmacy identification number, an NPI number, a pharmacy location (i.e., a postal code, an address including street address, city, state/province, and zip/postal code), etc.), and/or a support designation field including a support indicator (e.g., a "Y" for supported or a "N" for not supported). The service provider computer 104 may parse the one or more tables within the supported pharmacy files 148 to identify whether the pharmacy identifier exists in the one or more supported pharmacy files. If the pharmacy identifier does not exist in the one or more supported pharmacy files 148, and/or, for example, a "N" support indicator accompanies the existing file, then the NO branch is followed to step 516.

In step 516, the service provider computer 104 may access one or more default pharmacy pricing files 150. The service provider computer 104 may employ a network benefit check module 110 or another portion of the service provider computer 104 to identify a medication identifier (i.e., a NDC code, an RxNorm medication identifiers, medication name, or the like) submitted in the prescription benefit check transaction 202. The network benefit check module 110 or another portion of the service provider computer 104 may also access a prescribed quantity included in the prescription benefit check transaction 202. In one example, utilizing the NDC code and the prescribed quantity, the service provider computer 104 may parse the one or more default pharmacy pricing files 150 to determine a universal pharmacy price corresponding to the medication identified by the medication identifier and the prescribed quantity identified in the prescription benefit check transaction 202. The process then continues to step 520.

Returning to the inquiry of step 514, if the pharmacy identifier exists in the one or more supported pharmacy files 148, and, for example, a "Y" support indicator accompanies the existing file, then the YES branch is followed to step 518. In step 518, the service provider computer 104 may access one or more pharmacy transaction files 146. In one example embodiment, the service provider computer 104 may employ the network benefit check module 110 or another portion of the service provider computer 104 to access the one or more pharmacy transaction files 146. The one or more pharmacy transaction files 146 may be organized by a pharmacy identifier (i.e., a pharmacy name, NPI number, an NCPDP Provider ID, an ePrescribing identifier, a pharmacy identification number, etc.). Each of the pharmacy transaction files 146 may include a medication identifier, a quantity dispensed, and a specific price associated with the medication identifier and the quantity dispensed. The network benefit check module 110 may identify the medication identifier (i.e., a NDC code, an RxNorm medication identifier, or the like) submitted in a particular field of the prescription benefit check transaction 202. The service provider computer 104 may also access a prescribed quantity included in a particular field of the prescription benefit check transaction 202. In one example, utilizing the NDC code and the prescribed quantity, the service provider computer 104 may parse the one or more pharmacy transaction files 146 to determine a specific pharmacy price for the pharmacy identified in the transaction 202 and corresponding to the medication and prescribed quantity identified in the prescription benefit check transaction 202 based on historical transactions received for that particular pharmacy.

In step 520, the service provider computer 104 may calculate the universal pharmacy pricing identified in step 516 or the specific pharmacy pricing identified in step 518. In step 522, the service provider computer 104 may format the prescriber billing request transaction 204. In one example embodiment, the prescriber billing request transaction 204 may include, without limitation, a transaction header, an insurance segment, a patient segment, a claim segment, a prescriber segment, and/or a pricing segment. For example, without limitation, the prescriber billing request transaction 204 may include:

Transaction header
  BIN Number
  Version release number
  Transaction code
  PCN
  Transaction count
  Pharmacy ID qualifier
  Pharmacy ID (e.g., pharmacy name, NPI number, an NCPDP Provider ID, an ePrescribing identifier, etc.)
  Date of Service
Insurance segment
  Segment identification
  Cardholder ID
  Group ID
  Person code
  Patient relationship code
Patient Segment
  Segment identification
  Patient first name
  Patient last name
  Date of birth
  Patient zip/postal code
  Patient gender code
Claim segment
  Segment identification
  Prescription/Service reference number qualifier
  Prescription/Service reference number
  Product/Service ID qualifier
  Product/Service ID (e.g. NDC code or RxNorm medication identifier)
  Quantity dispensed
  Fill number
  Days' supply
  Compound code
  Product selection code
  Date prescription written
  Quantity prescribed
Prescriber segment
  Segment identification
  Prescriber ID qualifier
  Prescriber ID (e.g., NPI number or DEA number)
  Prescriber last name
Pricing segment
  Segment identification
  Ingredient cost submitted
  Dispensing fee submitted
  Flat sales tax amount submitted
  Percent sales tax amount submitted
  Usual and customary charge
  Gross amount due At step 524, the service provider computer 104 may assign a billing code to the prescriber billing request transaction 204. The process then continues to step 320 of FIG. 3A.

Figure 6:
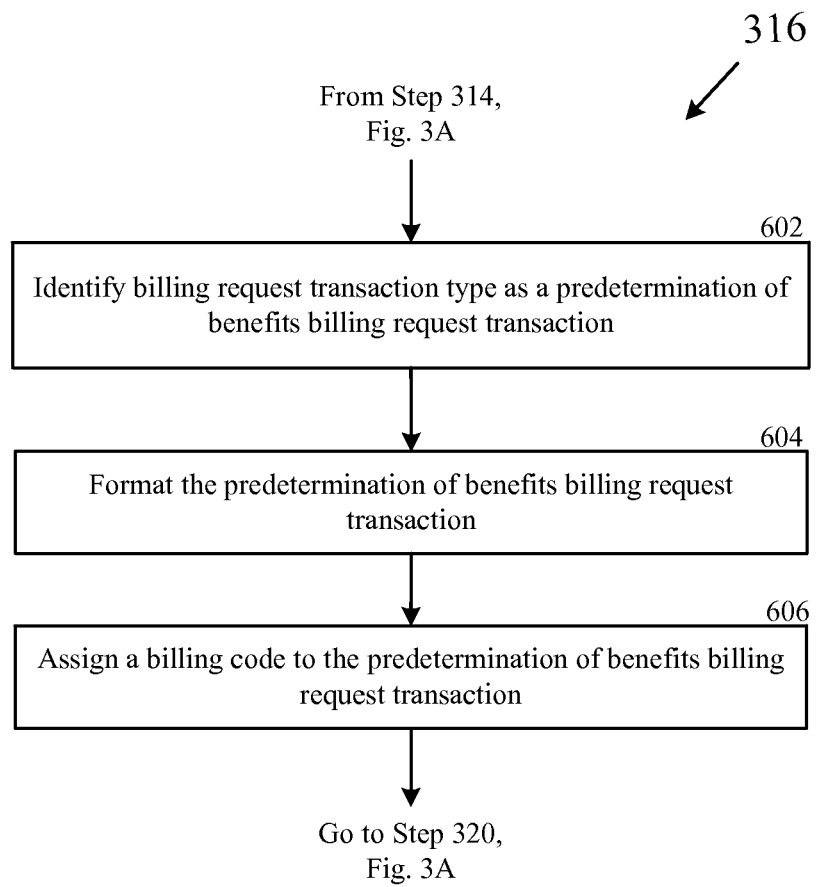
FIG. 6 is a flow chart of an example method for determining the transaction type of the prescription benefit check transaction as a predetermination of benefits transaction and processing the determined predetermination of benefits transaction, according to one exemplary embodiment.

FIG. 6 is a flowchart of an example method 316 of FIG. 3A for determining the transaction type of the prescription benefit check transaction 202 as a predetermination of benefits billing transaction and processing the determined predetermination of benefits billing transaction in accordance with an exemplary embodiment. Now referring to FIGS. 1A-B, 2, 3A, and 6, the exemplary method 316 begins at step 602, where the service provider computer 104 may identify the transaction type associated with the prescription benefit check transaction 202. For example, the prescription benefit check transaction 202 may be associated with a pharmacy billing transaction, a prescriber billing transaction, or a predetermination of benefits transaction. During the processing of the prescription benefit check transaction 202, the service provider computer 104 may identify the transaction type based upon the transaction type designation included in the prescription benefit check transaction 202 (i.e., as a prescriber billing transaction by a Transaction Type designation "P", as a pharmacy billing transaction by a Transaction Type designation "R", as a predetermination of benefits transaction billing transaction by a Transaction Type designation "D"). As illustrated in FIG. 6, the transaction type designation included in exemplary method 316 is a predetermination of benefits transaction type (i.e., a Transaction Type designation "D" is identified).

In step 604, the service provider computer 104 may format the predetermination of benefits billing request transaction 204. In one example embodiment, the predetermination of benefits billing request transaction 204 may include, without limitation, a transaction header, an insurance segment, a patient segment, a claim segment, a prescriber segment, and/or a pricing segment. For example, without limitation, the prescriber billing request transaction may include:

Transaction header
    BIN Number
    Version release number
    Transaction code
    PCN
    Transaction count
    Pharmacy ID qualifier
    Pharmacy ID (e.g., pharmacy name, NPI number, an NCPDP Provider ID, an ePrescribing identifier, etc.)
    Date of Service
Insurance segment
    Segment identification
    Cardholder ID
    Group ID
    Person code
    Patient relationship code
Patient Segment
    Segment identification
    Patient first name
    Patient last name
    Date of birth
    Patient zip/postal code
    Patient gender code
Claim segment
    Segment identification
    Prescription/Service reference number qualifier
    Prescription/Service reference number
    Product/Service ID qualifier
    Product/Service ID (e.g. NDC code or RxNorm medication identifier)
    Quantity dispensed
    Fill number
    Days' supply
    Compound code
    Product selection code
    Date prescription written
    Quantity prescribed
Prescriber segment
    Segment identification
    Prescriber ID qualifier
    Prescriber ID (e.g., NPI number or DEA number)
    Prescriber last name
Pricing segment
    Segment identification
    Ingredient cost submitted
    Dispensing fee submitted
    Flat sales tax amount submitted
    Percent sales tax amount submitted
    Usual and customary charge
    Gross amount due At step 606, the service provider computer 104 may assign a billing code to the predetermination of benefits billing request transaction 204. The process then continues to step 320 of FIG. 3A.

Figure 7:
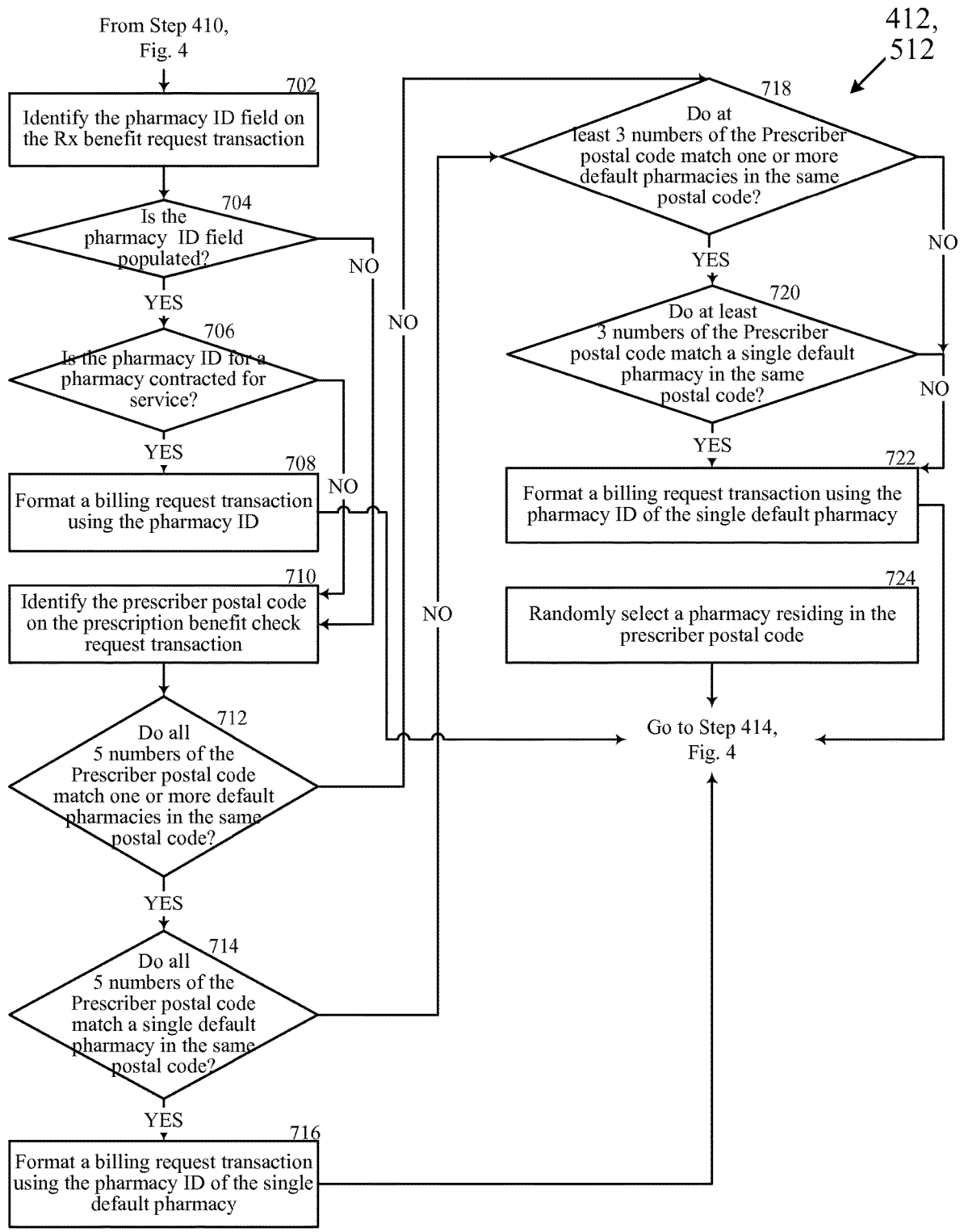
FIG. 7 is a flow chart of an example method for determining a default pharmacy associated with the prescription benefit check transaction, according to one exemplary embodiment.

FIG. 7 is a flow chart illustrating an example method 412 of FIG. 4 for determining a default pharmacy associated with the prescription benefit check transaction 202 in accordance with one exemplary embodiment of the disclosure. Referring now to FIGS. 1A-B, 2, 4, and 7, the exemplary method 412 begins at step 702, where the service provider computer 104 may identify the pharmacy ID field in the submitted prescription benefit check transaction 202. In step 704, an inquiry is conducted to determine if the pharmacy ID field in the submitted prescription benefit request transaction is populated. In one example embodiment, the pharmacy ID corresponds to the patient's preferred pharmacy and the determination can be made by the service provider computer and/or the network benefits module 110. If the service provider computer determines that the pharmacy ID field is populated, then the YES branch is followed a to step 706. Otherwise, the NO branch is followed to step 710.

In step 706, an inquiry is conducted to determine if the pharmacy associated with the pharmacy ID is a contracted pharmacy. In certain example embodiments, the determination can be made by the network benefit check module 110 or another part of the service provider computer 104. For example, the network benefit check module 110 may access one or more supported pharmacy files 148 in the database 112. The network benefit check module 110 may compare the pharmacy ID (i.e., a pharmacy name, NPI number, an NCPDP Provider ID, an ePrescribing identifier, a pharmacy identification number, etc.) to one or more tables within one or more supported pharmacy files 148. The one or more tables may include, without limitation, a pharmacy name field, an NPI number field, a pharmacy identification number field, a pharmacy location field (i.e., a zip/postal code, an address (including street address, city, state/province, and zip/postal code), etc.), a support designation field including a support indicator (i.e., a "Y" for supported or a "N" for not supported), and/or a default pharmacy status indicator (i.e., "DF"). The network benefit check module 110 may parse the one or more tables within the supported pharmacy files 148 to identify whether the pharmacy ID from the prescription benefit check transaction 202 matches a pharmacy ID or other information for a pharmacy in the one or more supported pharmacy files 148. If the network benefit check module 110 determines that a match exists, such that the pharmacy ID matches a pharmacy ID or other pharmacy information that exists in the one or more supported pharmacy files 148, and, for example, a "Y" support indicator accompanies the existing file (or any other basis for indicating that the pharmacy is a contracted pharmacy (such as by merely being in the supported pharmacy files 148, then the YES branch is followed to step 708.

In step 708, the service provider computer 104 may format the billing request transaction 204 to a corresponding billing request transaction type that includes the submitted pharmacy ID in the prescription benefit request transaction 202. For example, the billing request transaction type may include, without limitation, a pharmacy billing request (i.e., the billing designation "R"), a prescriber billing request (i.e., a billing designation "P"), or a predetermination of benefits request (i.e., a billing designation "D"). The process then continues to step 414 of FIG. 4.

Returning to the inquiry of step 706, if the network benefit check module 110 determines that a match does not exist in the one or more supported pharmacy files 148, and/or, for example, a "N" support indicator accompanies the existing file, then the NO branch is followed to step 710. In step 710, the service provider computer 104 may identify the prescriber zip/postal code submitted in the prescription benefit check transaction 202. In one example embodiment, the network benefit check module 110 or another portion of the service provider computer 104 may parse the prescription benefit check transaction 202 to identify the prescriber zip/postal code field and identify the numbers populated in the prescriber zip/postal code field. For example, the network benefit check module 110 may identify the five numbers of the prescriber zip/postal code to be 99026.

In step 712, an inquiry is conducted to determine if the identified prescriber zip/postal code from the prescription benefit check transaction 102 matches one or more default pharmacies within the same identified zip/postal code. In certain example embodiments, the determination can be made by the network benefit check module 110 or another portion of the service provider computer 104. For example, the network benefit check module 110 may identify one or more default pharmacies that match all five numbers of the identified prescriber zip/postal code. For example, if the identified prescriber zip/postal code is 99026, the network benefit check module 110 may determine one or more default pharmacies within the zip/postal code 99026. For example, the network benefit check module 110 may compare the identified prescriber zip/postal code (i.e., 99026) with one or more default pharmacies in one or more supported pharmacy files 148. The network benefit check module 110 may parse the one or more tables within the supported pharmacy files 148 to identify whether the pharmacies within a zip/postal code are default pharmacies (i.e., include the default designation "DF" or some other designation that signifies that they are default pharmacies). If the network benefit module 110 identifies one or more default pharmacies associated with all five numbers of the identified prescriber zip/postal code, then the YES branch is followed to step 714. Otherwise, the NO branch is followed to step 718.

In step 714, an inquiry is conducted to determine if the identified prescriber zip/postal code from the prescription benefit check transaction 102 matches a single pharmacy within the same identified zip/postal code. In certain example embodiments, the determination can be made by the network benefit check module 110 or another portion of the service provider computer 104. If the network benefit module 110 identifies a single default pharmacy associated with all five numbers of the identified prescriber zip/postal code, then the YES branch is followed to step 716. If the network benefit module 110 does not identify a default pharmacy associated with all five numbers of the identified prescriber zip/postal code, then the NO branch is followed to step 718. In step 716, the service provider computer 104 may format the billing request transaction 204 to a corresponding billing request transaction type and include the identified pharmacy ID associated with a default pharmacy. For example, the billing request transaction type may include, without limitation, a pharmacy billing request (i.e., the billing designation "R"), a prescriber billing request (i.e., a billing designation "P"), or a predetermination of benefits request (i.e., a billing designation "D"). The process continues to step 414 of FIG. 4.

In step 718, an inquiry is conducted to determine whether at least three numbers of the identified prescriber zip/postal code match one or more default pharmacies within the same identified zip/postal code. In certain example embodiments, the determination can be made by the network benefit check module 110 or another portion of the service provider computer 104. In one example embodiment, the network benefit check module 110 may identify one or more default pharmacies that match at least three numbers of the identified prescriber zip/postal code. For example, if the identified prescriber zip/postal code is 99026, the network benefit module 110 may determine one or more default pharmacies within the zip/postal code 99026 by searching for at least 990, 026, etc. For example, the service provider computer 104 may compare the identified prescriber zip/postal code (i.e., 99026) with one or more default pharmacies in one or more supported pharmacy files 148 with a default pharmacy designation (i.e., include the default designation "DF" or some other designation that signifies that they are default pharmacies). In certain example embodiments, the one or more supported pharmacy files 148 may be organized by zip/postal code. If the network benefit module 110 identifies one or more default pharmacies associated with at least three numbers of the identified prescriber zip/postal code, then the YES branch is followed to step 720. If the network benefit module 110 does not identify one or more default pharmacies associated with at least three numbers of the identified prescriber zip/postal code, then the NO branch is followed to step 724.

In step 720, an inquiry is conducted to determine if three numbers of the identified prescriber zip/postal code from the prescription benefit check transaction 102 match a single default pharmacy within the same identified zip/postal code. If the network benefit module 110 identifies a single default pharmacy having a zip/postal code that has three numbers that match at least three numbers of the identified prescriber zip/postal code, then the YES branch is followed to step 722. Otherwise, the NO branch is followed to step 724. In step 722, the service provider computer 104 may format the billing request transaction 204 to a corresponding billing request transaction type and include the identified pharmacy ID associated with the default pharmacy. For example, the billing request transaction type may include, without limitation, a pharmacy billing request (i.e., the billing designation "R"), a prescriber billing request (i.e., a billing designation "P"), an X12 270 eligibility inquiry transaction, or a predetermination of benefits request (i.e., a billing designation "D"). The process then continues to step 414 of FIG. 4.

In step 724, the service provider computer 104 may randomly select a pharmacy within the prescriber zip/postal code and identify the pharmacy ID for that randomly selected pharmacy. The service provider computer 104 may format the billing request transaction 204 to a corresponding billing request transaction type and include the identified pharmacy ID associated with the randomly selected pharmacy. For example, the billing request transaction type may include, without limitation, a pharmacy billing request (i.e., the billing designation "R"), a prescriber billing request (i.e., a billing designation "P"), X12 270 eligibility inquiry transaction, or a predetermination of benefits request (i.e., a billing designation "D"). The process then continues to step 414 of FIG. 4.

Figure 8:
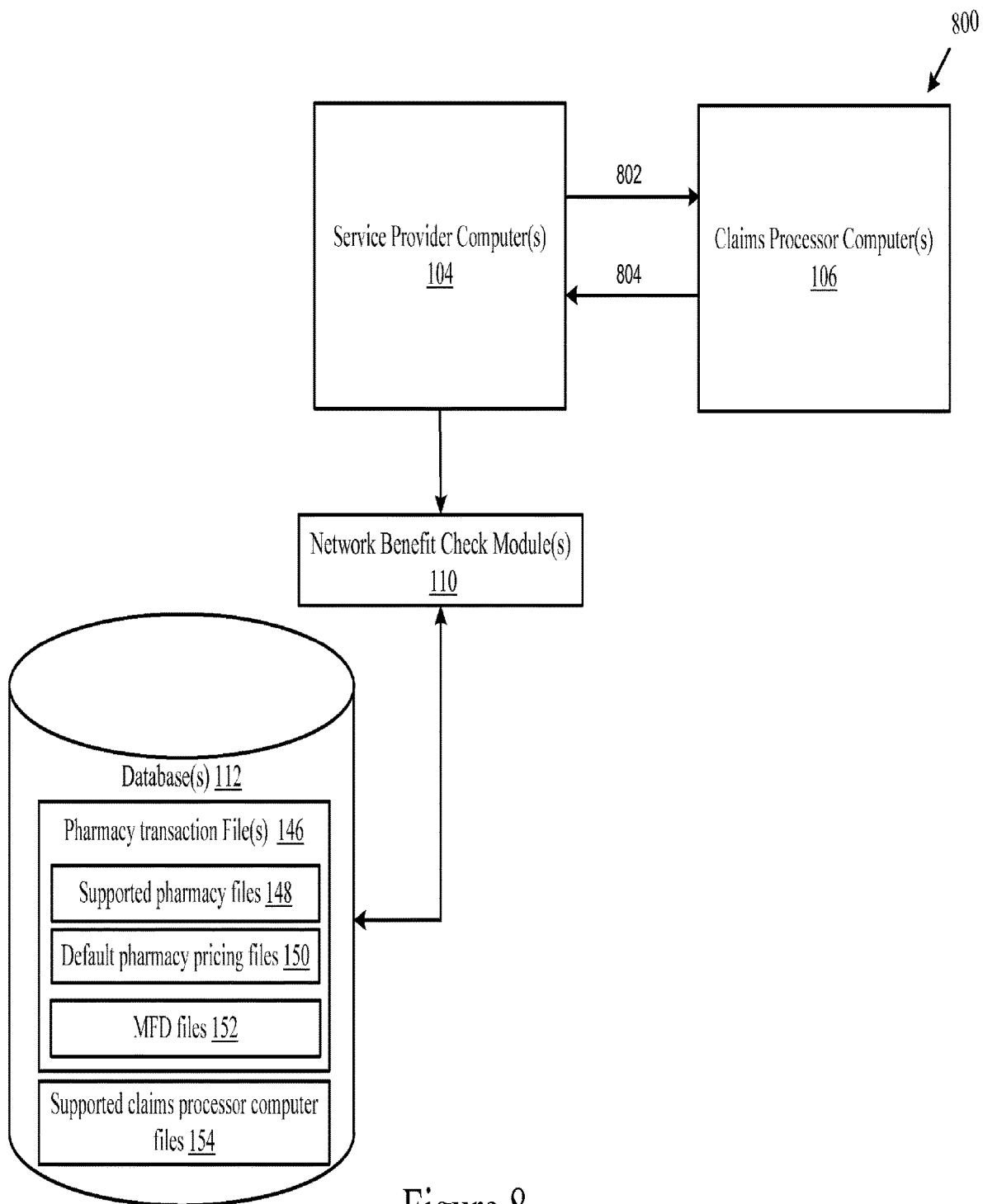
FIG. 8 is a diagram of an example data flow for receiving and communicating a reversal transaction, according to one exemplary embodiment.
Figure 9:
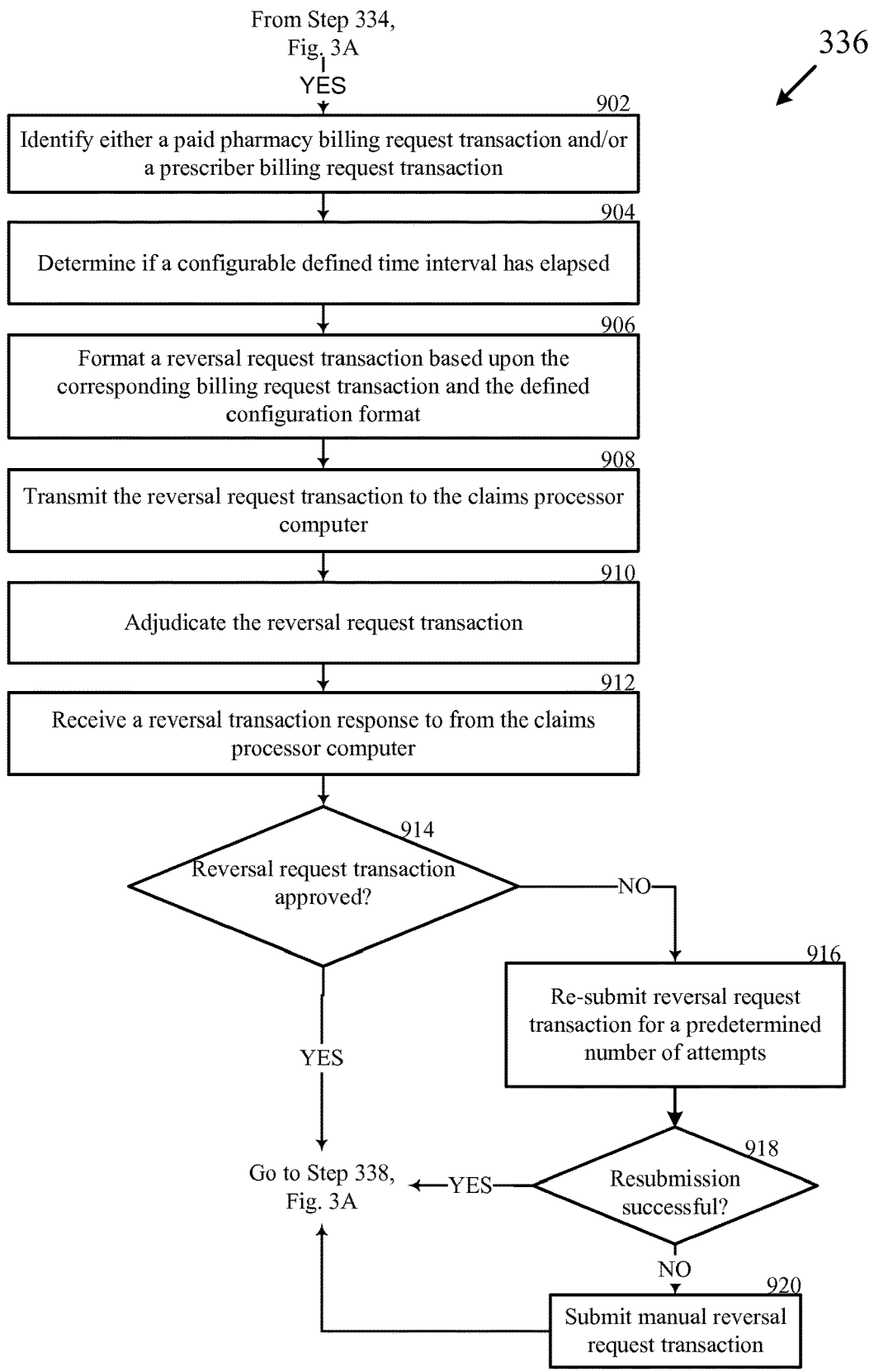
FIG. 9 is a flow chart of an example method for receiving and communicating a reversal transaction, according to one exemplary embodiment.

FIG. 8 illustrates a diagram of an example data flow 800 for generating and transmitting a reversal transaction according to an example embodiment of the disclosure. FIG. 9 is a flow chart illustrating an example method 900 for receiving and communicating a reversal transaction, according to an example embodiment of the disclosure. Referring now to FIGS. 1A-B, 2, 8, and 9, the exemplary method 900 begins at step 902, where the service provider computer 104 may identify whether the billing request transaction 204 was paid. For example, the service provider computer 104 may determine whether the billing request transaction 204 was paid by identifying the transaction status indicator field in the adjudicated response to the billing transaction 206. If the transaction status indicator is populated with a designation representing paid (e.g., a "P"), then the billing request transaction 204 was paid. If the transaction status indicator is field is populated with a designation representing a rejection (e.g., a "R"), then the billing request transaction 204 was rejected. By way of example, FIG. 9 applies to both the pharmacy transaction type (i.e., transaction type "R") and the prescriber transaction type (i.e., transaction type "P").

In step 904, the service provider computer 104 may determine whether a predetermined, user-configurable, defined time interval has elapsed. The predetermined, configurable, defined interval may be any suitable time interval between 0-3600 seconds and may be, such time as 30 seconds, 1 minute, 2 minutes, 3 minutes, 5 minutes, or the like. The predetermined, user-configurable, defined interval may be any suitable time range such as 2 to 3 minutes or the like. The service provider computer 104 may format a reversal request transaction 802 based at least in part upon the corresponding billing transaction type (i.e., pharmacy or prescriber) and the corresponding defined format described herein in step 906.

In step 908, the service provider computer 104 may transmit the reversal request transaction 802 to the claims processor computer 106 via, for example, the network 114. In one example embodiment, the claims processor computer 106 is the same benefits computer to which the corresponding billing request transaction 204 was previously submitted. The reversal request transaction 802 is received at the claims processor computer 106 and the claims processor computer 106 may adjudicate the reversal request transaction 802 and transmit the adjudicated response to the reversal request 804 to the service provider computer 104 in step 910 via, for example, the network 110. In step 912, the service provider computer 104 may receive the adjudicated response to the reversal request 804 from the claims processor computer 106.

In step 914, an inquiry is conducted to determine if the reversal request transaction 802 was approved. In one example embodiment, the determination is made by the network benefit check module 110 or another portion of the service provider computer 104. For example, the network benefit check module 110 can parse the adjudicated response to the reversal request 804 to identify the transaction status field and the code within that field to determine if the transaction 802 was approved. If the reversal request transaction 802 was approved, then the YES branch is followed to step 338 of FIG. 3A. If the reversal request transaction 802 was not approved, then the NO branch is followed to step 916.

In step 916, the service provider computer 104 may resubmit the reversal request transaction 802 to the claims processor computer 106 via, for example, the network 114. The reversal request transaction 802 may be resubmitted to the claims processor computer 106 for a predetermined and user-configurable number of attempts. For example, service provider computer 104 may attempt to resubmit the reversal request transaction 802 to the claims processor computer 106, 2 times, 3 times, or any suitable number of attempts including, but not limited to any number of attempts up to 1000 attempts.

In step 918, an inquiry is conducted to determine if the resubmission of the reversal request transaction 802 was successful (i.e., the reversal request transaction 802 is approved in a received adjudicated response to the reversal request 804. In certain example embodiments, the determination can be made by the network benefit check module 110 or another part of the service provider computer 104. If the resubmission of the reversal request transaction 802 was approved by the claims processor computer 106, then the YES branch is followed and process continues to step 338 of FIG. 3A. If the resubmission of the reversal request transaction 802 was not approved and the maximum number of allowable resubmissions has been reached, then the NO branch is followed to step 920. In step 920, the service provider computer may submit a manual reversal request transaction 802 to the claims processor computer 106. The process then continues to step 338 of FIG. 3A.

Figure 10:
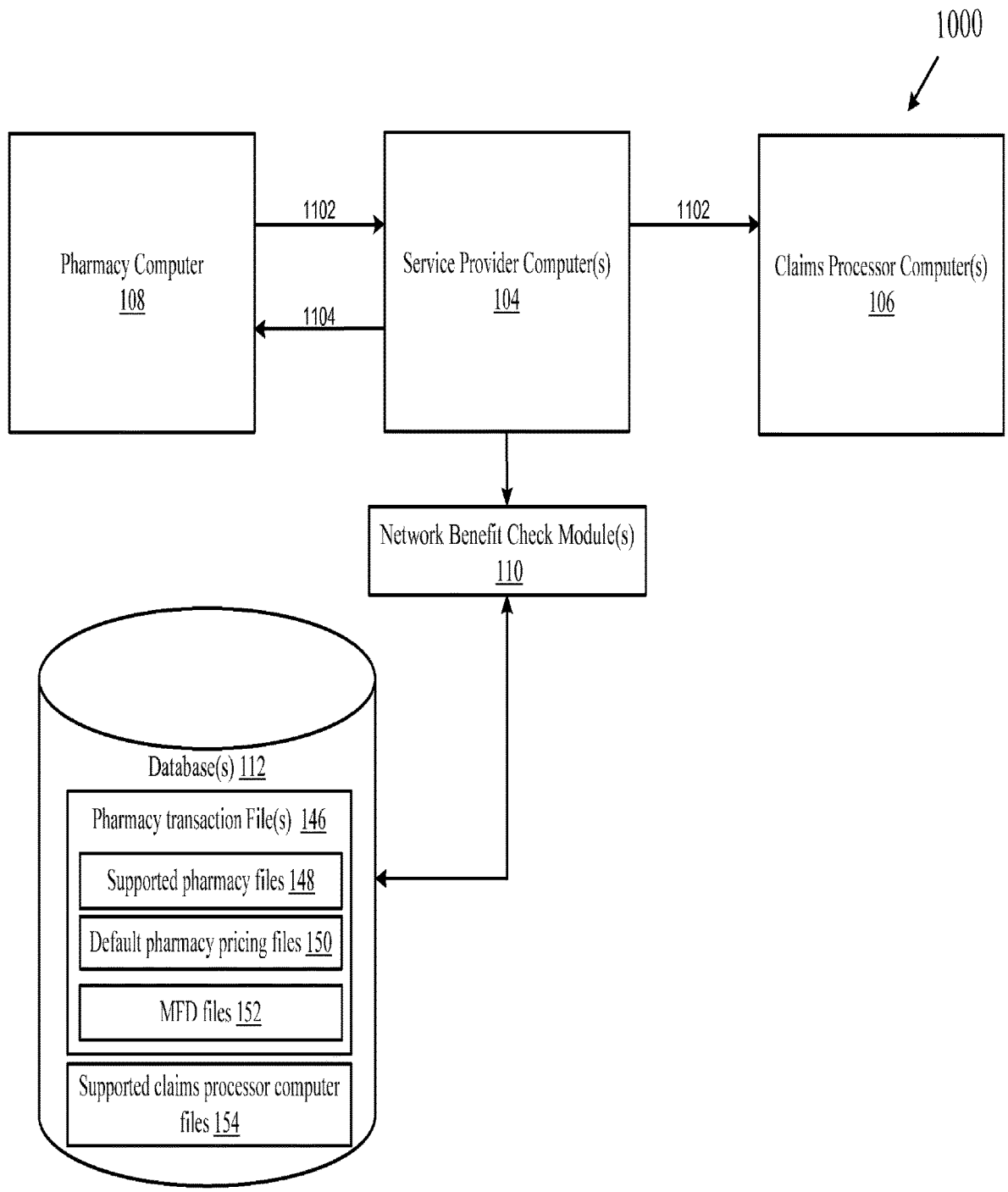
FIG. 10 is a diagram of an example data flow for capturing pharmacy specific data, according to one exemplary embodiment.
Figure 11A:
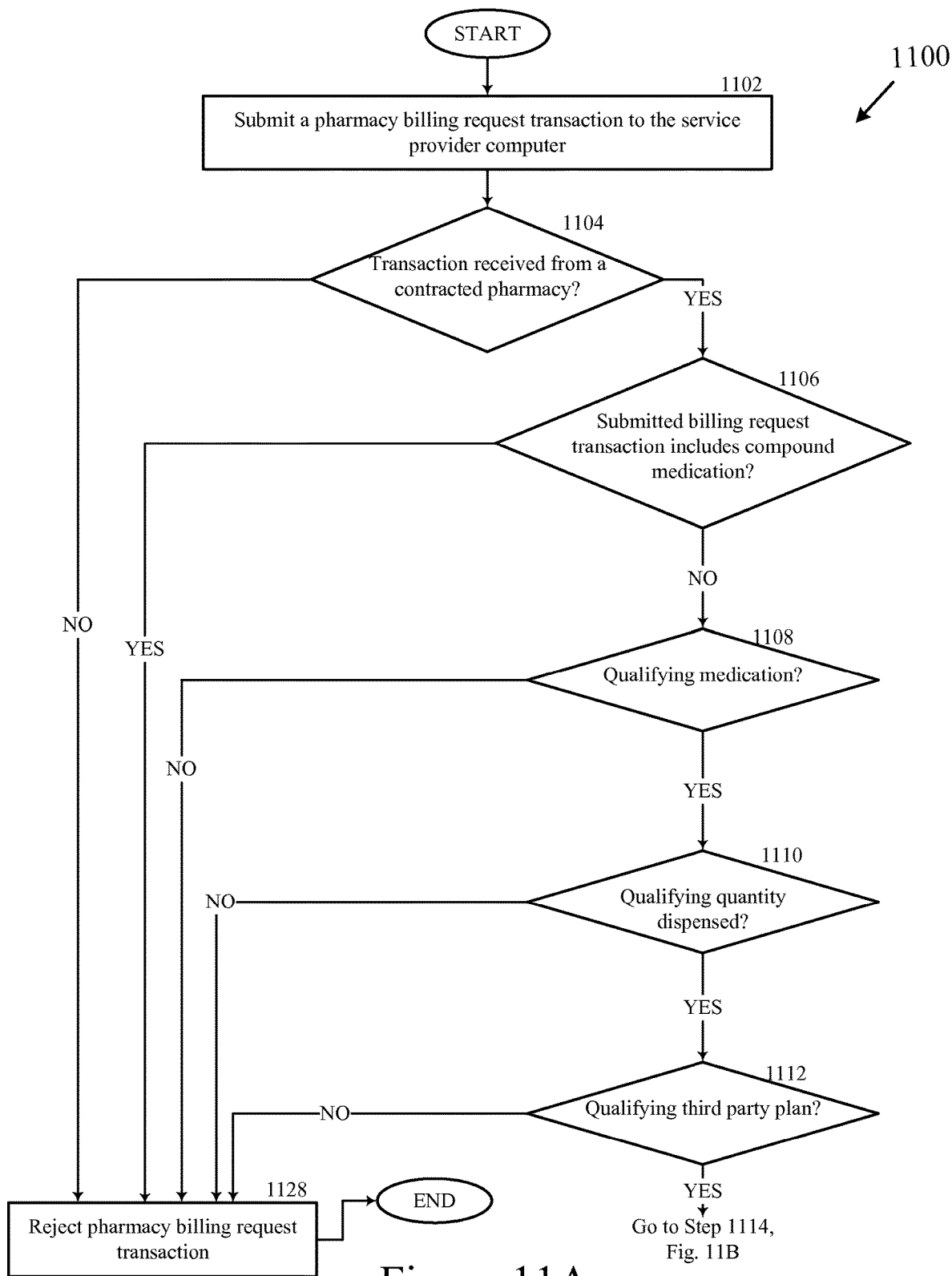
FIGS. 11A and 11B are a flow chart of an example method for capturing pharmacy specific data, according to one exemplary embodiment.
Figure 11B:
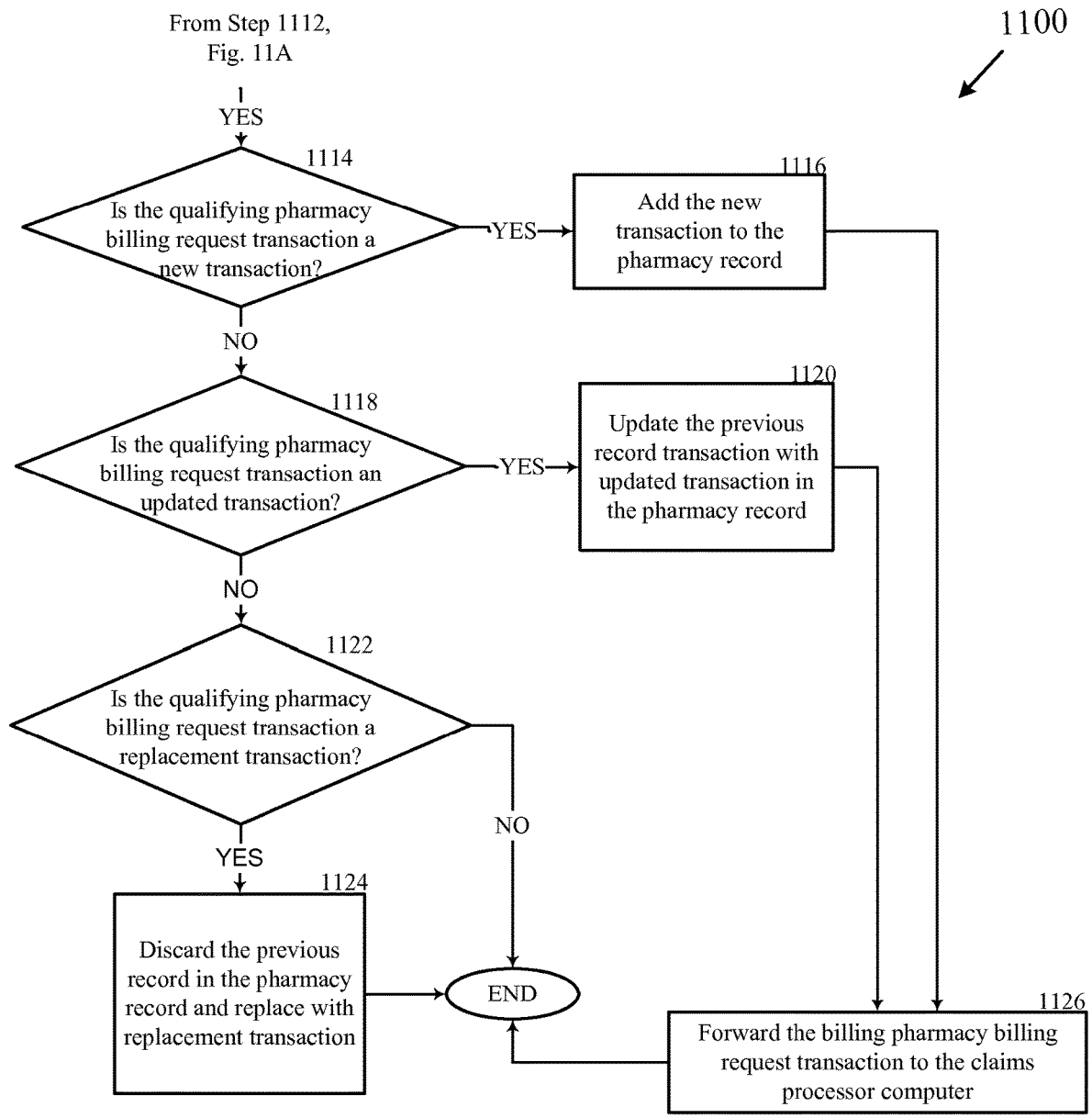

FIG. 10 is a diagram of an example data flow 1000 for capturing pharmacy specific data according to an example embodiment of the disclosure. FIGS. 11A and 11B are a flow chart illustrating an example method 1100 for capturing pharmacy specific data, according to an example embodiment of the disclosure. Referring now to FIGS. 1A-B, 10, and 11A-B, the exemplary method 1100 begins at the START step and continues to step 1102, where the service provider computer 104 may receive a healthcare claim transaction 1002 from a pharmacy computer 108. For example purposes, the healthcare claim transaction will be discussed with reference to a pharmacy billing request transaction in FIGS. 11A-B. However, the description with reference to a pharmacy billing request transaction is not intended to be limiting in any respect.

In step 1104, the service provider computer 104 may employ the network benefit check module 110 to determine whether the pharmacy transmitting and/or identified by a pharmacy ID or identifier in the pharmacy billing request transaction 1002 is a contracted pharmacy. For example, the network benefit check module 110 may access one or more supported pharmacy files 148 in the database 112. The network benefit check module 110 may compare a pharmacy identifier (i.e., a pharmacy name, NPI number, an NCPDP Provider ID, an ePrescribing identifier, a pharmacy identification number, etc.) submitted in the pharmacy billing request transaction 1002 to one or more tables within one or more supported pharmacy files 148. The one or more tables may be include fields including, without limitation, a pharmacy name, a pharmacy identification number, a pharmacy location (i.e., a postal code, an address (including street address, city, state/province, and zip/postal code), etc.), and/or a support designation field including a support indicator (i.e., a "Y" for supported or a "N" for not supported). The network benefit check module 110 may parse the one or more tables within the supported pharmacy files 148 to identify whether the pharmacy identifier exists in the one or more supported pharmacy files. If the pharmacy identifier exists in the one or more supported pharmacy files 148, and a "Y" support indicator accompanies the existing file, then the YES branch is followed to step 1106. If the pharmacy identifier does not exist in the one or more supported pharmacy files 148, and/or a "N" support indicator does not accompany the existing file, and/or a "N" support indicator accompanies the existing file, then the NO branch is followed to step 1128.

In step 1106, the service provider computer 104 may determine whether the submitted pharmacy billing request transaction 1002 includes a compound medication. In one example, the determination may be based upon a value in the Compound Code field included in the pharmacy billing request transaction 1002. If the transaction code indicates a compound medication, then the YES branch is followed to step 1128. If the transaction code does not indicate a compound medication, then the NO branch is followed to step 1108.

In step 1108, the service provider computer 104 may determine whether the pharmacy billing request transaction 1002 is for a qualifying medication. For example, service provider computer 104 may employ the network benefit check module 110 to compare the medication identifier (i.e., NDC, RxNorm medication identifiers, medication name, or the like) to data included in one or more MFD files 152 in the database 112. In one example embodiment, the one or more MFD files 152 may include, one or more fields including a most frequently dispensed medication (MFD) identifier field (i.e., MFD:NDC field). If the medication qualifies, then the YES branch is followed to step 1110. If the medication does not qualify, then the NO branch is followed to step 1128.

In step 1110, the service provider computer 104 may determine whether the pharmacy billing request transaction 1002 is for a qualifying quantity prescribed to be dispensed. For example, service provider computer 104 may employ the network benefit check module 110 to compare the quantity prescribed to be dispensed submitted in the pharmacy billing request transaction 1002 to data included in one or more MFD files 152. For example, the one or more MFD files 152 may include, one or more fields including a most frequently dispensed medication quantity dispensed field (i.e., MFD:quantity dispensed field), and/or a most frequently dispensed medication days' supply dispensed field (i.e., MFD:days' supply dispensed field). If the quantity prescribed qualifies, then the YES branch is followed to step 1112. If the medication and the quantity prescribed do not qualify, then the NO branch is followed to step 1128.

In step 1112, the service provider computer 104 may determine whether the pharmacy billing request transaction 1002 is associated with a claims processor computer 106. In one example embodiment, the service provider computer 104 may compare the BIN Number or the BIN Number and PCN or the BIN Number and Group ID submitted in the pharmacy billing request transaction 1002 with one or more supported claims processor computer files 154 in database 112. The one or more supported claims processor computer files 154 may include, without limitation, a list of one or more claims processor computers 106. If the submitted claims processor computer does not match an excluded claims processor computer in the one or more supported claims processor computer files 154, the submitted claims processor computer is a qualifying claims processor computer and the YES branch is followed to step 1114. If the submitted claims processor computer matches an excluded claims processor computer in the one or more supported claims processor computer files 154, then the NO branch is followed to step 1128.

In step 1114, the service provider computer 104 may determine whether the pharmacy billing request transaction 1002 is a new transaction. For example, if the pharmacy billing request transaction 1002 is from a contracted pharmacy for a medication and/or quantity dispensed that does not exist in the pharmacy transaction files 146, the pharmacy billing request transaction 1002 is designated as a new transaction. If the pharmacy billing request transaction is a new transaction, the YES branch is followed to step 1116. If the pharmacy billing request transaction is not a new transaction, the NO branch is followed to step 1118. In step 1116, the service provider computer may create a new record in the pharmacy transaction files 146. The new record may include, without limitation, the contracted pharmacy information, the medication information, cost information, and/or the quantity dispensed information.

In step 1118, the service provider computer 104 may determine whether the pharmacy billing request transaction 1002 is an updated transaction. For example, if the pharmacy billing request transaction 1002 is from a contracted pharmacy for a medication and/or quantity dispensed that includes updated information in a record in the pharmacy transaction files 146, the pharmacy billing request transaction 1002 is designated as an updated transaction. If the pharmacy billing request transaction is an updated transaction, the YES branch is followed to step 1120. If the pharmacy billing request transaction is not an updated transaction, the NO branch is followed to step 1122. In step 1120, the service provider computer may update the record in the pharmacy transaction files 146. The updated record may include, without limitation, the contracted pharmacy information (e.g., pharmacy identification qualifier, pharmacy identification, store and/or chain name, Group ID, BIN Number, or the like), the medication information (i.e., medication name(s), NDC number(s), RxNorm medication identifiers, cost information, and/or the quantity dispensed information.

In step 1122, the service provider computer 104 may determine whether the pharmacy billing request transaction 1002 is a replacement transaction. For example, if the pharmacy billing request transaction 1002 is from a contracted pharmacy for a medication and/or quantity dispensed that includes replacement information for a record in the pharmacy transaction files 146, the pharmacy billing request transaction 1002 is designated as a replacement transaction. If the pharmacy billing request transaction is a replacement transaction, the YES branch is followed to step 1124. If the pharmacy billing request transaction is not a replacement transaction, the NO branch is followed to the END step.

At step 1124, the service provider computer may discard the previous record in the pharmacy transaction files 146 and replace the record with the replacement transaction. The replacement record may include, without limitation, the contracted pharmacy information, the medication information, cost information, and/or the quantity dispensed information. The process continues to the END step.

In step 1126, if the pharmacy billing request transaction 1002 is designated as a new transaction or an updated transaction, the service provider computer may forward the pharmacy billing request transaction 1002 to the claims processor computer 106. The process continues to the END step. In step 1128, the service provider may reject the pharmacy billing request transaction 1102 and a reject pharmacy billing request transaction 1104 may be delivered back to the pharmacy computer 108. The process continues to the END step.

The methods described and shown in FIGS. 3A-7, 9, and 11A-B may be carried out or performed in any suitable order as desired in various embodiments. Additionally, in certain exemplary embodiments, at least a portion of the operations may be carried out in parallel. Furthermore, in certain exemplary embodiments, less than or more than the operations described in FIGS. 3A-7, 9, and 11A-B may be performed.

Accordingly, example embodiments disclosed herein can provide the technical effects of creating a system and method that determines an incentive available for a medication to be prescribed by a prescriber and modifies the patient copay amount by the amount of the identified incentive prior to transmitting a response to a prescription benefit check transaction that includes a designation of the expected patient copay amount to the prescriber. In this regard, the prescriber is able to accurately determine the patient copay amount and provide this information to the patient prior to prescribing the medication and prior to the patient filling the prescription at a pharmacy. The copay information provided by the prescriber to the patient may also more accurately reflect the copay amount the patient will pay when the patient actually fills the prescription, thereby increasing the likelihood the patient will fill the prescription, Although example embodiments of the disclosure have been described, one of ordinary skill in the art will recognize that numerous other modifications and alternative embodiments are within the scope of the disclosure. For example, any of the functionality and/or processing capabilities described with respect to a particular device or component may be performed by any other device or component. Furthermore, while various example implementations and architectures have been described in accordance with example embodiments of the disclosure, one of ordinary skill in the art will appreciate that numerous other modifications to the example implementations and architectures described herein are also within the scope of this disclosure.

Certain aspects of the disclosure are described above with reference to block and flow diagrams of systems, methods, apparatuses, and/or computer program products according to example embodiments. It will be understood that one or more blocks of the block diagrams and steps of the flow diagrams, and combinations of blocks in the block diagrams and steps of the flow diagrams, respectively, may be implemented by execution of computer-executable program instructions. Likewise, some blocks of the block diagrams and steps of the flow diagrams may not necessarily need to be performed in the order presented, or may not necessarily need to be performed at all, according to some embodiments. Further, additional components and/or operations beyond those depicted in blocks of the block diagrams and/or steps of the flow diagrams may be present in certain embodiments.

Accordingly, blocks of the block diagrams and steps of the flow diagrams support combinations of means for performing the specified functions, combinations of elements or steps for performing the specified functions and program instruction means for performing the specified functions. It will also be understood that each block of the block diagrams and step of the flow diagrams, and combinations of blocks in the block diagrams and steps of the flow diagrams, may be implemented by special-purpose, hardware-based computer systems that perform the specified functions, elements or steps, or combinations of special-purpose hardware and computer instructions.

Computer-executable program instructions may be loaded onto a special-purpose computer or other particular machine, a processor, or other programmable data processing apparatus to produce a particular machine, such that execution of the instructions on the computer, processor, or other programmable data processing apparatus causes one or more functions or steps specified in the flow diagrams to be performed. These computer program instructions may also be stored in a computer-readable storage medium (CRSM) that upon execution may direct a computer or other programmable data processing apparatus to function in a particular manner, such that the instructions stored in the computer-readable storage medium produce an article of manufacture including instruction means that implement one or more functions or steps specified in the flow diagrams. The computer program instructions may also be loaded onto a computer or other programmable data processing apparatus to cause a series of operational elements or steps to be performed on the computer or other programmable apparatus to produce a computer-implemented process.

Additional types of CRSM that may be present in any of the devices described herein may include, but are not limited to, programmable random access memory (PRAM), SRAM, DRAM, RAM, ROM, electrically erasable programmable read-only memory (EEPROM), flash memory or other memory technology, compact disc read-only memory (CD-ROM), digital versatile disc (DVD) or other optical storage, magnetic cassettes, magnetic tape, magnetic disk storage or other magnetic storage devices, or any other medium which can be used to store the information and which can be accessed. Combinations of any of the above are also included within the scope of CRSM. Alternatively, computer-readable communication media (CRCM) may include computer-readable instructions, program modules, or other data transmitted within a data signal, such as a carrier wave, or other transmission. However, as used herein, CRSM does not include CRCM.

Although example embodiments have been described in language specific to structural features and/or methodological acts, it is to be understood that the disclosure is not necessarily limited to the specific features or acts described. Rather, the specific features and acts are disclosed as illustrative forms of implementing the example embodiments. Conditional language, such as, among others, "can," "could," "might," or "may," unless specifically stated otherwise, or otherwise understood within the context as used, is generally intended to convey that certain example embodiments could include, while other example embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

That which is claimed is:

1. A computer-implemented method, comprising:
reformatting, by one or more service provider computers and in response to receiving a prescription benefit check transaction, the prescription benefit check transaction into a billing request transaction, wherein the billing request transaction is populated with a medication identifier identifying a medication to be prescribed and a patient identifier identifying a patient to receive the prescribed medication from the prescription benefit check transaction, wherein reformatting the prescription benefit check transaction into a billing request transaction further comprises:
determining, by the one or more service provider computers, a pharmacy identifier to insert into the billing request transaction;
inserting, by the one or more service provider computers, the pharmacy identifier into the billing request transaction;
determining a transaction type of the prescription benefit check transaction, wherein the transaction type comprises a pharmacy billing request, a prescriber billing request, a predetermination of benefits request or an eligibility inquiry transaction; and
reformatting the prescription benefit check transaction into the billing request transaction having a corresponding type as the transaction type of the prescription benefit check transaction;

following adjudication of the billing request transaction by a claims processor computer, determining, by the one or more service provider computers, an incentive amount to apply to a first patient copay amount of an adjudicated response to the billing request transaction;

generating, by the one or more service provider computers, a second patient copay amount by reducing the first patient copay amount based upon the determined incentive amount;

including, by the one or more service provider computers, the second patient copay amount in the adjudicated response to the billing request transaction; and transmitting, by the one or more service provider computers, the adjudicated response to the billing request transaction to a prescriber computer.

2. The computer-implemented method of claim 1, further comprising:

generating, by the one or more service provider computers, an incentive notification message, wherein the incentive notification message comprises a notification that the incentive amount was applied against the first patient copay amount and identifies a provider of the incentive amount; and transmitting, by the one or more service provider computers, the incentive notification message to the prescriber computer.

3. The computer-implemented method of claim 2, wherein the incentive notification message is inserted, by the one or more service provider computers, into a field of the adjudicated response to the billing request transaction prior to transmitting the adjudicated response to the billing request transaction to the prescriber computer.

4. The computer-implemented method of claim 2, wherein the incentive notification message is transmitted to the prescriber computer separately from the adjudicated response to the billing request transaction.

5. The computer-implemented method of claim 1, wherein determining an incentive amount to apply to the first patient copay amount comprises:

retrieving, by the one or more service provider computers, the medication identifier;

comparing, by the one or more service provider computers, the medication identifier to a list of medication identifiers representing medications for which an incentive amount is available to determine if a match exists; and determining, by the one or more service provider computers, the incentive amount is available for the medication identified by the medication identifier based on a positive determination that the match exists.

6. The computer-implemented method of claim 5, wherein the medication identifier is retrieved from one of the adjudicated response, the billing request transaction, or the prescription benefit check transaction.

7. The computer-implemented method of claim 5, wherein the adjudicated response to the billing request transaction further comprises a pharmacy identifier identifying a pharmacy and wherein the method further comprises the steps of:

retrieving, by the one or more service provider computers, the pharmacy identifier from the adjudicated response to the billing request transaction;

comparing, by the one or more service provider computers, the pharmacy identifier to a list of pharmacy identifiers representing pharmacies receiving an incentive amount determination service to determine if a match to the pharmacy identifier exists; and determining, by the one or more service provider computers, the pharmacy identified by the pharmacy identifier receives the incentive amount determination service based on a positive determination that the match to the pharmacy identifier exists.

8. The computer-implemented method of claim 1, wherein the incentive amount is one of a coupon, a discount, or a rebate.

9. The computer-implemented method of claim 1, further comprising:

determining, by the one or more service provider computers from the adjudicated response to the billing request transaction, that the billing request transaction was adjudicated as paid by the claims processor computer;

generating, by the one or more service provider computers, a reversal request transaction based at least in part upon the billing request transaction; and transmitting, by the one or more service provider computers, the reversal request transaction to the claims processor computer.

10. A system comprising:

at least one memory operable to store computer-executable instructions; and at least one processor configured to access the at least one memory and execute the computer-executable instructions to:

reformat, in response to receiving a prescription benefit check transaction, the prescription benefit check transaction into a billing request transaction, wherein the billing request transaction is populated with a medication identifier identifying a medication to be prescribed and a patient identifier identifying a patient to receive the prescribed medication from the prescription benefit check transaction, wherein reformatting the prescription benefit check transaction into a billing request transaction further comprises:

determine a pharmacy identifier to insert into the billing request transaction;

insert the pharmacy identifier into the billing request transaction;

determine a transaction type of the prescription benefit check transaction, wherein the transaction type comprises a pharmacy billing request, a prescriber billing request, a predetermination of benefits request or an eligibility inquiry transaction; and reformat the prescription benefit check transaction into the billing request transaction having a corresponding type as the transaction type of the prescription benefit check transaction;

following adjudication of the billing request transaction by a claims processor computer, determine an incentive amount to apply to a first patient copay amount of an adjudicated response to the billing request transaction;

generate a second patient copay amount based upon reducing the first patient copay amount by the determined incentive amount;

include the second patient copay amount in the adjudicated response to the billing request transaction; and direct communication of the adjudicated response to the billing request transaction to a prescriber computer.

11. The system of claim 10, wherein the at least one processor is further configured to access the at least one memory and execute the computer-executable instructions to:

generate an incentive notification message, wherein the incentive notification message comprises a notification that the incentive amount was applied against the first patient copay amount and identifies a provider of the incentive amount; and direct communication of the incentive notification message to the prescriber computer.

12. The system of claim 11, wherein the at least one processor is further configured to access the at least one memory and execute the computer-executable instructions to insert the incentive notification message into a field of the adjudicated response to the billing request transaction prior to directing communication of the adjudicated response to the billing request transaction to the prescriber computer.

13. The system of claim 11, wherein the incentive notification message is transmitted to the prescriber computer separately from the adjudicated response to the billing request transaction.

14. The system of claim 10, wherein the at least one processor is further configured to determine an incentive amount to apply to the first patient copay amount of the adjudicated response to the billing request transaction by accessing the at least one memory and execute the computer-executable instructions to:

retrieve the medication identifier;

compare the medication identifier to a list of medication identifiers representing medications for which an incentive amount is available to determine if a match exists; and determine the incentive amount is available for the medication identified by the medication identifier based on a positive determination that the match exists.

15. The system of claim 14, wherein the adjudicated response to the billing request transaction further comprises a pharmacy identifier identifying a pharmacy and wherein the at least one processor is further configured to access the at least one memory and execute the computer-executable instructions to:

retrieve the pharmacy identifier from the adjudicated response to the billing request transaction;

compare the pharmacy identifier to a list of pharmacy identifiers representing pharmacies receiving an incentive amount determination service to determine if a match to the pharmacy identifier exists; and determine the pharmacy identified by the pharmacy identifier receives the incentive amount determination service based on a positive determination that the match to the pharmacy identifier exists.

16. The system of claim 10, wherein the incentive amount is one of a coupon, a discount, or a rebate.

17. The system of claim 10 wherein the prescription benefit check transaction is one of a pharmacy billing request, a prescriber billing request, a predetermination of benefits request, or an X12 270 eligibility inquiry transaction.

18. The system of claim 10, wherein the at least one processor is further configured to access the at least one memory and execute the computer-executable instructions to:

determine, from the adjudicated response to the billing request transaction, that the billing request transaction was adjudicated as paid by the claims processor computer;

generate a reversal request transaction based at least in part upon the billing request transaction; and direct communication of the reversal request transaction to the claims processor computer for adjudication.

* * * * *